US011944286B2

(12) United States Patent
Sauer

(10) Patent No.: US 11,944,286 B2
(45) Date of Patent: *Apr. 2, 2024

(54) SURGICAL RIB RETRACTOR

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 344 days.

This patent is subject to a terminal disclaimer.

(21) Appl. No.: 17/157,283

(22) Filed: Jan. 25, 2021

(65) Prior Publication Data

US 2021/0228197 A1 Jul. 29, 2021

Related U.S. Application Data

(60) Provisional application No. 62/965,524, filed on Jan. 24, 2020.

(51) Int. Cl.
*A61B 17/02* (2006.01)
*A61B 17/00* (2006.01)

(52) U.S. Cl.
CPC ........ *A61B 17/0206* (2013.01); *A61B 17/025* (2013.01); *A61B 2017/00398* (2013.01); *A61B 2017/0287* (2013.01)

(58) Field of Classification Search
CPC .............. A61B 17/0206; A61B 17/025; A61B 2017/00398; A61B 2017/0287
USPC ................ 600/214, 215, 217, 219, 222, 235
See application file for complete search history.

(56) References Cited

U.S. PATENT DOCUMENTS 5,365,921 A * 11/1994 Bookwalter ....... A61B 17/0206
403/150
5,716,326 A 2/1998 Dannan
5,865,731 A 2/1999 Lennox
5,944,736 A 8/1999 Taylor
(Continued)

FOREIGN PATENT DOCUMENTS

EP 0792620 9/1997
EP 2705799 12/2014
(Continued)

OTHER PUBLICATIONS

Aug. 31, 2017 International Search Report; Young, Lee W., ISR for PCT/US2017/037572.
(Continued)

*Primary Examiner* — Eduardo C Robert
*Assistant Examiner* — David C Comstock
(74) *Attorney, Agent, or Firm* — Michael E. Coyne

(57) ABSTRACT

A surgical rib retractor has a housing and a body pivotably coupled to the housing and moveable between a closed position and an open position. The retractor also has a first arm unit coupled to the housing and configured to atraumatically receive tissue. The first arm unit has a first arm, a first strut movable relative to the first arm in a first plane defined by the first arm, and a first frame attached to the first strut. The retractor also has a second arm unit coupled to the body and configured to atraumatically receive tissue. The second arm unit has a second arm, a second strut movable relative to the second arm in a second plane defined by the second arm, wherein the second plane is not parallel to the first plane when the body is in the closed position, and a second frame attached to the second strut.

33 Claims, 39 Drawing Sheets

(56) References Cited

U.S. PATENT DOCUMENTS

| | | | | |
|---|---|---|---|---|
| 6,042,540 A * | 3/2000 | Johnston | ............ | A61B 17/0206 600/219 |
| 6,159,231 A | 12/2000 | Looney | | |
| 6,196,969 B1 | 3/2001 | Bester | | |
| 6,302,842 B1 * | 10/2001 | Auerbach | .......... | A61B 17/0206 600/219 |
| 6,416,468 B2 | 7/2002 | Deckman | | |
| 6,663,562 B2 * | 12/2003 | Chang | ................. | A61B 17/0206 600/219 |
| 7,011,628 B2 | 3/2006 | Lidonnici | | |
| 7,186,215 B2 | 3/2007 | Yi | | |
| 7,288,065 B1 | 10/2007 | Taylor | | |
| 8,118,737 B2 | 2/2012 | Perez-Cruet | | |
| 10,420,542 B2 | 9/2019 | Sauer | | |
| 10,603,025 B2 * | 3/2020 | Sauer | ................. | A61B 17/0218 |
| 2001/0041828 A1 * | 11/2001 | Deckman | .......... | A61B 17/0206 600/232 |
| 2003/0060686 A1 | 3/2003 | Taylor | | |
| 2006/0052670 A1 | 3/2006 | Stearns | | |
| 2006/0052673 A1 * | 3/2006 | Santilli | ................. | A61B 17/02 600/234 |
| 2007/0073111 A1 * | 3/2007 | Bass | ................. | A61B 17/0206 600/219 |
| 2007/0203400 A1 | 8/2007 | Santilli | | |
| 2011/0224496 A1 * | 9/2011 | Weiman | ............. | A61B 17/0206 600/231 |
| 2014/0133173 A1 | 5/2014 | Vayser | | |
| 2015/0182211 A1 * | 7/2015 | Nowak | .............. | A61B 17/0206 600/215 |
| 2016/0030030 A1 * | 2/2016 | Bass | ................. | A61B 17/0206 600/215 |
| 2018/0177499 A1 | 6/2018 | Sauer | | |
| 2018/0296203 A1 * | 10/2018 | Powley | ............. | A61B 17/0206 |
| 2021/0153857 A1 * | 5/2021 | Hill | ...................... | A61B 17/025 |

FOREIGN PATENT DOCUMENTS

| | | |
|---|---|---|
| WO | WO2012/040206 | 3/2012 |
| WO | WO2016/040497 | 3/2016 |

OTHER PUBLICATIONS

Dec. 18, 2019 Extended European Search Result for corresponding U.S. Appl. No. 17/814,055.

Dec. 18, 2020 International Search Report for PCT/US20/46137.

* cited by examiner

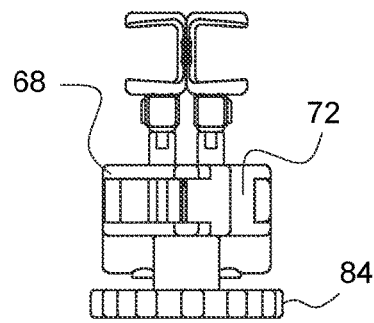
FIG. 2E
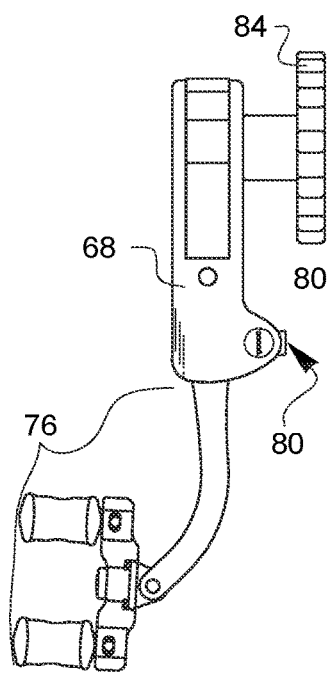
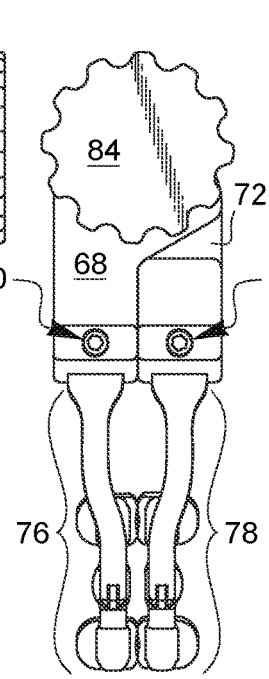
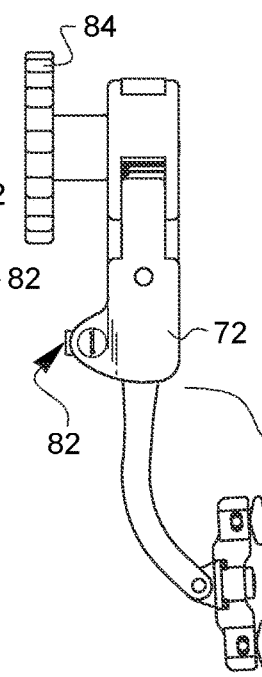
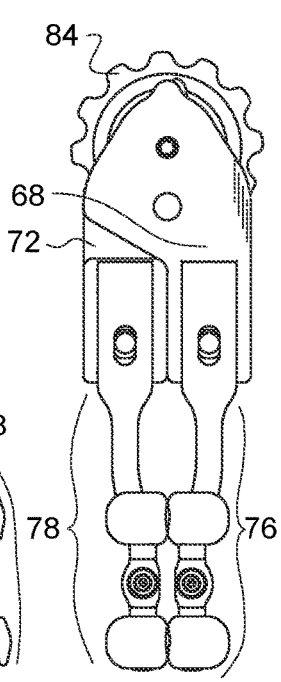
FIG. 2B  FIG. 2A  FIG. 2C  FIG. 2D
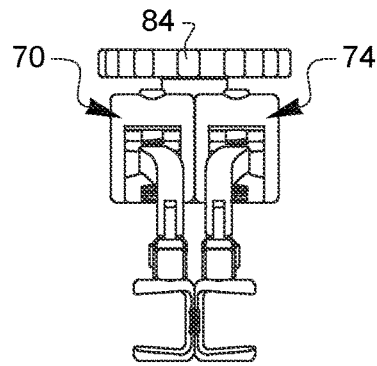
FIG. 2F

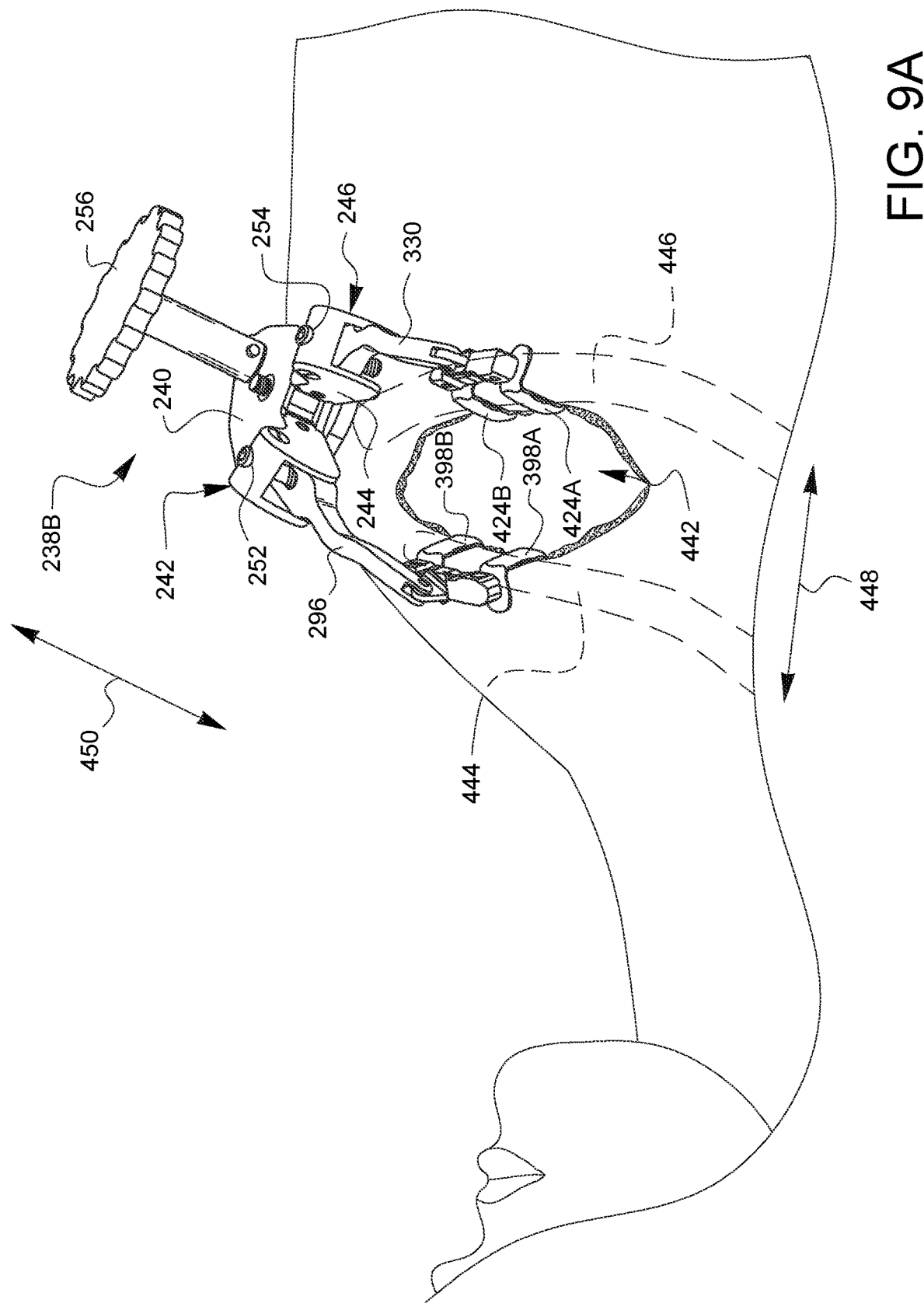

SURGICAL RIB RETRACTOR

RELATED APPLICATIONS

This application claims priority to U.S. Provisional Patent Application No. 62/965,524 filed Jan. 24, 2020 and entitled, "SURGICAL RIB RETRACTOR". The 62/965,524 application is hereby incorporated by reference in its entirety.

FIELD

The claimed invention relates to rib retraction devices, and more specifically to surgical rib or soft tissue retraction devices for minimally invasive surgery.

BACKGROUND

Advances in cardiac surgery have enabled open heart and less-invasive methods for a wide variety of cardiac surgical procedures such as heart valve replacements or repairs. In many of these procedures, it is often necessary to retract tissue and bones in order to provide access to a surgical site. For example, in a sternotomy, where a vertical inline incision is made along the sternum, after which the sternum is divided or "cracked", a large sternum retractor is used to force the cracked sternum apart, providing access to the heart. Such sternum retractors have jaws which open in a single plane. While a sternotomy provides excellent access to the heart, the procedure is highly invasive and is associated with a high degree of post-operative pain and long recovery times for patients.

With advances in minimally invasive cardiac approaches, surgeons have been able to move away from sternotomies for many procedures. For example, one favored approach to access the heart is to use a right anterior thoracotomy (a much smaller incision in the chest wall). The thoracotomy is often made between two adjacent ribs, and it is often necessary to spread those ribs apart to create an access window for the surgery. This can be done with a smaller version of the single plane style retractor, or, in some cases, with hand-pulled retractors. Hand-pulled retractors require an extra person's pair of hands, which may crowd the operating area around the patient. Hand retractors are also difficult to maintain in an open position over an extended period of time. Therefore, a mechanical rib retractor may be favored over the hand-retractors, since it provides steady, sustained retraction and may reduce operator fatigue and even the need for an additional person in the operating room.

Unfortunately, traditional thoracotomies, made through adjacent ribs, often do not provide enough access for certain types of cardiac procedures. While surgical instruments such as fiber optic scopes, forceps, cutting tools, and suturing tools may fit relatively well through a thoracotomy between adjacent ribs, replacement heart valves and their holders often do not (even when the adjacent ribs are spread apart with existing retractors). As a result, for many cardiac procedures, the thoracotomy often requires resection or removal of ribs in order to provide additional room for larger items, such as a replacement heart valve. While transection with or without reattachment of a rib can be less traumatic than a sternotomy, it would still be desirable to avoid excessive rib mobilization in order to provide less post-operative pain and quicker recovery times for patients. Another potential disadvantage of most known mechanical rib retractors is the high concentration of force exerted onto the rib and surrounding soft tissue when in use. Retractor blades or attachments exert significant mechanical forces on the ribs and surrounding tissue. The localized forces may cause tissue damage, and in some cases the damage may be irreversible.

Several other types of rib retractors have been developed in order to try to provide a larger access space between adjacent ribs. Before describing these retractors, however, it is helpful to consider different orientations of human anatomy so that the motion and operation of the retractors can be compared and contrasted according to how they move relative to the anatomy. Three anatomical planes divide the body into different sectors. The sagittal plane divides the body into a left portion and a right portion. The coronal plane divides the body into an anterior (front) portion and a posterior (back) portion. The transverse plane divides the body into an upper portion and a lower portion. A direction towards the head may generally be referred to as a cephalad direction, while a direction towards the lower end of the spine may generally be referred to as a caudad direction. Therefore, an axis running approximately in a direction from the head towards the lower portion of the body could be referred to as a substantially cephalad-caudal axis. Similarly, an axis running approximately in a direction from the back of the body to the front of the body could be referred to as a substantially anterior-posterior axis.

U.S. Pat. No. 5,865,731 discloses a surgical retractor that "is able to form an oblique tunnel-like opening at an incision site wherein, in addition to spreading the sides of the site incision substantially parallel to the contour of the patient's body, the '731 surgical retractor additionally spreads the incision sides so that one side is depressed toward the patient and the other is directed outwardly from the patient." However, the rotational or offset positions for the grips must be predetermined before use since only one amount of anterior-posterior movement is possible during use. Furthermore, there is no spreading of the ribs in a cephalad-caudal direction without also having anterior-posterior separation. This may be undesirable since the additional anterior-posterior separation (and its resultant stress on the ribs) may not be needed for the entire duration of an operation.

U.S. Pat. No. 6,159,231 discloses a retractor having two racks movably attached at a nonlinear angle. When the first rack section is horizontally disposed, the other rack section is angled relative to the horizontal plane. The retractor may be ratcheted apart to spread adjacent ribs in a cephalad-caudal direction. One end of the retractor may also be lifted to spread the ribs in an anterior-posterior direction. The lifted end, however, must be held by hand or attached to a cable anchored to a support over the patient in order to maintain the anterior-posterior separation. This either requires additional personnel in the operating room, or modifications to the operating table/ceiling, neither of which is desirable as the additional equipment may get in the surgeon's way.

European Patent 792,620 discloses several embodiments of a rib retractor having adjustments to spread adjacent ribs in a cephalad-caudal direction. These retractors also have an adjustment to lift one rib relative to the other by contacting the patient somewhere else besides the ribs to create a fulcrum point for lifting leverage. Unfortunately, this retractor may be difficult to use on obese patients and is not simple to adjust and lock in place in general.

European Patent 792,620 also discloses a version of a rib retractor where the spreader is attached to the operating table or to some platform which can be slid beneath the patient. This rib retractor has adjustments for both anterior-posterior separation as well as cephalad-caudal separation. While this embodiment alleviates the unnecessary bruising of previous models, its external anchoring system is also complex, cumbersome, and difficult to reposition.

European Patent 792,620 further discloses an embodiment of a rib retractor which spreads the ribs in a cephalad-caudal direction while simultaneously spreading the ribs in an anterior-posterior direction. However, like other examples from the prior art, there is no way to fine tune the opening, or to have one type of separation without the other, if desired, for a portion of the operation with this one retractor.

U.S. Pat. No. 6,416,468 discloses a rib retractor which can generate cephalad-caudal separation of the ribs, as well as an uneven amount of anterior-directed lift on the adjacent ribs. The '468 retractor has no opposing anterior-posterior rib movement. Furthermore, the '468 device employs a pivot point placed against the patient's body, somewhere in addition to the rib contact points, which can result in further bruising and discomfort.

Therefore, there is a need for an improved surgical rib retractor which can provide for varying and controlled amounts of rib separation in both a cephalad-caudal direction as well as an anterior-posterior direction, while minimizing the force exerted by the retractor onto ribs, surrounding tissue, and other anatomical features.

SUMMARY

A surgical rib retractor is disclosed. The retractor has a housing and a body pivotably coupled to the housing and moveable between a closed position and an open position. The retractor also has a first arm unit coupled to the housing and configured to atraumatically receive tissue. The first arm unit has a first arm, a first strut movable relative to the first arm in a first plane defined by the first arm, and a first frame attached to the first strut. The retractor also has a second arm unit coupled to the body and configured to atraumatically receive tissue. The second arm unit has a second arm, a second strut movable relative to the second arm in a second plane defined by the second arm, wherein the second plane is not parallel to the first plane when the body is in the closed position, and a second frame attached to the second strut.

Another surgical rib retractor is disclosed. The retractor has a housing having a first shoulder, wherein the housing defines an actuator guide opening. The retractor also has a body comprising a second shoulder and a drive gear, the body pivotably coupled to the housing. The retractor further has a first arm unit comprising a first frame, pivotably coupled to the first shoulder and configured to atraumatically receive tissue. The retractor also has a second arm unit comprising a first frame, pivotably coupled to the second shoulder and configured to atraumatically receive tissue. The retractor further has a first arm actuator constrained to be rotatable relative to the first shoulder and coupled to the first arm unit to pivot the first arm unit as the first arm actuator is rotated. The retractor also has a second arm actuator constrained to be rotatable relative to the second shoulder and coupled to the second arm unit to pivot the second arm unit as the second arm actuator is rotated. The retractor further has a drive actuator configured to pivot the body relative to the housing. The drive actuator has an actuation gear, a knob, a pawl arm deflection portion, and an actuation key configured to engage at least one of the first and second arm actuators for rotation. The actuator guide opening is sized to accept the actuation gear and align it with the drive gear for turning the drive gear.

A further surgical rib retractor is disclosed. The retractor has a housing having a first shoulder. The retractor also has a body pivotably coupled to the housing and having a second shoulder. The retractor further has a first arm unit comprising a first frame, pivotably coupled to the first shoulder and configured to atraumatically receive tissue. The retractor also has a second arm unit comprising a first frame, pivotably coupled to the second shoulder and configured to atraumatically receive tissue. The retractor further has a first arm actuator constrained to be rotatable relative to the first shoulder and coupled to the first arm unit to pivot the first arm unit as the first arm actuator is rotated. The retractor also has a second arm actuator constrained to be rotatable relative to the second shoulder and coupled to the second arm unit to pivot the second arm unit as the second arm actuator is rotated.

BRIEF DESCRIPTION OF THE DRAWINGS

FIGS. 2A, 2B, 2C, 2D, 2E, 2F are top, left, right, bottom, rear, and front elevational views of the surgical rib retractor embodiment of FIG. 1A.

FIG. 9A illustrates one view of the retractor from FIG. 7A installed in a minimally invasive surgical opening without the anti-cant feature.

Figure 1A:
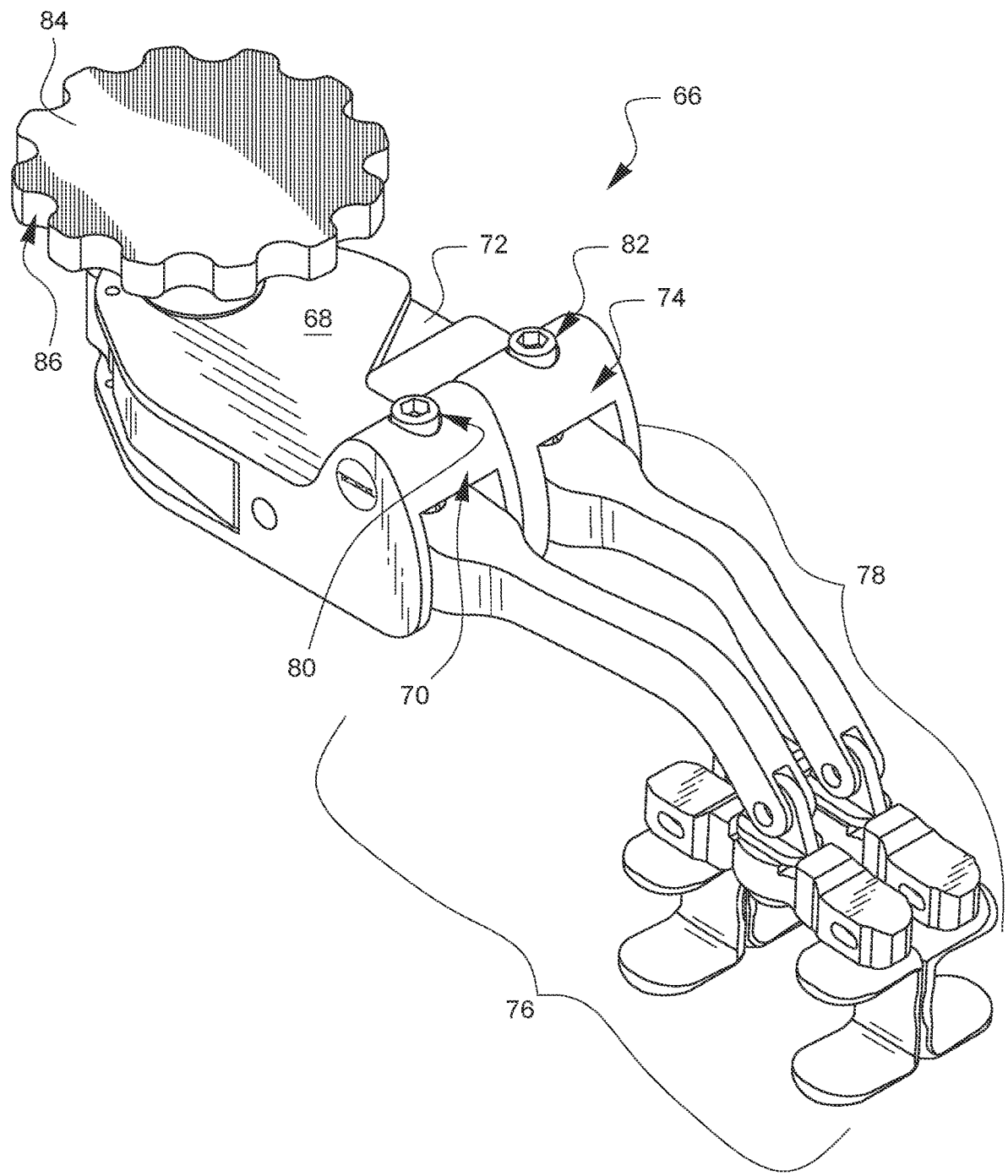
FIG. 1A is a front-top-left perspective view of one embodiment of a surgical rib retractor.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIG. 1A is a front-top-left perspective view of one embodiment of a surgical rib retractor 66. The retractor 66 has a housing 68. The housing 68 has a first shoulder 70. The retractor 66 also has a body 72 pivotably coupled to the housing 68 and having a second shoulder 74. The surgical rib retractor 66 also has a first arm unit 76 pivotably coupled to the first shoulder and configured to receive one rib. The surgical rib retractor 66 also has a second arm unit 78 pivotably coupled to the second shoulder 74 and configured to receive another rib.

The surgical rib retractor 66 has a first arm actuator 80 constrained to be rotatable relative to the first shoulder 70 and coupled to the first arm unit 76 to pivot the first arm unit 76 as the first arm actuator 80 is rotated. Similarly, the retractor 66 also has a second arm actuator 82 constrained to be rotatable relative to the second shoulder 74 and coupled to the second arm unit 78 to pivot the second arm unit 78 as the second arm actuator 82 is rotated.

The surgical rib retractor 66 also has a drive actuator 84. The drive actuator 84 is configured to pivot the body 72 relative to the housing 68. In this embodiment, the drive actuator 84 includes a knob 86 and a gear (not visible in this view). In other embodiments, the drive actuator could comprise a variety of elements, including one or more gears, one or more knobs, one or more levers, one or more pulleys, one or more motors, one or more solenoids, or any combination thereof.

Figure 1B:
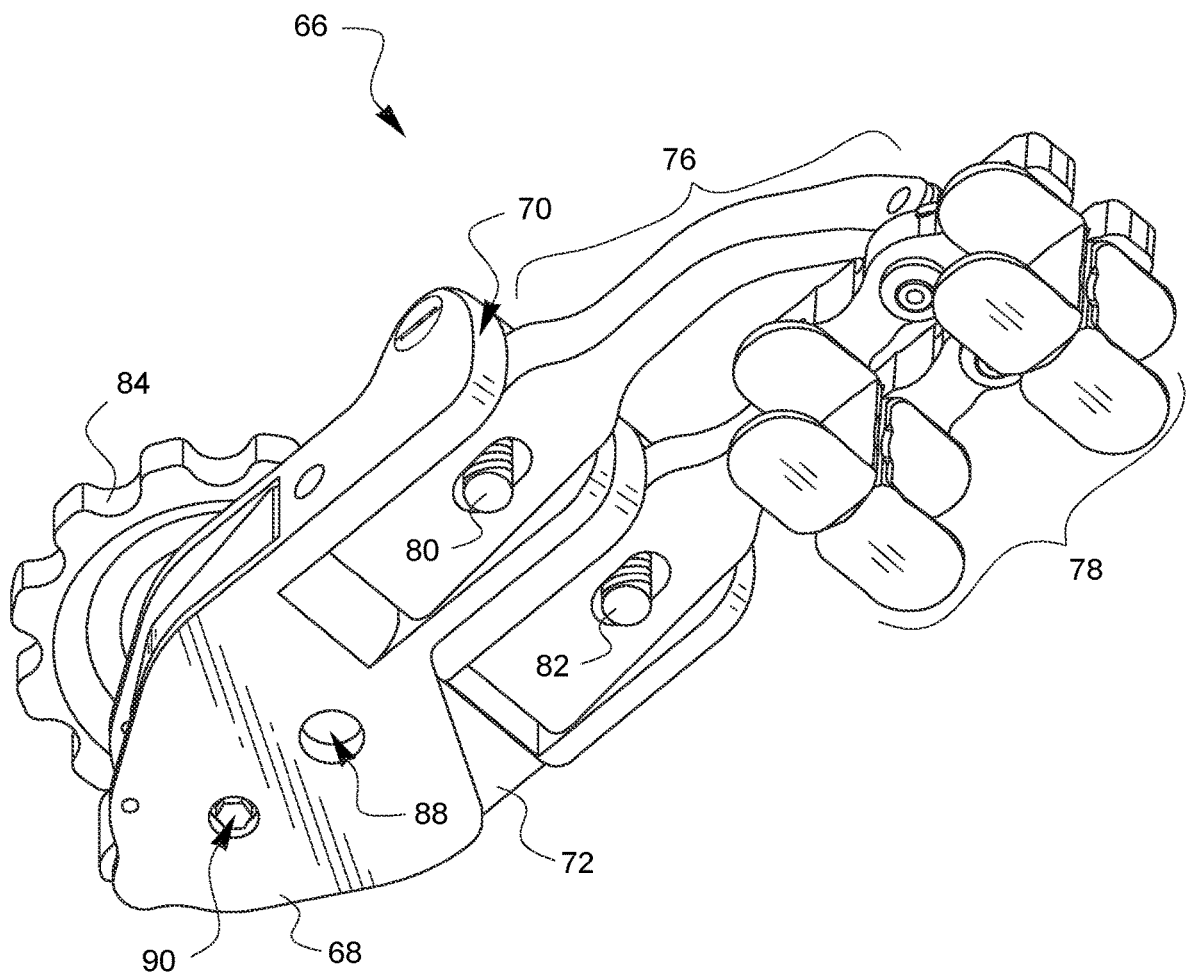
FIG. 1B is a front-bottom-left perspective view of the surgical rib retractor embodiment of FIG. 1A.

FIG. 1B is a front-bottom-left perspective view of the surgical rib retractor embodiment of FIG. 1A. In the view of FIG. 1B, the bottom side of the first and second arm actuators 80, 82 may be seen. The pivot point 88 between the housing 68 and the body 72 is visible, as is the bottom 90 of the drive actuator 84. It should be noted that in this embodiment, the bottom 90 of the drive actuator 84 comprises an actuation key configured to engage at least one of the first and second arm actuators 80, 82 (in this case, from the top side shown in FIG. 1A) for rotation by first removing the drive actuator 84 from the position shown in FIGS. 1A, 1B and then placing the bottom/actuation key 90 into a matching feature on either of the first or second arm actuators 80, 82.

FIGS. 2A, 2B, 2C, 2D, 2E, 2F are top, left, right, bottom, rear, and front elevational views of the surgical rib retractor embodiment of FIG. 1A.

Figure 3A:
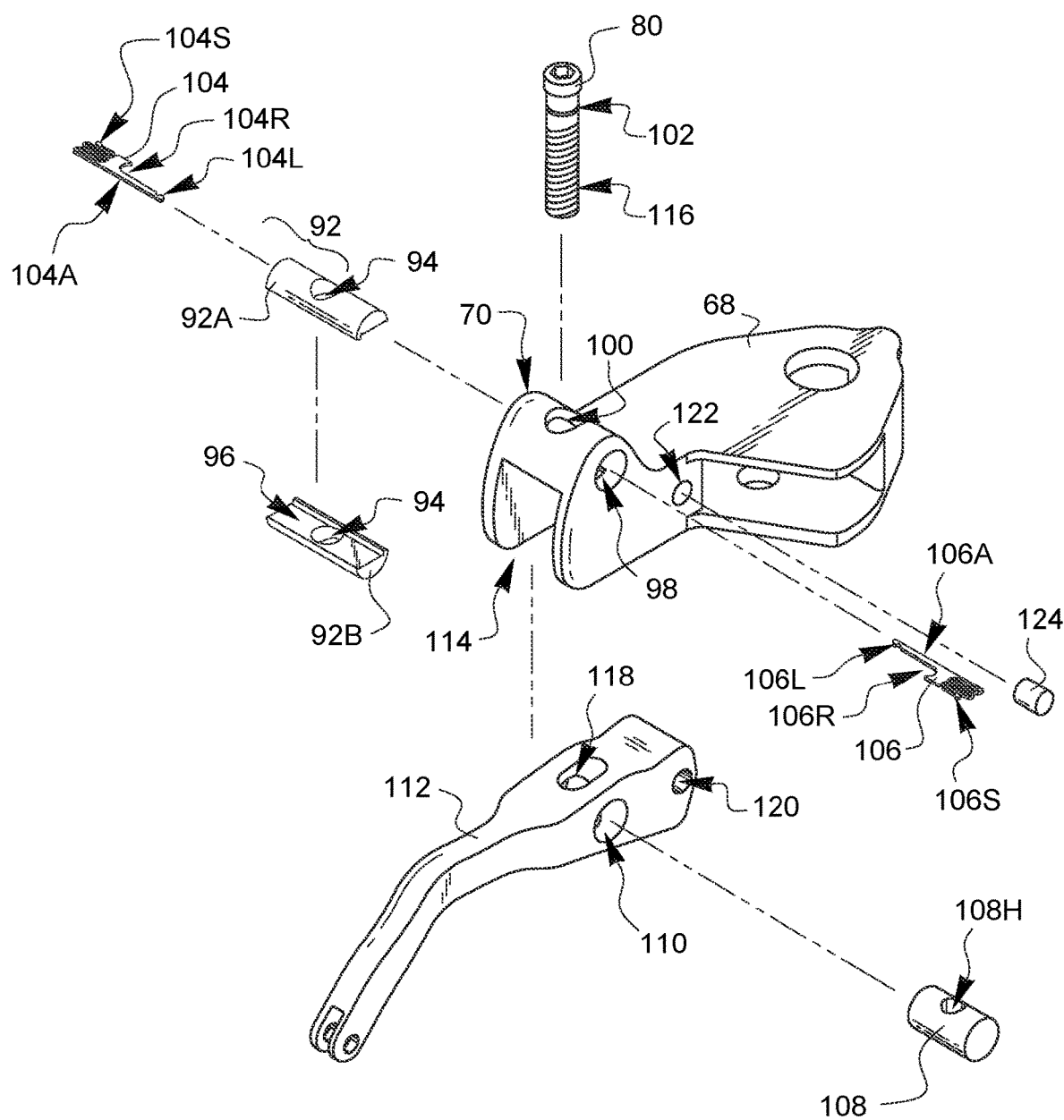
FIGS. 3A-3D are exploded perspective views of different portions of the surgical rib retractor embodiment of FIG. 1A.

FIGS. 3A-3D are exploded perspective views of different portions of the surgical rib retractor embodiment of FIG. 1A. As shown in FIG. 3A, a first pivoting constraint 92 has halves 92A, 92B which may be brought together to form a cylinder having a clearance hole 94 that passes through the rounded sides of the cylinder and a slot 96 which passes through the flat ends of the cylinder. When the halves 92A, 92B are brought together to form a cylinder, the first pivoting constraint 92 may be placed into a corresponding constraint hole 98 in the shoulder 70 of the housing 68. The first arm actuator 80 can be passed down through an upper opening 100 in the shoulder 70 of the housing 68, and then passed through the clearance hole 94 until a groove 102 is lined up with the slot 96 in the first pivoting constraint 92. Clips 104, 106 are then inserted into opposite ends of the slot 96. Clip 104 has a holding arm 104A, a receiver 104R, a spring element 104S, and a spring receiver latch 104L. Similarly, clip 106 has a holding arm 106A, a receiver 106R, a spring element 106S, and a spring receiver latch 106L. As the clips 104, 106 are inserted into opposite ends of the slot 96, the receivers 104R, 106R will come to rest in the groove 102 of the first arm actuator 80. A portion of each holding arm 104A, 106A will also rest in the groove 102 of the first arm actuator 80. The spring element 104S will be compressed slightly by the arm 106A and then come to rest in the spring receiver latch 106L at substantially the same time that the spring element 106S is compressed slightly by the arm 104A and then is held by the spring receiver latch 104L. The first arm actuator 80 is free to rotate within the combined clip formed by clips 104, 106, and therefore, it is constrained to be rotatable relative to the first shoulder 70.

A pivotable receiver 108 having a threaded hole 108H is placed into a matching hole 110 in a first arm 112. The first arm 112 is brought up into an opening 114 in the first shoulder 70 such that threads 116 on the first arm actuator 80 which are now protruding down into the opening 114 pass through a slot 118 and align with the threaded hole 108H of the receiver 108 in the first arm 112. The first arm actuator 80 is rotated to thread the threaded hole 108H, drawing the arm 112 up into the shoulder 70. A hole 120, which is located to define a desired pivot point for the arm 112, is aligned with a corresponding hole 122, and then an axle 124 is inserted to maintain the alignment between the holes 120, 122.

Figure 3B:
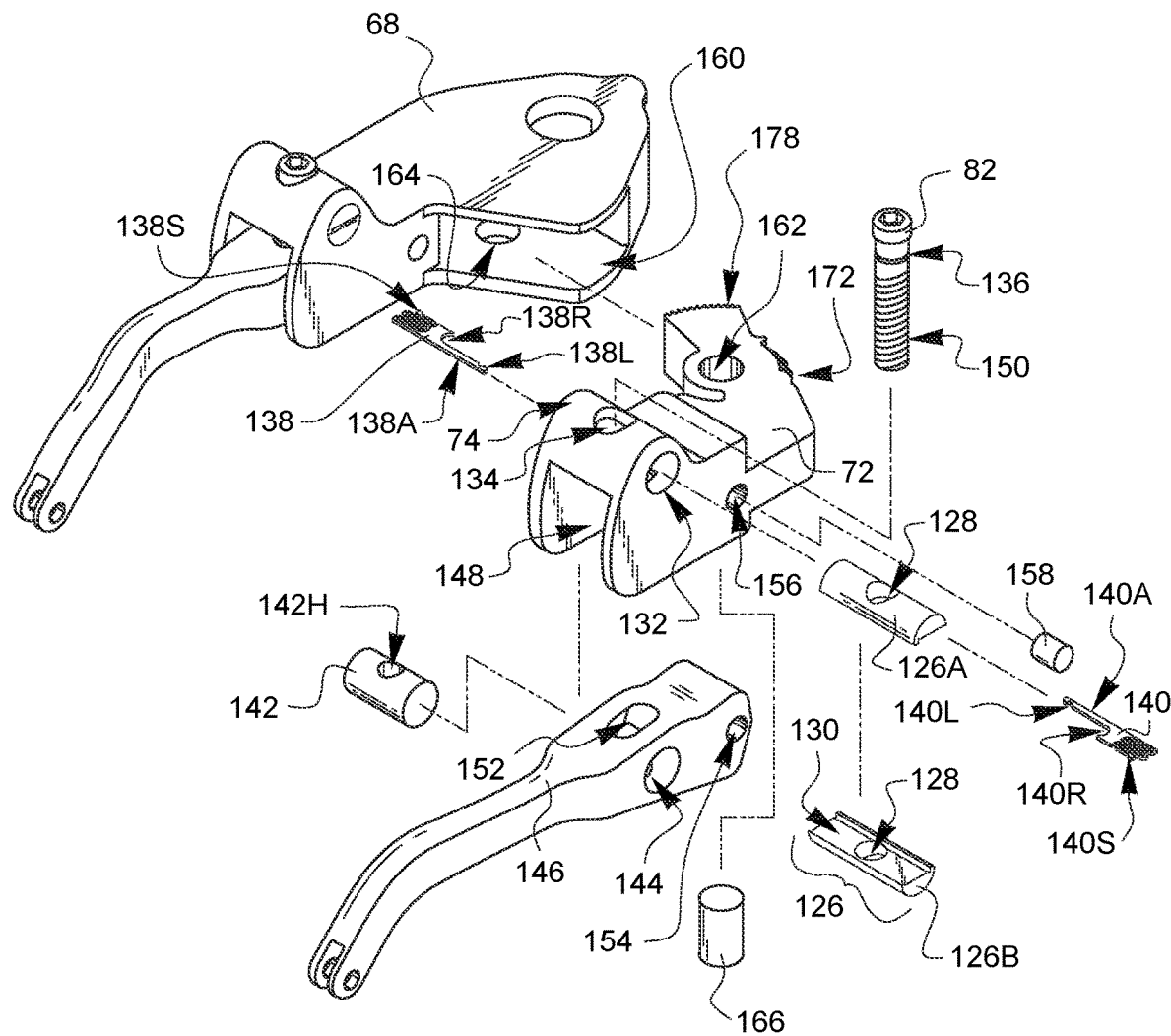

As shown in FIG. 3B, a second pivoting constraint 126 has halves 126A, 126B which may be brought together to form a cylinder having a clearance hole 128 that passes through the rounded sides of the cylinder and a slot 130 which passes through the flat ends of the cylinder. When the halves 126A, 126B are brought together to form a cylinder, the second pivoting constraint 126 may be placed into a corresponding constraint hole 132 in the shoulder 74 of the body 72. The second arm actuator 82 can be passed down through an upper opening 134 in the shoulder 74 of the body 72, and then passed through the clearance hole 128 until a groove 136 is lined up with the slot 130 in the second pivoting constraint 126. Clips 138, 140 are then inserted into opposite ends of the slot 130. Clip 138 has a holding arm 138A, a receiver 138R, a spring element 138S, and a spring receiver latch 138L. Similarly, clip 140 has a holding arm 140A, a receiver 140R, a spring element 140S, and a spring receiver latch 140L. As the clips 138, 140 are inserted into opposite ends of the slot 130, the receivers 138R, 140R will come to rest in the groove 136 of the second arm actuator 82. A portion of each holding arm 138A, 140A will also rest in the groove 136 of the second arm actuator 82. The spring element 138S will be compressed slightly by the arm 140A and then come to rest in the spring receiver latch 140L at substantially the same time that the spring element 140S is compressed slightly by the arm 138A and then is held by the spring receiver latch 138L. The second arm actuator 82 is free to rotate within the combined clip formed by clips 138, 140, and therefore, it is constrained to be rotatable relative to the second shoulder 74.

A pivotable receiver 142 having a threaded hole 142H is placed into a matching hole 144 in a second arm 146. The second arm 146 is brought up into an opening 148 in the second shoulder 74 such that threads 150 on the second arm actuator 82 which are now protruding down into the opening 148 pass through a slot 152 and align with the threaded hole 142H of the receiver 142 in the second arm 146. The second arm actuator 82 is rotated to thread into the threaded hole 142H, drawing the arm 146 up into the shoulder 74. A hole 154, which is located to define a desired pivot point for the arm 146, is aligned with a corresponding hole 156, and then an axle 158 is inserted to maintain the alignment between the holes 154, 156.

The body 72 is inserted into an opening 160 in the housing 68 so that a hole 162 in the body 72, defining a pivot axis, is aligned with a corresponding hole 164 in the housing 68. An axle 166 passes through the holes 162, 164 to pivotally couple the body 72 to the housing 68.

Figure 3C:
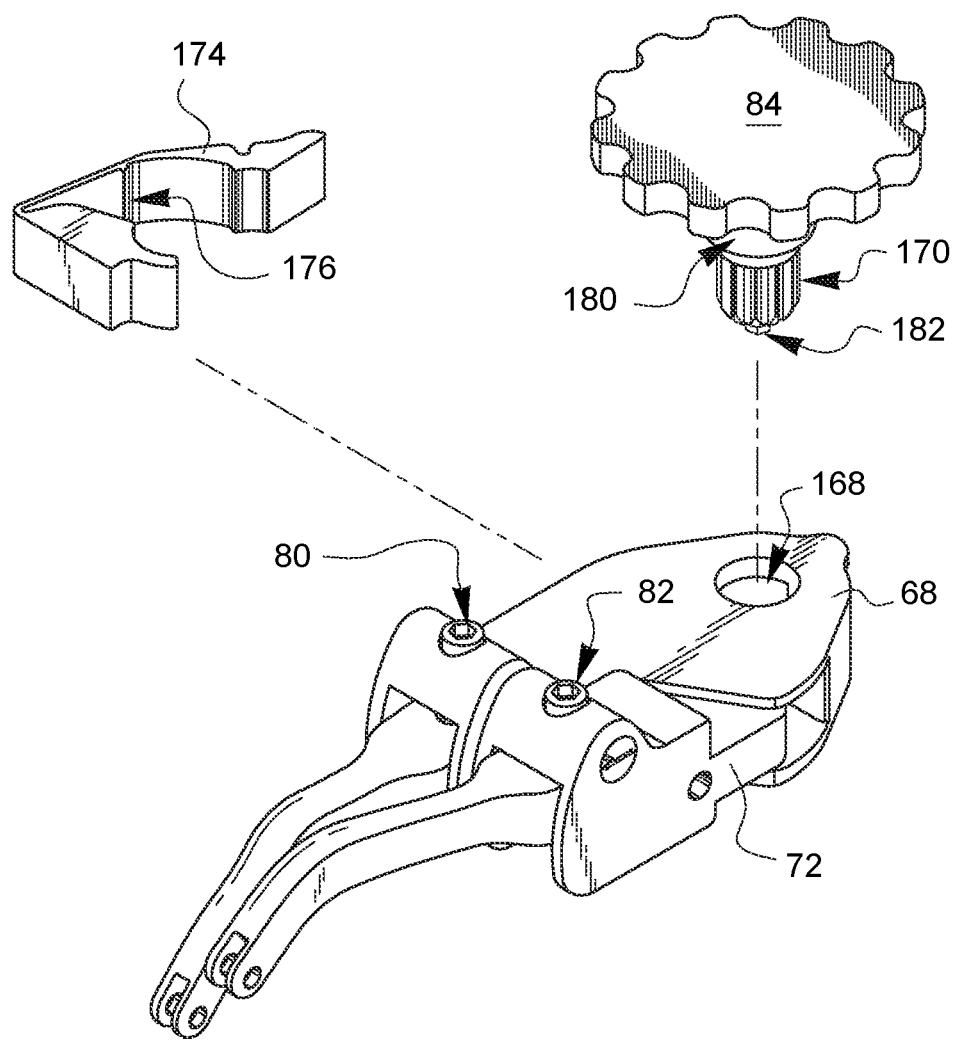

As shown in FIG. 3C, the housing 68 defines an actuator guide opening 168. The drive actuator 84 has an actuation gear 170. The actuation gear 170 is placed through the actuator guide opening (which is sized to accept the actuation gear) so that the actuation gear 170 is in alignment with a drive gear 172 (not shown in this view, but visible in FIG. 3B), which is part of the body 72. As shown in FIG. 3C, a pawl arm 174 is installed between the housing 68 and the body 72. The pawl arm 174 has a pawl 176 which is biased against a ratchet gear 178 (not shown in this view, but visible in FIG. 3B), which is part of the body 72. As shown in FIG. 3C, the drive actuator 84 has a pawl arm deflection portion 180 that is configured to engage the pawl arm 174 when the drive actuator 84 is pushed down, thereby releasing the pawl 176 from the ratchet gear 178 when desired. In this embodiment, the drive actuator 84 is removable from the device, so the drive actuator 84 can be used to rotate the actuation gear 170 in contact with the drive gear 172, while the pawl 176 and ratchet gear 178 prevent the actuation gear 170 (and therefore the body 72) from rotating backwards. The drive actuator 84 can be removed and/or later pushed farther in to defeat the pawl 176, allowing the actuation gear 170 (and therefore the body 72) to rotate back. The drive actuator 84 may also have an actuation key 182 configured to engage at least one of the first and second arm actuators 80, 82 when the drive actuator 84 has been removed from the actuator guide opening 168.

Figure 3D:
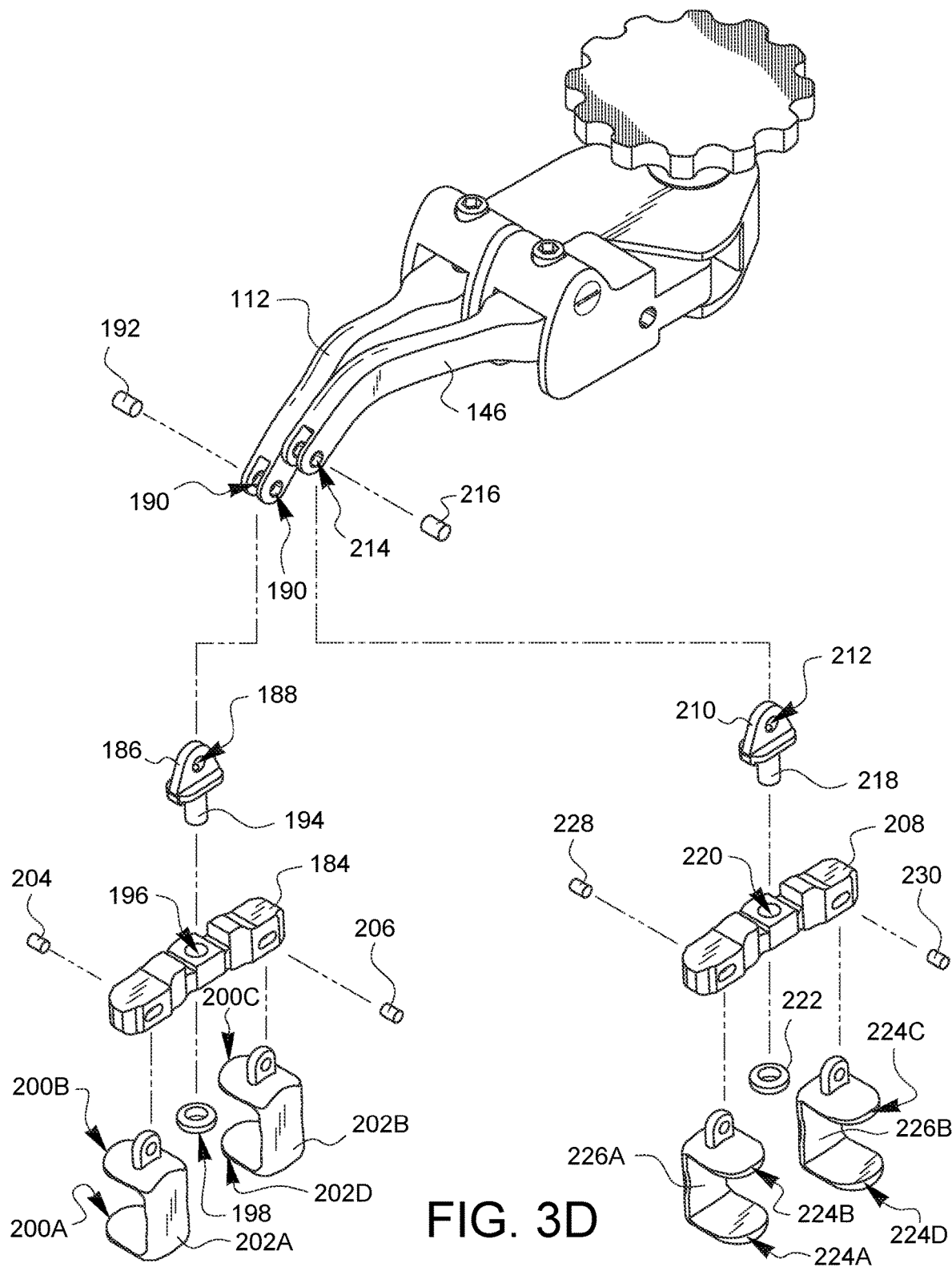

The first arm unit 76 of FIG. 1 comprises a first arm 112 (previously discussed with regard to FIG. 3A) and a first strut 184, as shown in the partially exploded view of FIG. 3D. In this embodiment, the first strut 184 is pivotably coupled to the first arm 112 by a first adapter 186 having a hole 188 that is held in alignment with holes 190 in first arm 112 by axle 192. A post 194 on adapter 186 passes through a corresponding hole 196 in the first strut 184, which is then held onto the post 194 by ring/cap 198 that is attached to the post 194. In this embodiment, the adapter 186 allows the strut 184 to pivot with two degrees of freedom (on axle 192 and on post 194) relative to the arm 112. In other embodiments, the strut 184 may have more or fewer degrees of freedom relative to the arm 112. In some embodiments, the strut 184 may be continuously formed with the arm 112. Depending on the embodiment, the strut 184 may be inflexible or flexible.

In this embodiment, the first strut 184 also comprises one or more rib engaging fingers, such as rib engaging fingers 200A, 200B, 200C, 200D. In this embodiment, rib engaging fingers 200A, 200B form a first opposing pair of rib engaging fingers 202A, while rib engaging fingers 200C, 200D form a second opposing pair of rib engaging fingers 202B. The rib engaging fingers are configured to be placed around or adjacent to a rib for pulling and/or pushing on the rib. Depending on the embodiment, the rib engaging fingers may be covered with a softer covering to provide protection for the ribs. In this embodiment, the first opposing pair of rib engaging fingers 202A is coupled to the first strut 184 by a pin 204, while the second opposing pair of rib engaging fingers 202B is coupled to the first strut 184 by a pin 206. In this embodiment, the pins 204, 206 have some freedom of movement to pivot and/or slide, which may help the rib engaging fingers to be placed around a rib during a surgical procedure. Other embodiments may have more or fewer rib engaging fingers.

The second arm unit 78 of FIG. 1 comprises a second arm 146 (previously discussed with regard to FIG. 3B) and a second strut 208, as shown in the partially exploded view of FIG. 3D. In this embodiment, the second strut 208 is pivotably coupled to the second arm 146 by a second adapter 210 having a hole 212 that is held in alignment with holes 214 in second arm 146 by axle 216. A post 218 on adapter 210 passes through a corresponding hole 220 in the second strut 208, which is then held onto the post 218 by ring/cap 222 that is attached to the post 218. In this embodiment, the adapter 210 allows the strut 208 to pivot with two degrees of freedom (on axle 216 and on post 218) relative to the arm 146. In other embodiments, the strut 208 may have more or fewer degrees of freedom relative to the arm 146. In some embodiments, the strut 208 may be continuously formed with the arm 146. Depending on the embodiment, the strut 208 may be inflexible or flexible.

In this embodiment, the second strut 208 also comprises one or more rib engaging fingers, such as rib engaging fingers 224A, 224B, 224C, 224D. In this embodiment, rib engaging fingers 224A, 224B form a third opposing pair of rib engaging fingers 226A, while rib engaging fingers 224C, 224D form a fourth opposing pair of rib engaging fingers 226B. The rib engaging fingers are configured to be placed around or adjacent to a rib for pulling and/or pushing on the rib. Depending on the embodiment, the rib engaging fingers may be covered with a softer covering to provide protection for the ribs. In this embodiment, the third opposing pair of rib engaging fingers 226A is coupled to the second strut 208 by a pin 228, while the fourth opposing pair of rib engaging fingers 226B is coupled to the second strut 208 by a pin 230. In this embodiment, the pins 228, 230 have some freedom of movement to pivot and/or slide, which may help the rib engaging fingers to be placed around a rib during a surgical procedure. Other embodiments may have more or fewer rib engaging fingers.

Figure 4:
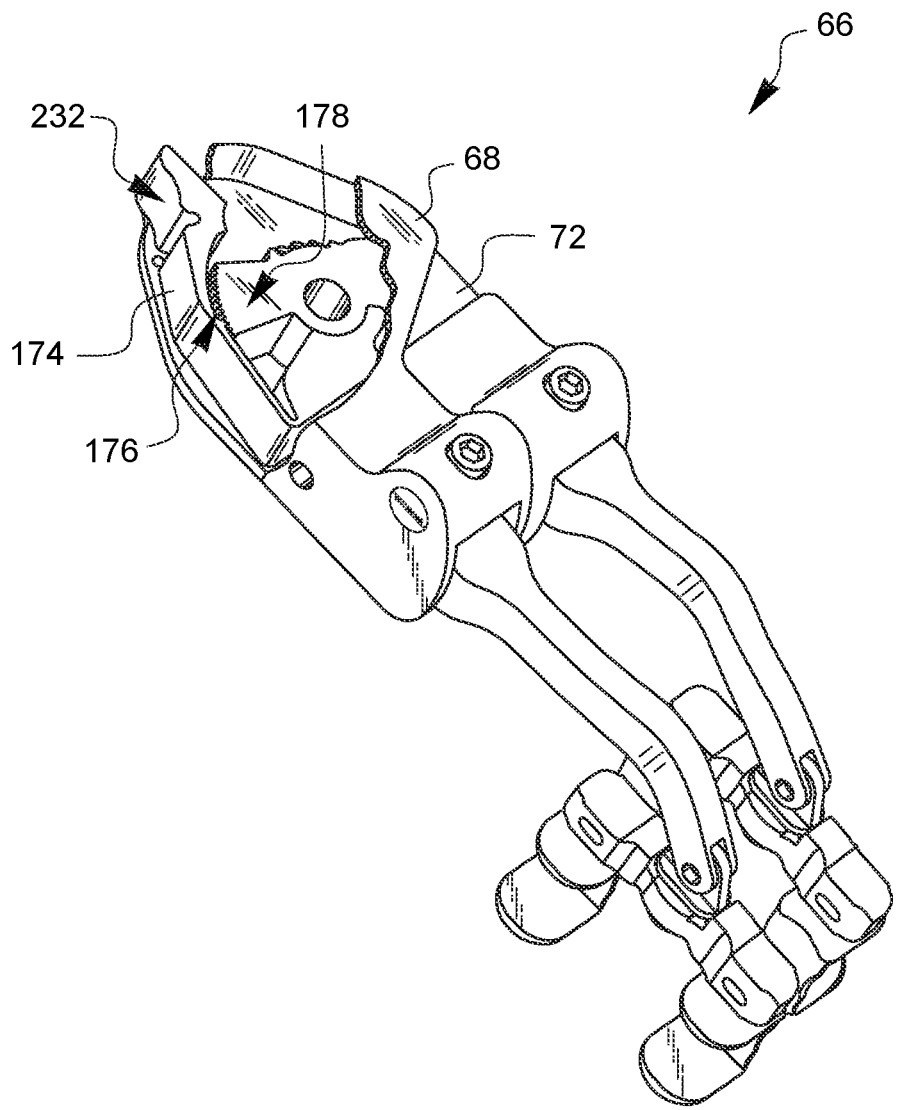
FIG. 4 has the drive actuator knob removed and is a partially exposed perspective view of the surgical rib retractor embodiment of FIG. 1A so that a ratchet mechanism and a drive gear are visible.

FIG. 4 is a perspective view of the surgical rib retractor 66 of FIGS. 1-3D. The drive actuator knob has been removed and a portion of the housing 68 is shown removed in order to partially expose the ratchet gear 178 as it interacts with the pawl 176 mechanism and a drive gear are visible. The pawl arm 174 has a release tab 232 which can be pulled to disengage the pawl 176 from the ratchet gear 178.

Figure 5:
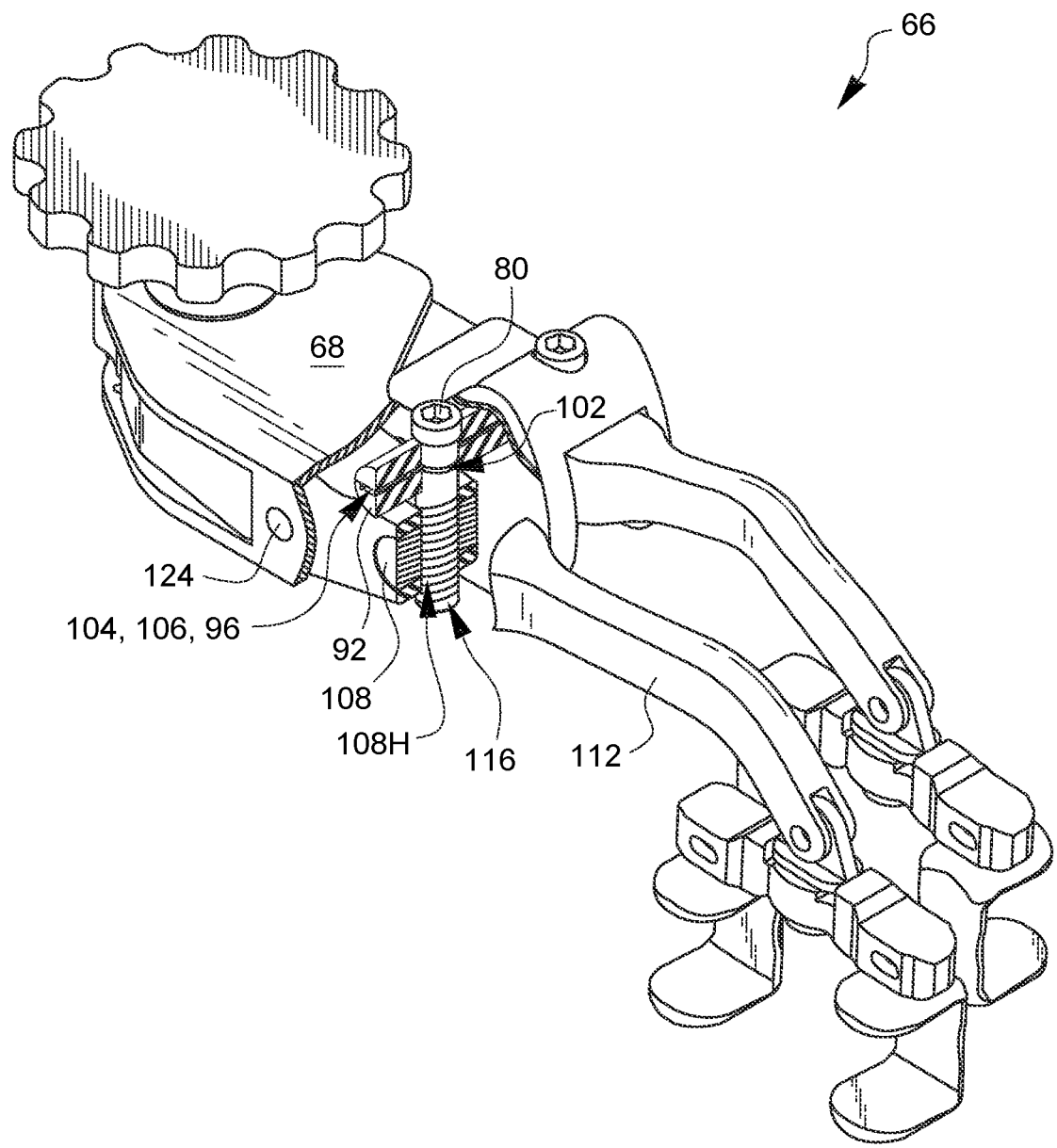
FIG. 5 is a partially sectioned and exposed perspective view of the surgical rib retractor embodiment of FIG. 1A so that one of the arm actuators can be seen more clearly.

FIG. 5 is a partially sectioned and exposed perspective view of the surgical rib retractor 66 embodiment of FIG. 1A so that one of the arm actuators 80 can be seen more clearly. As described in the previous exploded views, the arm actuator 80 passes down through an upper opening in the shoulder (the shoulder is hidden in this exposed view) of the housing 68, and then passed through the clearance hole in the first pivoting constraint 92 until a groove 102 is lined up with and held by the clips 104, 106 held in the slot 96. The first arm actuator 80 is free to rotate within the combined clip formed by clips 104, 106, and therefore, it is constrained to be rotatable relative to the first shoulder. The threads 116 of the first arm actuator 80 engage a threaded hole 108H in a pivotable receiver 108. The arm 112 is pivotably pinned to the housing 68 by an axle 124, and the arm 112 may be pivoted up or down by turning the arm actuator 80 in different directions. The other arm assembly and arm actuator work similarly.

Figure 6A:
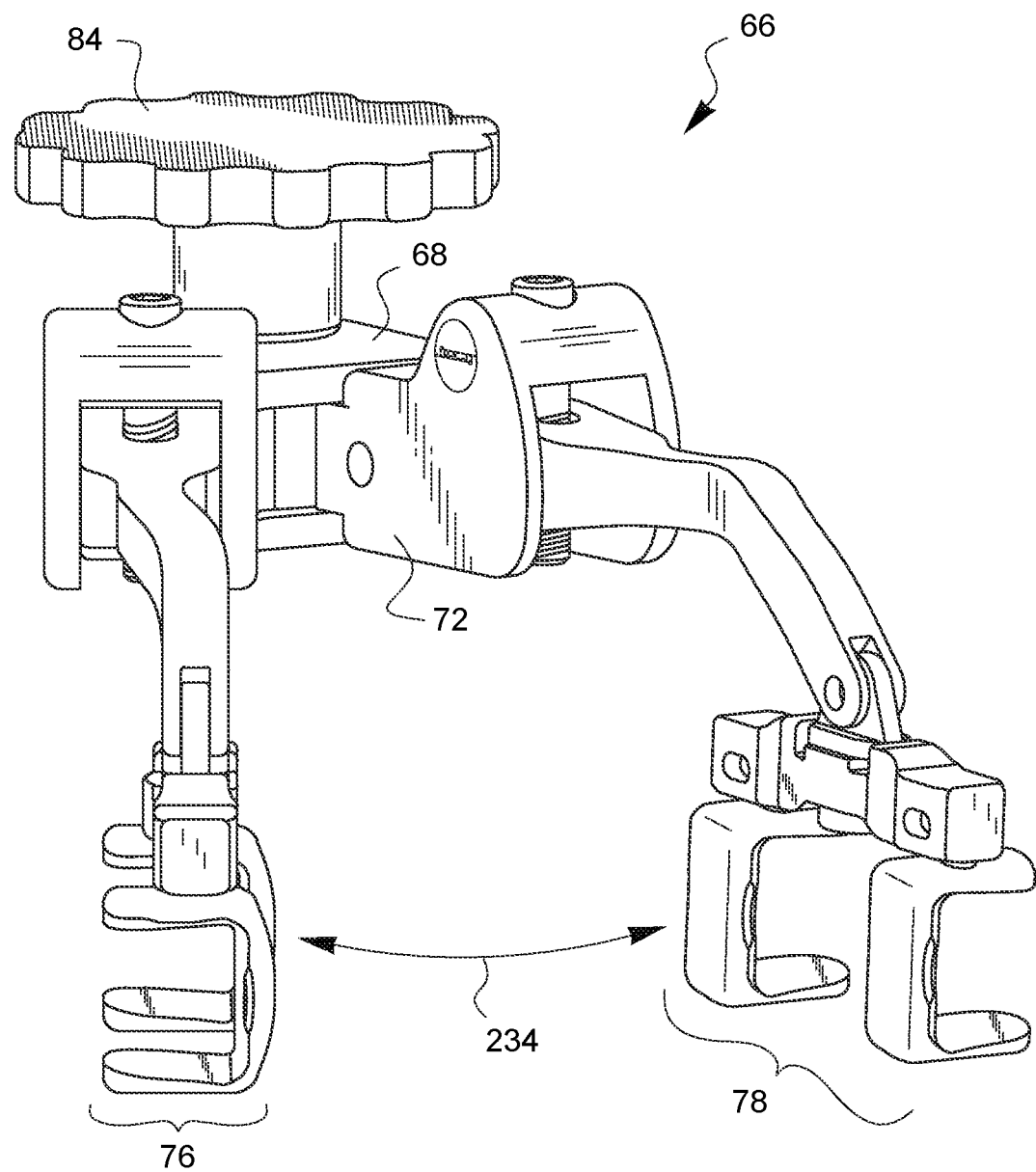
FIG. 6A is a perspective view of the surgical rib retractor embodiment of FIG. 1A with the body having moved with respect to the housing to create relative movement between the first and second arm units in a first plane.

FIG. 6A is a perspective view of the surgical rib retractor 66 embodiment of FIG. 1A with the body 72 having moved with respect to the housing 68 to create relative movement between the first and second arm units 76, 78 in a first plane 234. This movement is caused by turning the drive actuator 84 to engage the drive gear (not visible in this view).

Figure 6B:
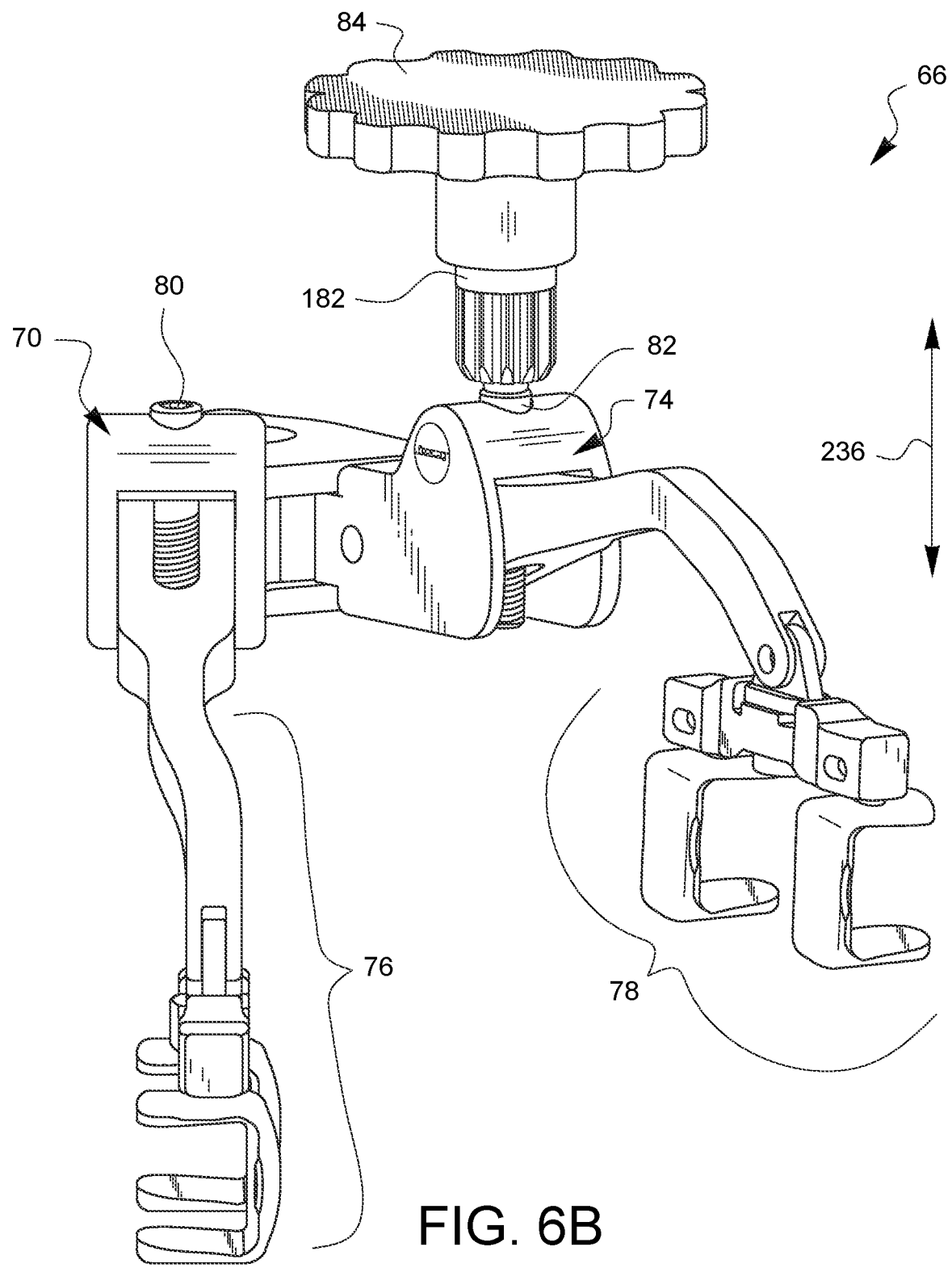
FIG. 6B is a perspective view of the surgical rib retractor of FIG. 6A with the first arm unit having pivoted down (with respect to the first shoulder) and the second arm unit having pivoted up (with respect to the second shoulder) to create a final relative movement between the two arm units that includes at least two directional components.

FIG. 6B is a perspective view of the surgical rib retractor 66 of FIG. 6A with the first arm unit 76 having pivoted down (with respect to the first shoulder 70) and the second arm unit 78 having pivoted up (with respect to the second shoulder 74) to create a final relative movement between the two arm units 76, 78 that includes at least two directional components. The first directional component came from the movement of FIG. 6A. The second directional component 236 came from the movement of FIG. 6B which is a separation in a direction that is substantially perpendicular to the plane 234 of FIG. 6A. The movement in FIG. 6B is caused by rotating the arm actuators 80, 82, in this case by using the actuation key 182 on the bottom of the drive actuator 84.

Figure 7A:
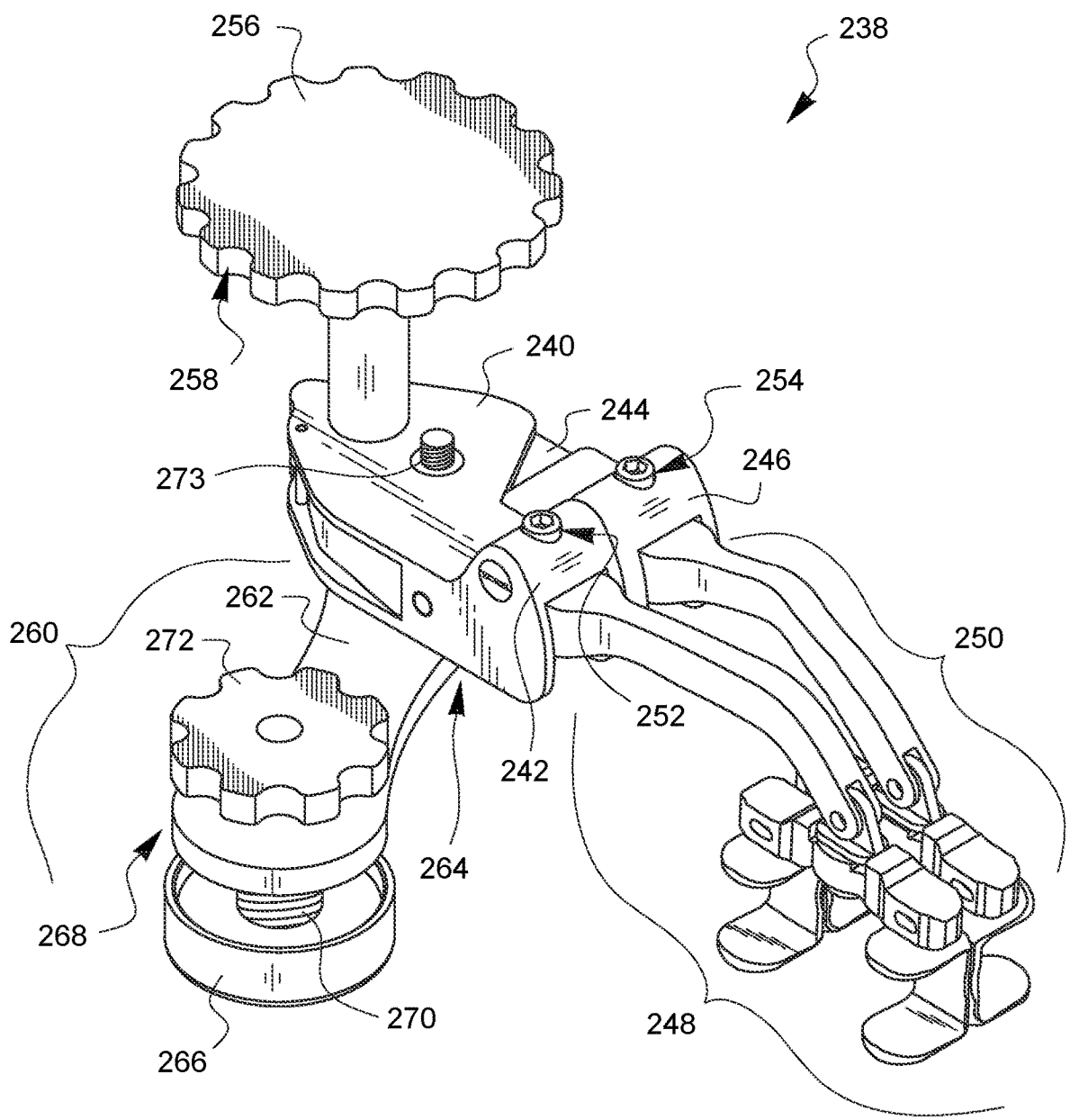
FIG. 7A is a front-top-left perspective view of an embodiment of a surgical rib retractor having an embodiment of an anti-cant feature.

FIG. 7A is a front-top-left perspective view of another embodiment of a surgical rib retractor 238. The retractor 238 has a housing 240. The housing 240 has a first shoulder 242. The retractor 238 also has a body 244 pivotably coupled to the housing 240 and having a second shoulder 246. The surgical rib retractor 238 also has a first arm unit 248 pivotably coupled to the first shoulder 242 and configured to receive one rib. The surgical rib retractor 238 also has a second arm unit 250 pivotably coupled to the second shoulder 246 and configured to receive another rib.

The surgical rib retractor 238 has a first arm actuator 252 constrained to be rotatable relative to the first shoulder 242 and coupled to the first arm unit 248 to pivot the first arm unit 248 as the first arm actuator 252 is rotated. Similarly, the retractor 238 also has a second arm actuator 254 constrained to be rotatable relative to the second shoulder 246 and coupled to the second arm unit 250 to pivot the second arm unit 250 as the second arm actuator 254 is rotated.

The surgical rib retractor 238 also has a drive actuator 256. The drive actuator 256 is configured to pivot the body 244 relative to the housing 240. In this embodiment, the drive actuator 256 includes a knob 258 and a gear (not visible in this view). In other embodiments, the drive actuator could comprise a variety of elements, including one or more gears, one or more knobs, one or more levers, one or more pulleys, one or more motors, one or more solenoids, or any combination thereof.

The surgical rib retractor 238 also has an anti-cant feature 260 comprising a lever arm 262 which is coupled to the housing 240. In this embodiment, the lever arm 262 is pivotably coupled to the housing 240 at a proximal end 264 of the lever arm 262 so that the lever arm 262 may be positioned on either side of the housing 240. A footing 266 is coupled to distal end 268 and is configured to contact a patient's chest, enabling the lever arm 262 to resist any tendency of the retractor 238 to tip or cant in one direction as the retractor arm units 248, 250 are moved to retract ribs that may be held therein. In this embodiment, the footing 266 is coupled to the lever arm 262 by a threaded post 270. The threaded post 270 is coupled to a footing adjustment knob 272 which can be rotated in a desired direction to raise or lower the footing 266.

The embodiment of FIG. 7A also has an accessory connection point 273, upon which one or more surgical accessories may be mounted. In this embodiment, the accessory connection point 273 is a threaded post, but other embodiments may have an accessory connection point of a different design, such as, but not limited to a threaded recess, a keyed protrusion, a keyed recess, a snap fitting, a post with a hole, a post, or any combination and/or plurality thereof. One non-limiting example of a surgical accessory which might be configured to couple to the accessory connection point 273 is a suture management device for keeping multiple sets of sutures separated and organized in a meaningful order.

Figure 7B:
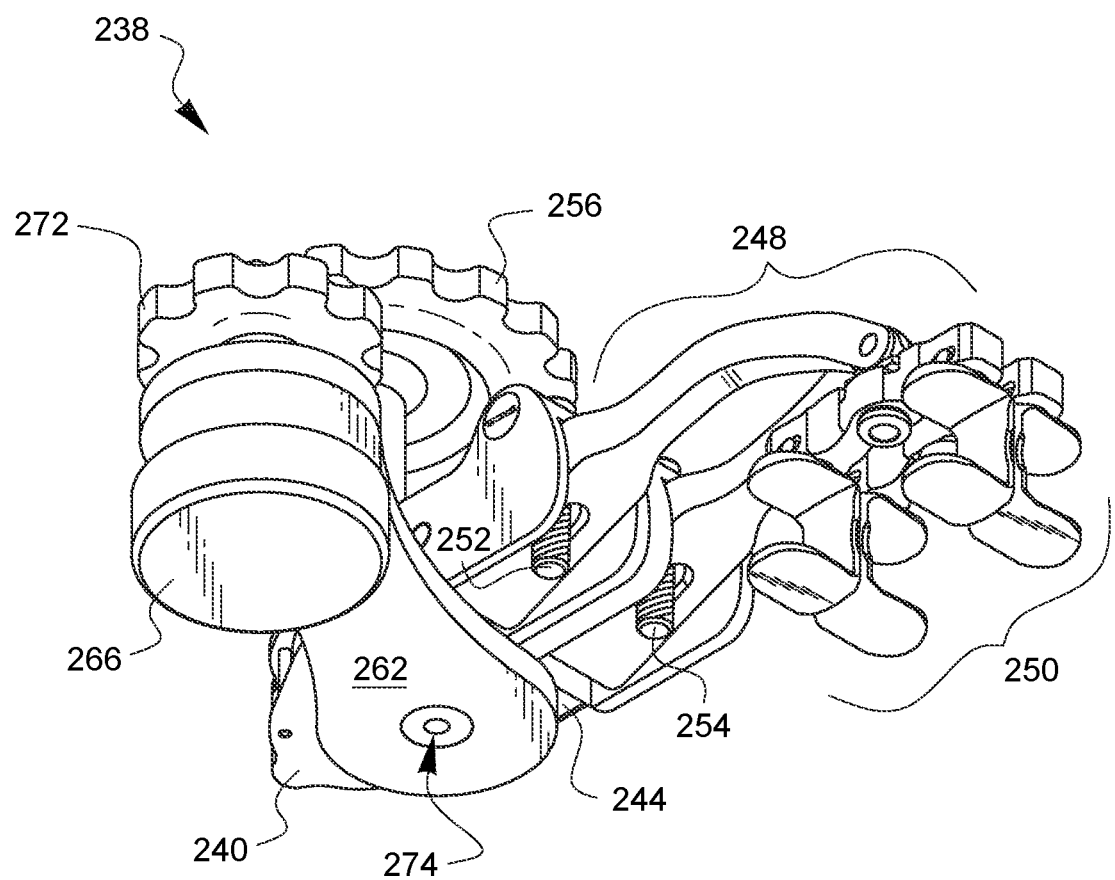
FIG. 7B is a front-bottom-left perspective view of the surgical rib retractor embodiment of FIG. 7A.

FIG. 7B is a front-bottom-left perspective view of the surgical rib retractor 238 embodiment of FIG. 7A. In the view of FIG. 7B, the bottom side of the first and second arm actuators 252, 254 may be seen. A pivot point 274 between the housing 240 and the body 72 is visible. Although it is not visible in this view, the bottom of the drive actuator 256 comprises an actuation key (similar to previous embodiments) configured to engage at least one of the first and second arm actuators 252, 254 (in this case, from the top side shown in FIG. 7A) for rotation by first removing the drive actuator 256 from the position shown in FIGS. 7A, 7B and then placing the bottom/actuation key into a matching feature on either of the first or second arm actuators 252, 254.

Figure 8A:
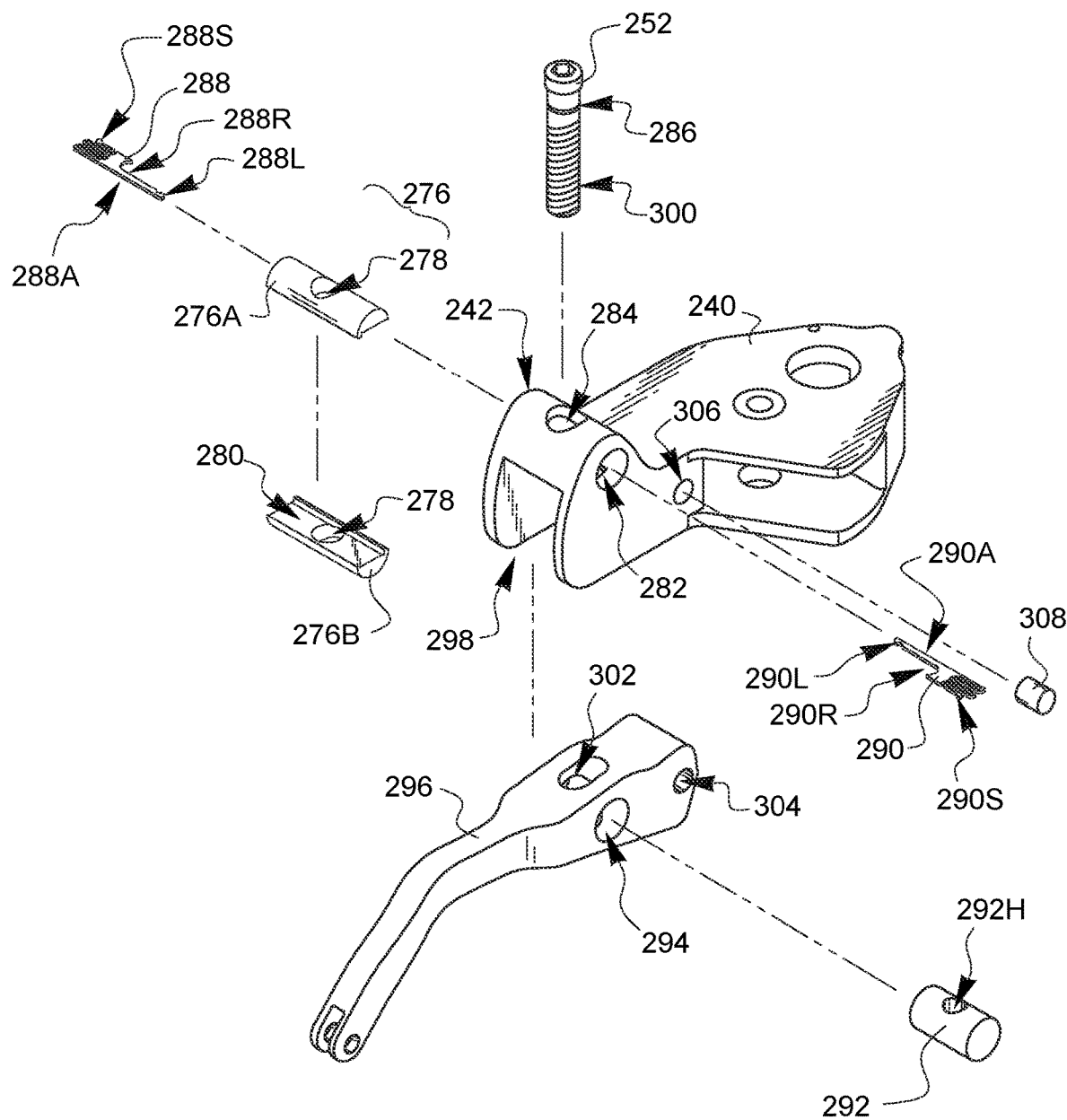
FIGS. 8A-8E are exploded perspective views of different portions of the surgical rib retractor embodiment of FIG. 7A.

FIGS. 8A-8E are exploded perspective views of different portions of the surgical rib retractor embodiment of FIG. 7A. As shown in FIG. 8A, a first pivoting constraint 276 has halves 276A, 276B which may be brought together to form a cylinder having a clearance hole 278 that passes through the rounded sides of the cylinder and a slot 280 which passes through the flat ends of the cylinder. When the halves 276A, 276B are brought together to form a cylinder, the first pivoting constraint 276 may be placed into a corresponding constraint hole 282 in the shoulder 242 of the housing 240. The first arm actuator 252 can be passed down through an upper opening 284 in the shoulder 242 of the housing 240, and then passed through the clearance hole 278 until a groove 286 is lined up with the slot 280 in the first pivoting constraint 276. Clips 288, 290 are then inserted into opposite ends of the slot 280. Clip 288 has a holding arm 288A, a receiver 288R, a spring element 288S, and a spring receiver latch 288L. Similarly, clip 290 has a holding arm 290A, a receiver 290R, a spring element 290S, and a spring receiver latch 290L. As the clips 288, 290 are inserted into opposite ends of the slot 280, the receivers 288R, 290R will come to rest in the groove 286 of the first arm actuator 252. A portion of each holding arm 288A, 290A will also rest in the groove 286 of the first arm actuator 252. The spring element 288S will be compressed slightly by the arm 290A and then come to rest in the spring receiver latch 290L at substantially the same time that the spring element 290S is compressed slightly by the arm 288A and then is held by the spring receiver latch 288L. The first arm actuator 252 is free to rotate within the combined clip formed by clips 288, 290, and therefore, it is constrained to be rotatable relative to the first shoulder 242.

A pivotable receiver 292 having a threaded hole 292H is placed into a matching hole 294 in a first arm 296. The first arm 296 is brought up into an opening 298 in the first shoulder 242 such that threads 300 on the first arm actuator 252 which are now protruding down into the opening 298 pass through a slot 302 and align with the threaded hole 292H of the receiver 292 in the first arm 296. The first arm actuator 252 is rotated to thread into the threaded hole 292H, drawing the arm 296 up into the shoulder 242. A hole 304, which is located to define a desired pivot point for the arm 296, is aligned with a corresponding hole 306, and then an axle 308 is inserted to maintain the alignment between the holes 304, 306.

Figure 8B:
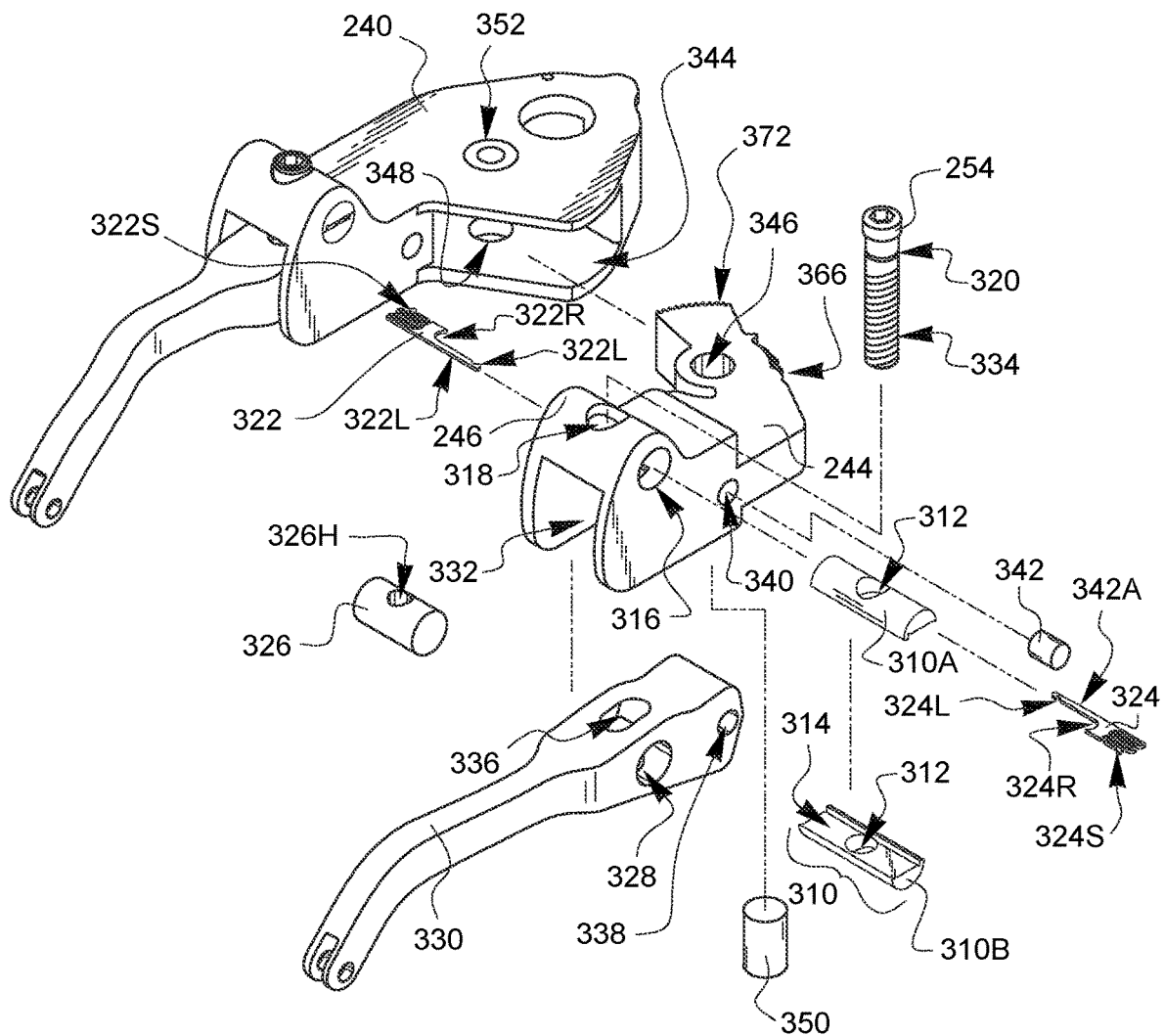

As shown in FIG. 8B, a second pivoting constraint 310 has halves 310A, 310B which may be brought together to form a cylinder having a clearance hole 312 that passes through the rounded sides of the cylinder and a slot 314 which passes through the flat ends of the cylinder. When the halves 310A, 310B are brought together to form a cylinder, the second pivoting constraint 310 may be placed into a corresponding constraint hole 316 in the shoulder 246 of the body 244. The second arm actuator 254 can be passed down through an upper opening 318 in the shoulder 246 of the body 244, and then passed through the clearance hole 312 until a groove 320 is lined up with the slot 314 in the second pivoting constraint 310. Clips 322, 324 are then inserted into opposite ends of the slot 314. Clip 322 has a holding arm 322A, a receiver 322R, a spring element 322S, and a spring receiver latch 322L. Similarly, clip 324 has a holding arm 324A, a receiver 324R, a spring element 324S, and a spring receiver latch 324L. As the clips 322, 324 are inserted into opposite ends of the slot 314, the receivers 322R, 324R will come to rest in the groove 320 of the second arm actuator 254. A portion of each holding arm 322A, 324A will also rest in the groove 320 of the second arm actuator 254. The spring element 322S will be compressed slightly by the arm 324A and then come to rest in the spring receiver latch 324L at substantially the same time that the spring element 324S is compressed slightly by the arm 322A and then is held by the spring receiver latch 322L. The second arm actuator 254 is free to rotate within the combined clip formed by clips 322, 324, and therefore, it is constrained to be rotatable relative to the second shoulder 246.

A pivotable receiver 326 having a threaded hole 326H is placed into a matching hole 328 in a second arm 330. The second arm 330 is brought up into an opening 332 in the second shoulder 246 such that threads 334 on the second arm actuator 254 which are now protruding down into the opening 332 pass through a slot 336 and align with the threaded hole 326H of the receiver 326 in the second arm 330. The second arm actuator 254 is rotated to thread into the threaded hole 326H, drawing the arm 330 up into the shoulder 246. A hole 338, which is located to define a desired pivot point for the arm 330, is aligned with a corresponding hole 340, and then an axle 342 is inserted to maintain the alignment between the holes 338, 340.

The body 244 is inserted into an opening 344 in the housing 240 so that a hole 346 in the body 244, defining a pivot axis, is aligned with a corresponding hole 348 in the housing 240. An axle 350 passes through the holes 348, 346 to pivotably couple the body 244 to the housing 240. This embodiment also has hole 352 in the housing 340 which is aligned with the axle 350. Although the axle 350 is shown generically in FIG. 8B, in some embodiments, the axle 350 may pass upwards through the hole 352 to act as an accessory connection point as previously described. The hole 352 may be threaded to accept threads (not shown) on the end of the axle 350.

Figure 8C:
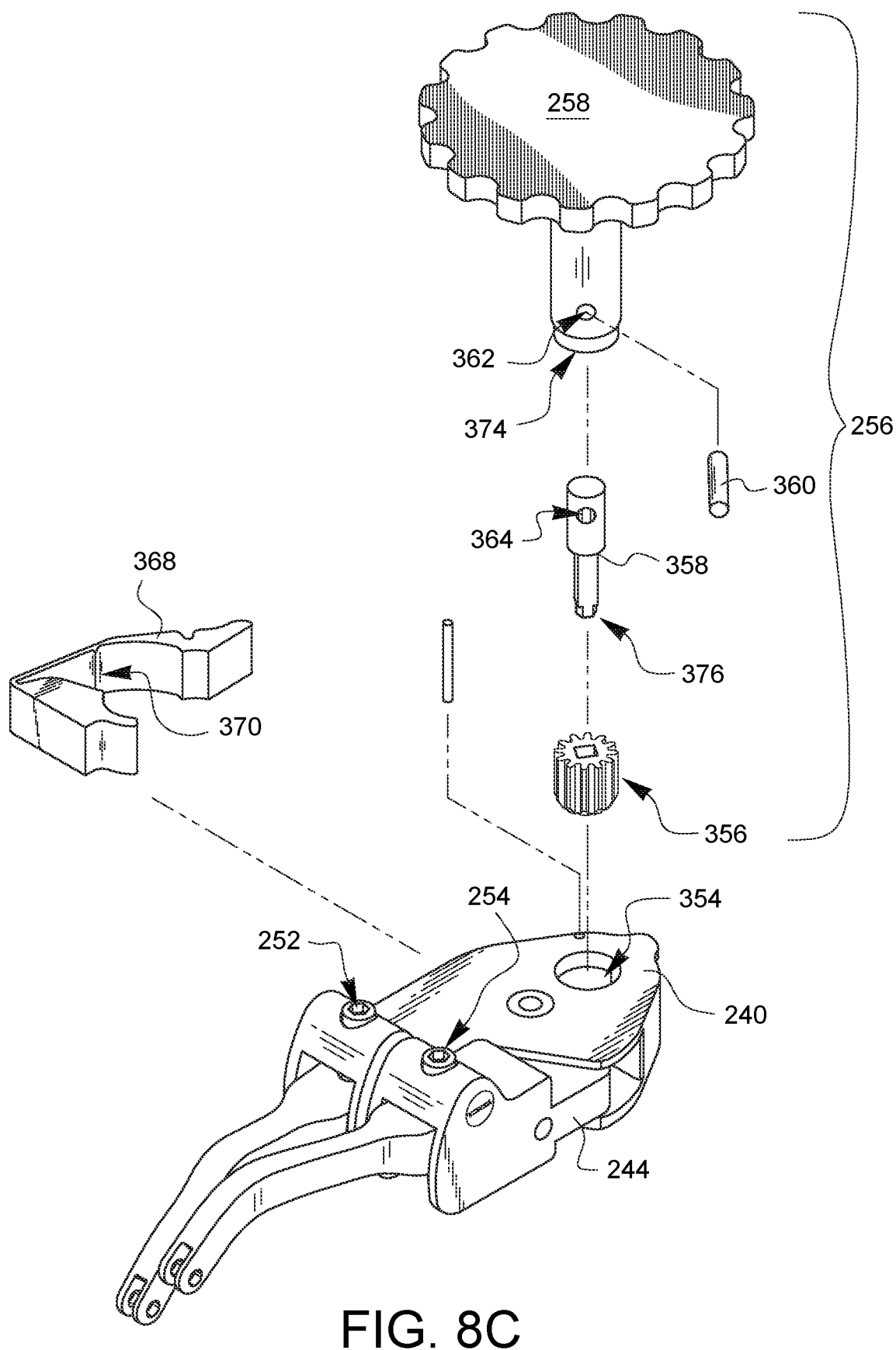

As shown in FIG. 8C, the housing 240 defines an actuator guide opening 354. The drive actuator 256 has an actuation gear 356 which is keyed to attach to an actuation key 358 that is pinned to the knob 258 by a pin 360 placed through holes 362, 364 in the knob 258 and actuation key 358, respectively. The actuation gear 356 is placed through the actuator guide opening 354 (which is sized to accept the actuation gear 356) so that the actuation gear 356 is in alignment with a drive gear 366 (not shown in this view, but visible in FIG. 7B), which is part of the body 244. As shown in FIG. 7C, a pawl arm 368 is installed between the housing 240 and the body 244. The pawl arm 368 has a pawl 370 which is biased against a ratchet gear 372 (not shown in this view, but visible in FIG. 7B), which is part of the body 244. As shown in FIG. 7C, the drive actuator 256 has a pawl arm deflection portion 374 that is configured to engage the pawl arm 368 when the drive actuator 256 is pushed down, thereby releasing the pawl 370 from the ratchet gear 372 when desired. In this embodiment, the drive actuator 256 is removable from the device, so the drive actuator 256 can be used to rotate the actuation gear 356 in contact with the drive gear 366, while the pawl 370 and ratchet gear 372 prevent the actuation gear 356 (and therefore the body 244) from rotating backwards. The drive actuator 256 can be removed and/or later pushed farther in to defeat the pawl 370, allowing the actuation gear 356 (and therefore the body 244) to rotate back. The actuation key 358 of the drive actuator 256 may also have a key 376 which protrudes past the actuation gear 356 and is configured to engage at least one of the first and second arm actuators 252, 254 when the drive actuator 256 has been removed from the actuator guide opening 354.

Figure 8D:
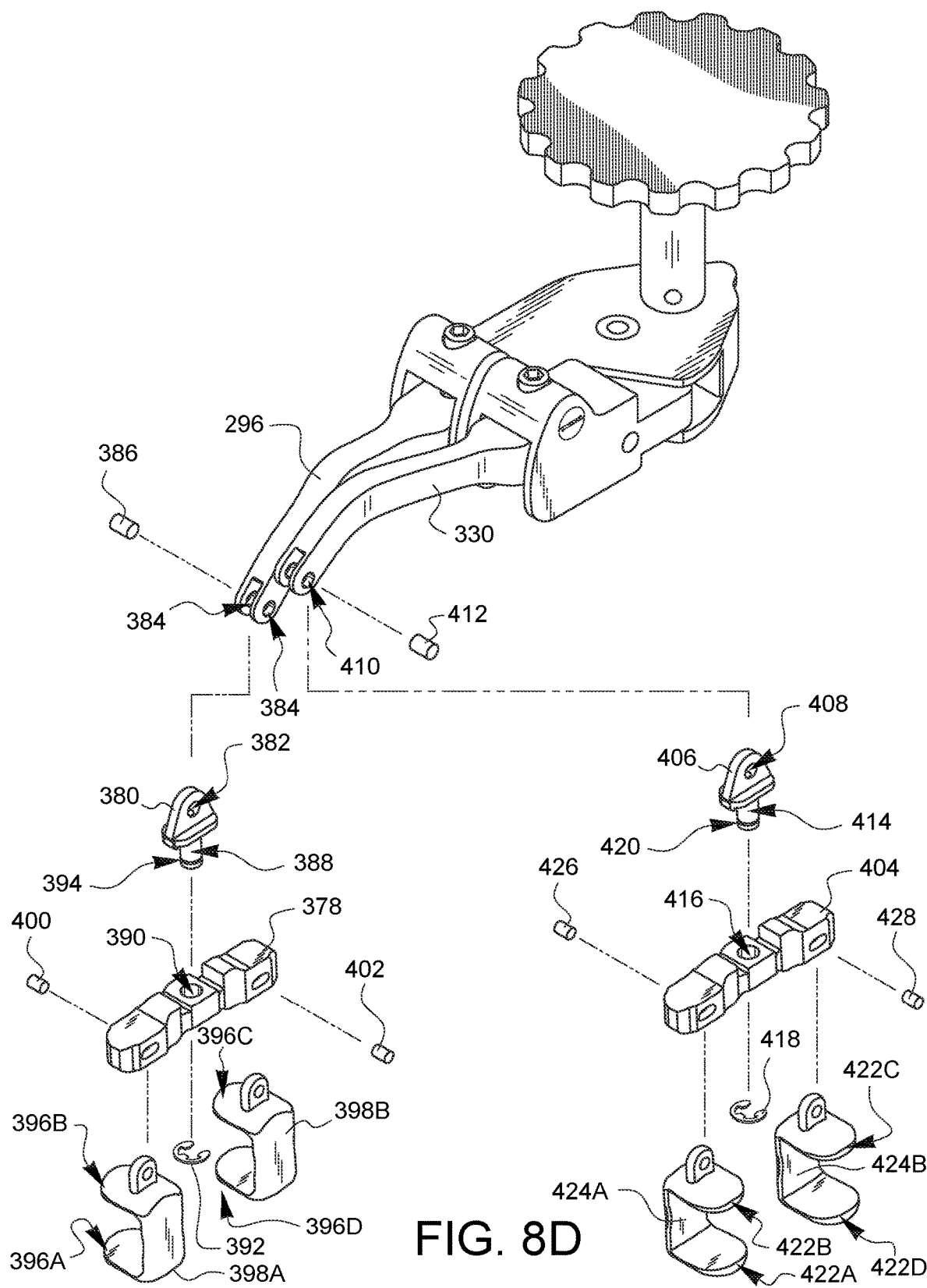

The first arm unit 248 of FIG. 7A comprises a first arm 296 (previously discussed with regard to FIG. 8A) and a first strut 378, as shown in the partially exploded view of FIG. 8D. In this embodiment, the first strut 378 is pivotably coupled to the first arm 296 by a first adapter 380 having a hole 382 that is held in alignment with holes 384 in first arm 296 by axle 386. A post 388 on adapter 380 passes through a corresponding hole 390 in the first strut 378, which is then held onto the post 388 by a clip 392 that is attached to a groove 394 in the post 388. In this embodiment, the adapter 380 allows the strut 378 to pivot with two degrees of freedom (on axle 386 and on post 388) relative to the arm 296. In other embodiments, the strut 378 may have more or fewer degrees of freedom relative to the arm 296. In some embodiments, the strut 378 may be continuously formed with the arm 296. Depending on the embodiment, the strut 378 may be inflexible or flexible.

In this embodiment, the first strut 378 also comprises one or more rib engaging fingers, such as rib engaging fingers 396A, 396B, 396C, 396D. In this embodiment, rib engaging fingers 396A, 396B form a first opposing pair of rib engaging fingers 398A, while rib engaging fingers 396C, 396D form a second opposing pair of rib engaging fingers 398B. The rib engaging fingers are configured to be placed around or adjacent to a rib for pulling and/or pushing on the rib. Depending on the embodiment, the rib engaging fingers may be covered with a softer covering to provide protection for the ribs. In this embodiment, the first opposing pair of rib engaging fingers 398A is coupled to the first strut 378 by a pin 400, while the second opposing pair of rib engaging fingers 398B is coupled to the first strut 378 by a pin 402. In this embodiment, the pins 400, 402 have some freedom of movement to pivot and/or slide, which may help the rib engaging fingers to be placed around a rib during a surgical procedure. Other embodiments may have more or fewer rib engaging fingers.

The second arm unit 250 of FIG. 7A comprises a second arm 330 (previously discussed with regard to FIG. 8B) and a second strut 404, as shown in the partially exploded view of FIG. 8D. In this embodiment, the second strut 404 is pivotably coupled to the second arm 330 by a second adapter 406 having a hole 408 that is held in alignment with holes 410 in second arm 330 by axle 412. A post 414 on adapter 406 passes through a corresponding hole 416 in the second strut 404, which is then held onto the post 414 by a clip 418 that is attached to a groove 420 on the post 414. In this embodiment, the adapter 406 allows the strut 404 to pivot with two degrees of freedom (on axle 412 and on post 414) relative to the arm 330. In other embodiments, the strut 404 may have more or fewer degrees of freedom relative to the arm 330. In some embodiments, the strut 404 may be continuously formed with the arm 330. Depending on the embodiment, the strut 404 may be inflexible or flexible.

In this embodiment, the second strut 404 also comprises one or more rib engaging fingers, such as rib engaging fingers 422A, 422B, 422C, 422D. In this embodiment, rib engaging fingers 422A, 422B form a third opposing pair of rib engaging fingers 424A, while rib engaging fingers 422C, 422D form a fourth opposing pair of rib engaging fingers 424B. The rib engaging fingers are configured to be placed around or adjacent to a rib for pulling and/or pushing on the rib. Depending on the embodiment, the rib engaging fingers may be covered with a softer covering to provide protection for the ribs. In this embodiment, the third opposing pair of rib engaging fingers 424A is coupled to the second strut 404 by a pin 426, while the fourth opposing pair of rib engaging fingers 424B is coupled to the second strut 404 by a pin 428. In this embodiment, the pins 426, 428 have some freedom of movement to pivot and/or slide, which may help the rib engaging fingers to be placed around a rib during a surgical procedure. Other embodiments may have more or fewer rib engaging fingers.

Figure 8E:
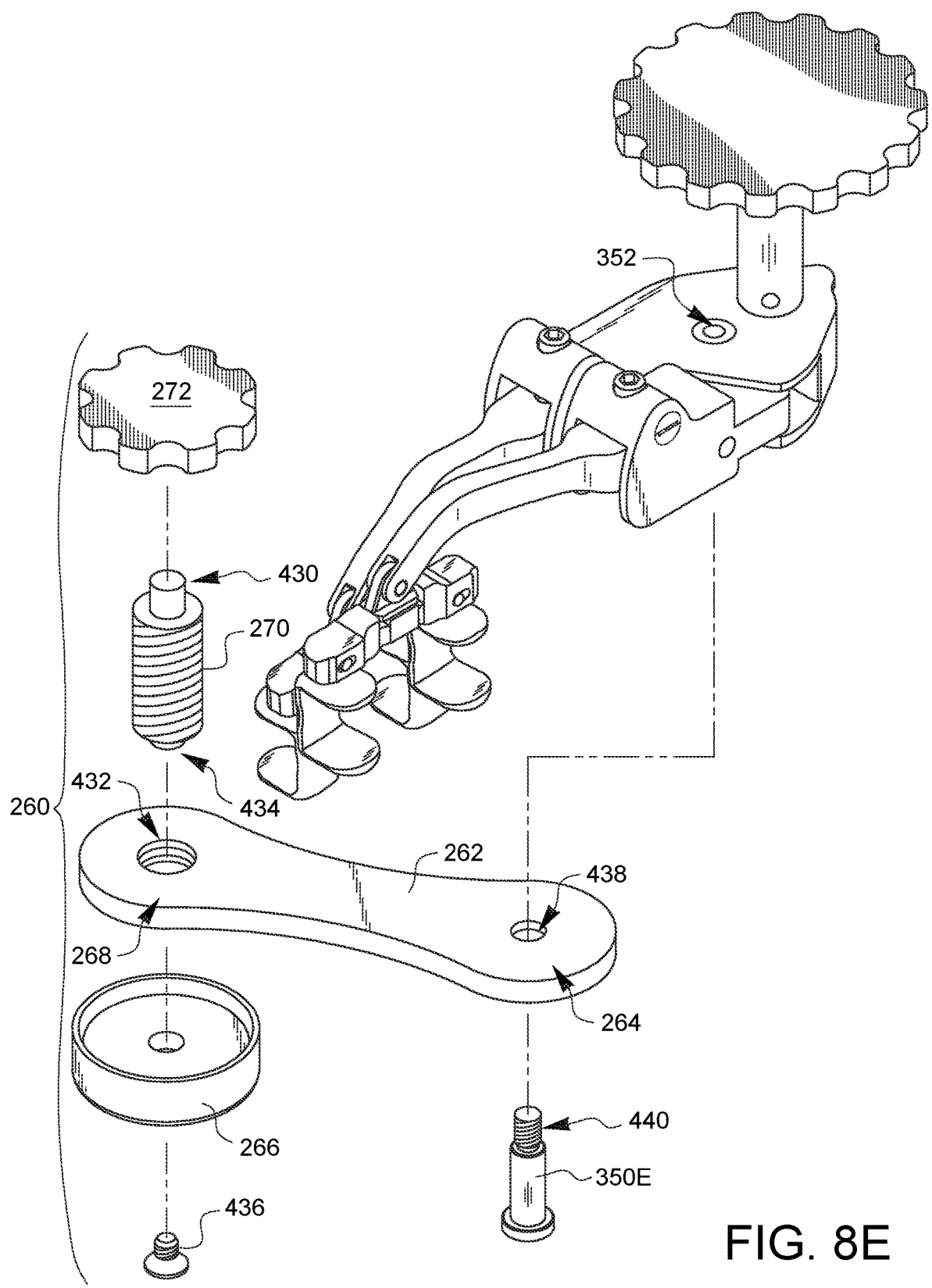

An exploded view of the anti-cant feature 260 is shown in FIG. 8E. The adjustment knob 272 is pressed onto or otherwise coupled to a first end 430 of the threaded post 270. The threaded post 270 is threaded into a threaded hole 432 in the distal end 268 of the lever arm 262. A footing 266 is coupled to a second end 434 of the threaded post 270 by a screw 436. Recalling the above discussion regarding the exploded view of FIG. 8B, the retractor has an axle 350 which passes through the holes 348, 346, and which may have threads which engage corresponding threads in hole 352. Although the axle 350 shown in FIG. 8B was generic, a more specific axle 350E is shown in FIG. 8E. Axle 350E would replace the generic axle 350, passing up through a hole 438 in the proximal end 264 of the lever arm 262. The axle 350E would then pass through the holes 348, 346 (not visible in this view) and then threads 440 on the axle 350E would thread into threaded hole 352, sticking out of hole 352 to act as an accessory connection point. Since the hole 438 in the proximal end 264 of the lever arm 262 is a clearance hole, the lever arm 262 and the entire anti-cant feature 260 may be pivoted about axle 350E to a desired position.

FIG. 9A illustrates one view of a retractor 238B, like the retractor 238 of FIG. 7A, but without the anti-cant feature, installed in a minimally invasive surgical opening 442. In particular, rib-engaging fingers 398A, 398B have been positioned around a first rib 444, while rib-engaging fingers 424A, 424B have been positioned around a second rib 446. The body 244 has been moved with respect to the housing 240 to create relative movement between the first and second arm units 296, 300 in a first plane 448. This movement was caused by turning the drive actuator 256 to engage the drive gear (not visible in this view). The arm actuators 252, 254 have also been turned to pivot the first arm unit 296 down (with respect to the first shoulder 242) and the second arm unit 330 up (with respect to the second shoulder 246) to create a relative movement between the two arm units 296, 330 in a second direction 450 that is substantially perpendicular to the movement 448. As used in FIG. 9A, the retractor 238B provides excellent surgical access through the minimally invasive surgical opening. However, in some scenarios, it may be desirable to prevent or at least reduce the amount of tipping or canting which may occur when the ribs are the only point of contact for the retractor 238B.

Figure 9B:
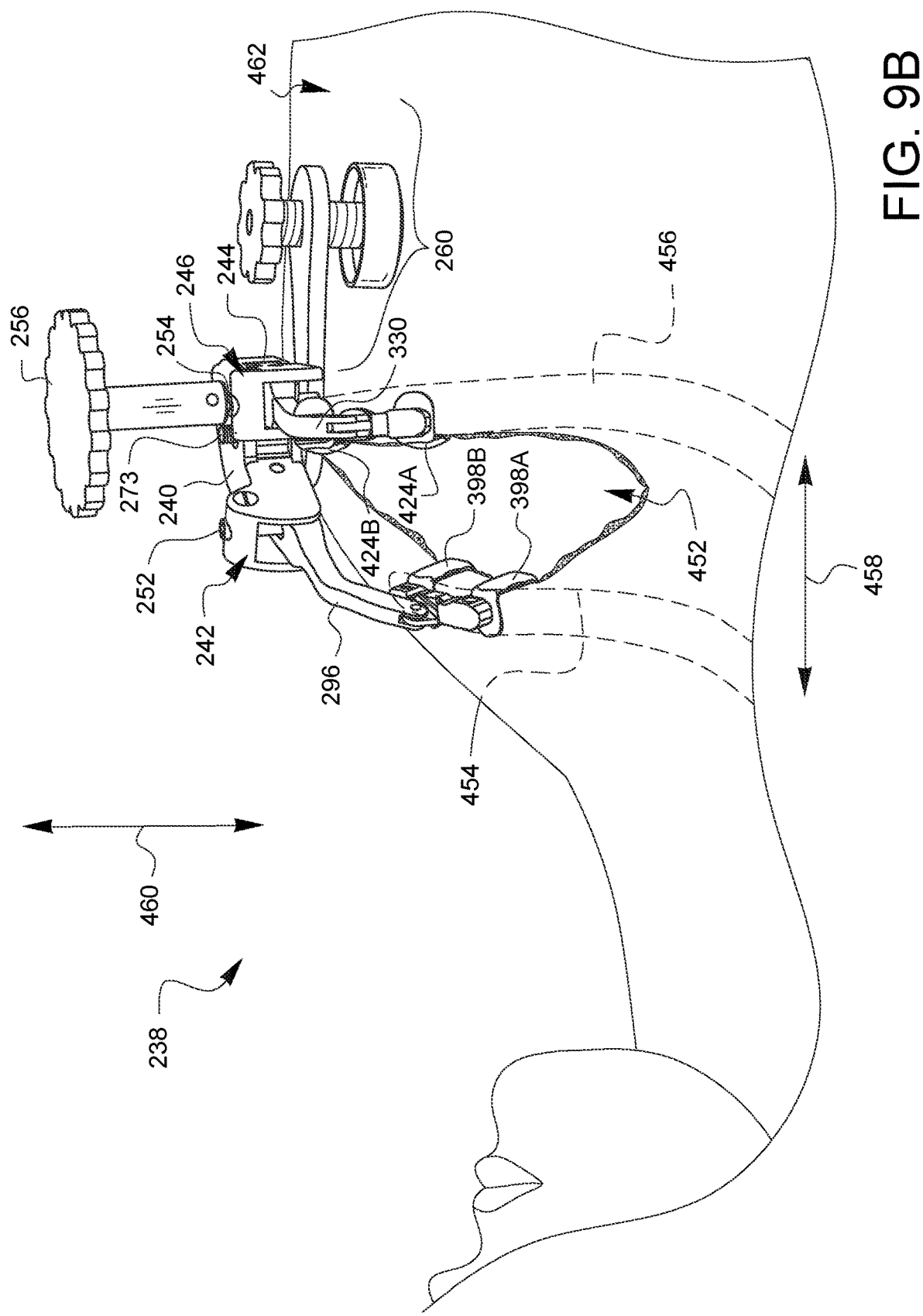
FIG. 9B illustrates one view of the retractor from FIG. 7A installed in a minimally invasive surgical opening with the anti-cant feature.

Accordingly, FIG. 9B illustrates one view of the retractor 238 from FIG. 7A, with the anti-cant feature 260, installed in a minimally invasive surgical opening 452. In particular, rib-engaging fingers 398A, 398B have been positioned around a first rib 454, while rib-engaging fingers 424A, 424B have been positioned around a second rib 456. The body 244 has been moved with respect to the housing 240 to create relative movement between the first and second arm units 296, 300 in a first plane 458. This movement was caused by turning the drive actuator 256 to engage the drive gear (not visible in this view). The arm actuators 252, 254 have also been turned to pivot the first arm unit 296 down (with respect to the first shoulder 242) and the second arm unit 330 up (with respect to the second shoulder 246) to create a relative movement between the two arm units 296, 330 in a second direction 460 that is substantially perpendicular to the movement 458. As used in FIG. 9B, the retractor 238 provides excellent surgical access through the minimally invasive surgical opening 452. However, since the anti-cant feature 260 is contacting the patient's chest 462, the retractor 238 tends to tip less. This may be desirable for a number of reasons, including, but not limited to: 1) keeping the retractor out of the surgeon's way and 2) providing a platform which is more aligned with the patient's chest, for example, if needing to attach an accessory to the accessory attachment point 273. In the example of FIG. 9B, the accessory attachment feature 273 is substantially perpendicular to the patient's chest due to the position of the anti-cant feature 260.

Figure 10:
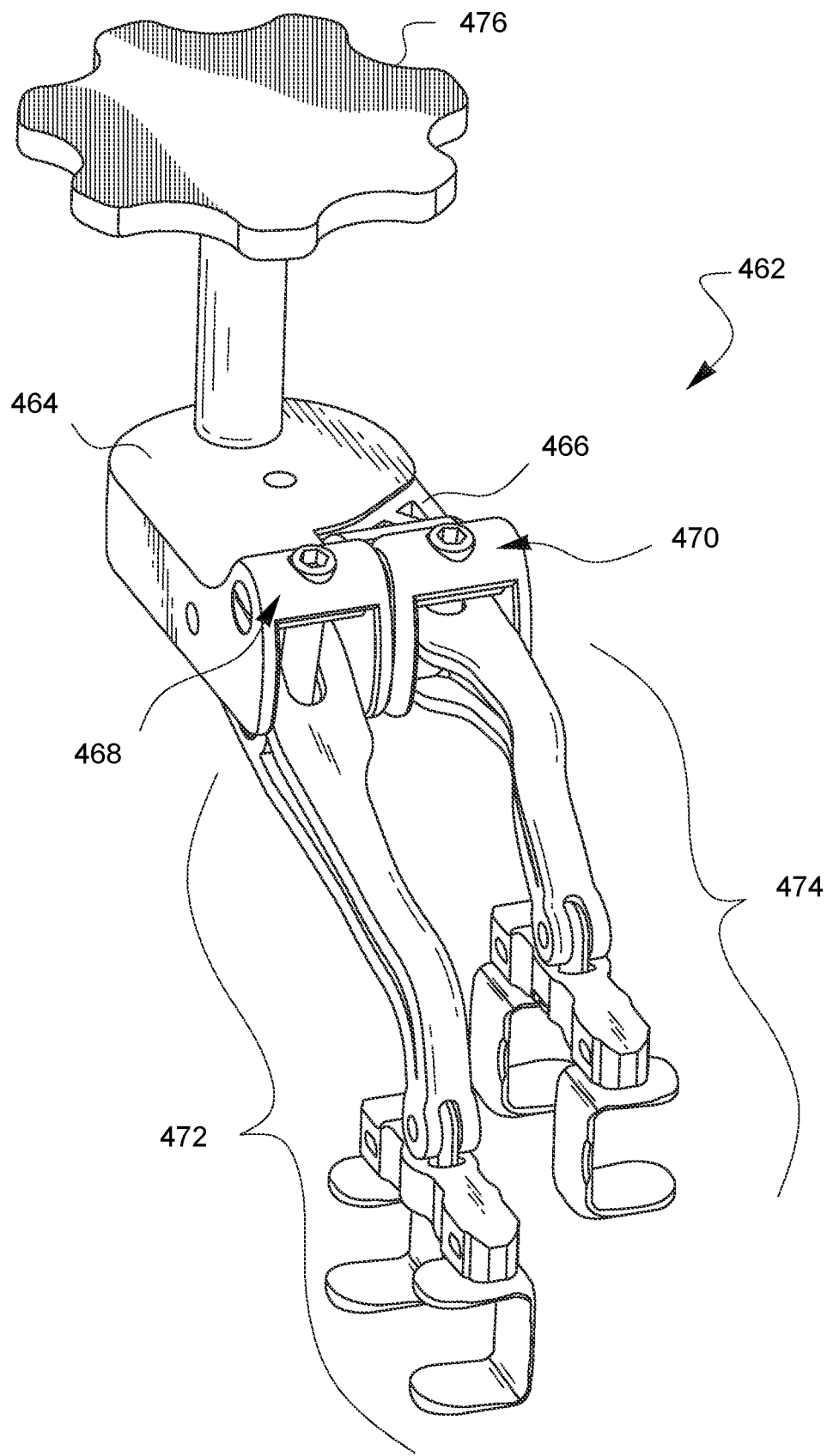
FIG. 10 illustrates another embodiment of a surgical rib retractor.

FIG. 10 illustrates a further embodiment of a surgical rib retractor 462. Like previous embodiments, the embodiment of FIG. 10 has a housing 464 and a body 466 pivotably coupled to the housing 464. The housing 464 has a first shoulder 468, while the body 466 has a second shoulder 470. The first shoulder 468 is coupled to a first arm unit 472, while the second shoulder 470 is coupled to a second arm unit 474. Both the first and second arm units 472, 474 and the relative movements caused between them work similarly to previous embodiments, so those aspects will not be repeated in this discussion of FIG. 10. As before, there is a drive actuator 476 which can engage a drive gear (not visible in FIG. 10) coupled to the body 466.

Figure 11:
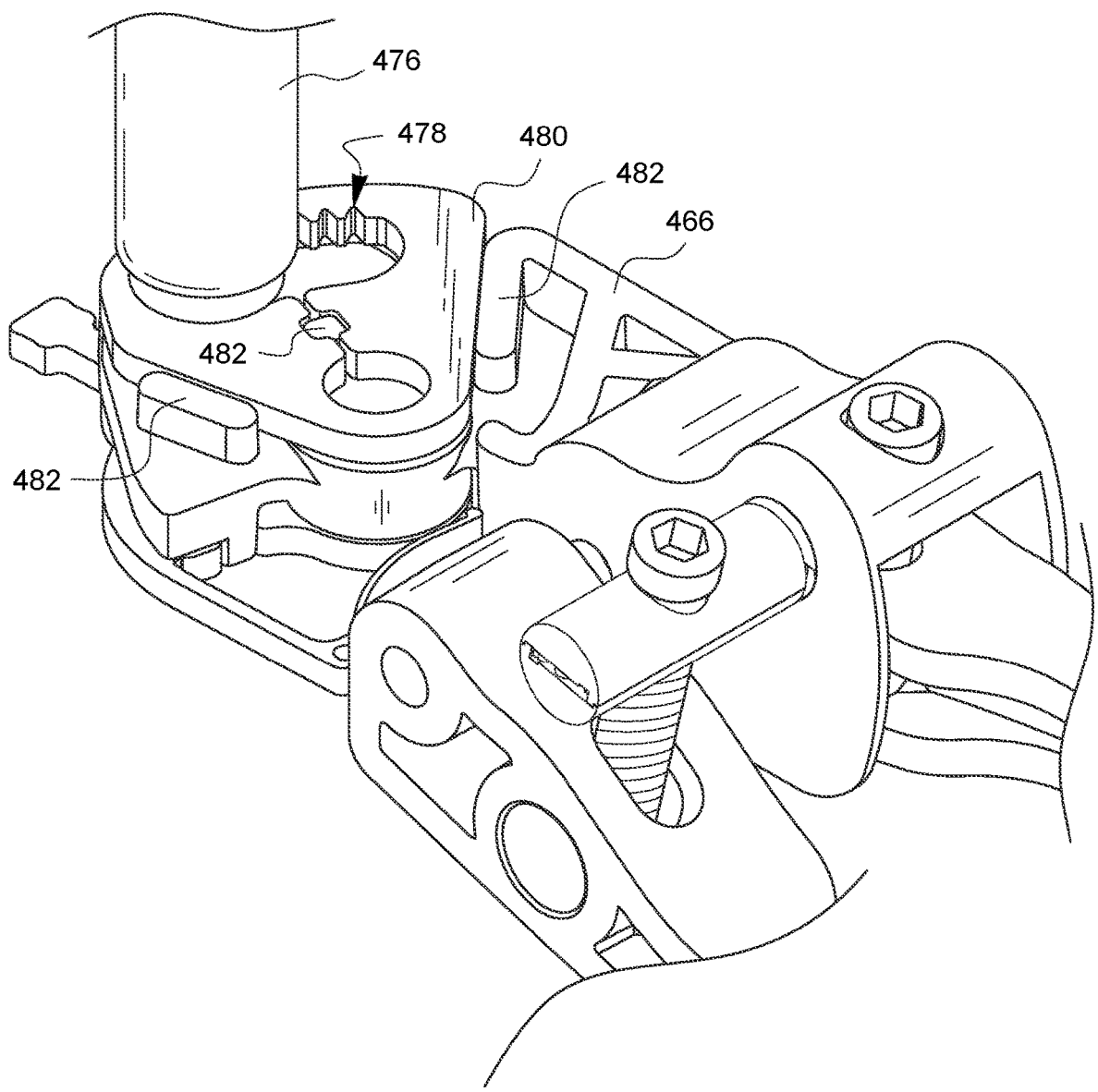
FIG. 11 is a partially exposed view of a portion of the surgical rib retractor of FIG. 10, providing a closer look at the body with the housing removed.
Figure 12:
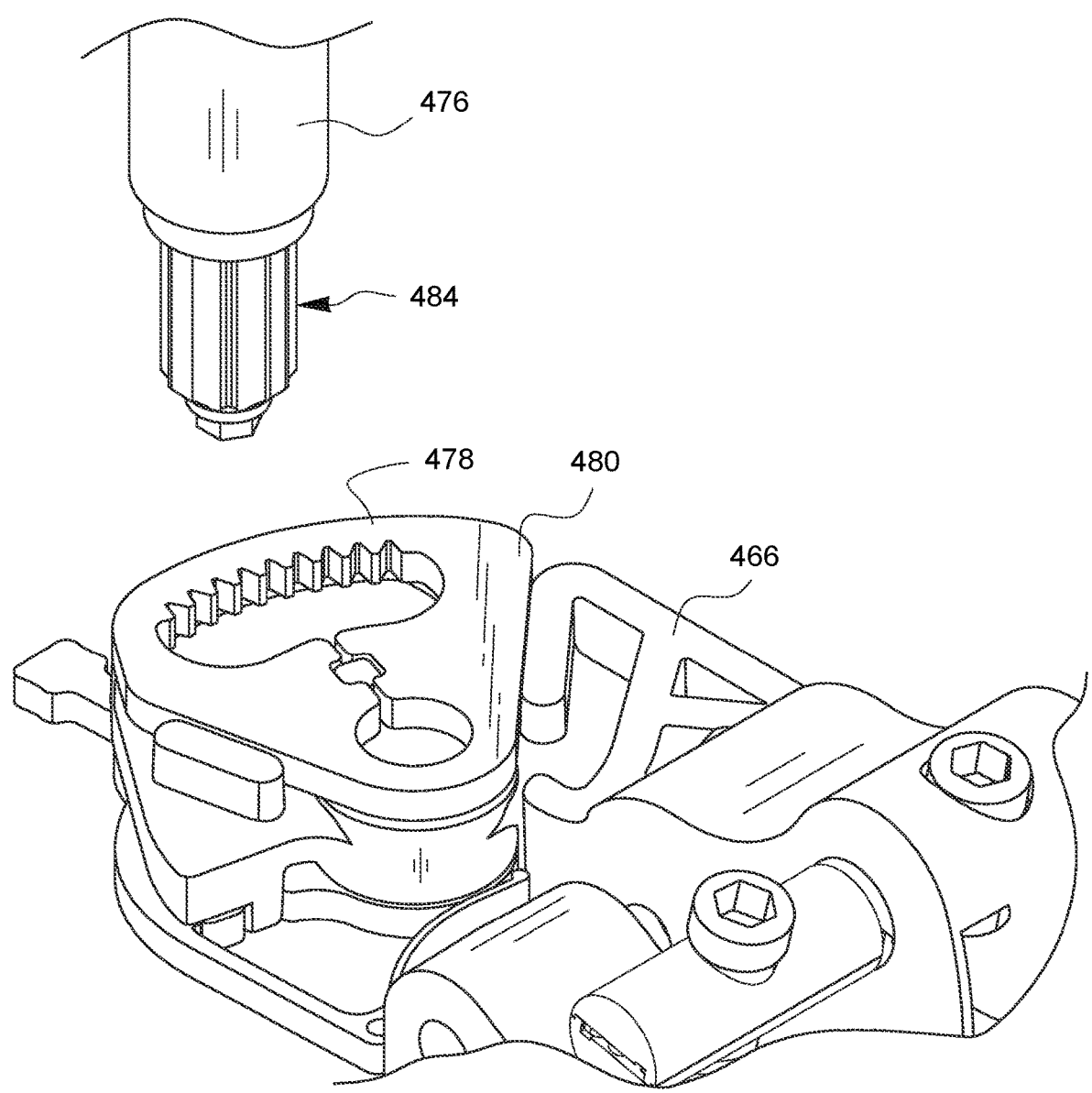
FIG. 12 is a partially exposed view showing the drive actuator of the surgical rib retractor of FIG. 10 lifted upwards so the actuation gear is no longer engaging the drive gear.

FIG. 11 provides a closer look at the body 466 with the housing removed. In this embodiment, the drive gear 478 (which is now visible) is formed as part of a drive gear component 480. The drive gear component 480 is held in place relative to the body 466 by complementary features 482 of the body 466. The drive gear component 480 is also prevented from lifting off of the body 466 by the housing (which is removed in this view). FIG. 12 shows the drive actuator 476 lifted upwards so the actuation gear 484 is no longer engaging the drive gear 478. In this view, the drive gear 478 may be seen more completely.

Figure 13:
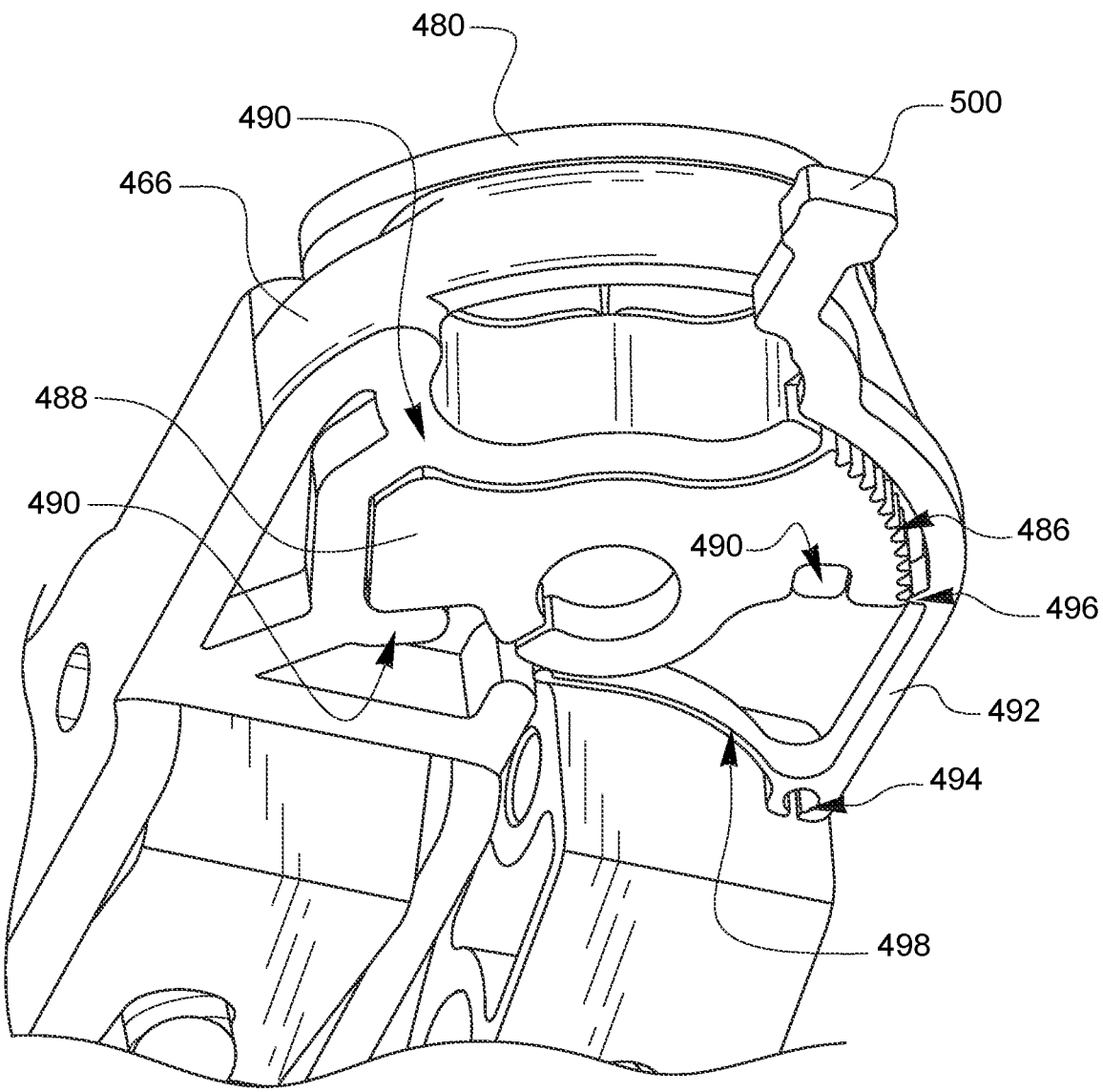
FIG. 13 is a partially exposed bottom view of the body of the surgical rib retractor of FIG. 10.

FIG. 13 is a bottom view of the body 466 with the housing removed for visibility. In this embodiment, the ratchet gear 486 is formed as part of a ratchet gear component 488. The ratchet gear component 488 is held in place relative to the body 466 by complementary features 490 of the body 466. The ratchet gear component 488 is also prevented from falling off of the body 466 by the housing (which is removed in this view). FIG. 13 also shows the pawl arm 492 which is coupled to the housing (not visible in this view) at a pawl arm pivot point 494. Like previous embodiments, the pawl arm 492 has a pawl 496 which engages the ratchet gear 486. The pawl 496 is shown separated from the ratchet gear 486 in this view so that the teeth may better be seen. Normally, the pawl 496 would be biased against the ratchet gear 486 by a biasing spring 498 which pushes against the ratchet component 488. In this embodiment, the drive actuator 476 does not disengage the pawl 496 from the ratchet gear 486. Instead, in this embodiment, the pawl arm 492 also has a pawl release 500 which extends outside of the housing through a slot in the housing (housing not visible in this view). A user of the device may move the pawl release 500 to disengage the pawl 496 from the ratchet gear 486 as desired, independently from what the drive actuator is doing.

Figure 14:
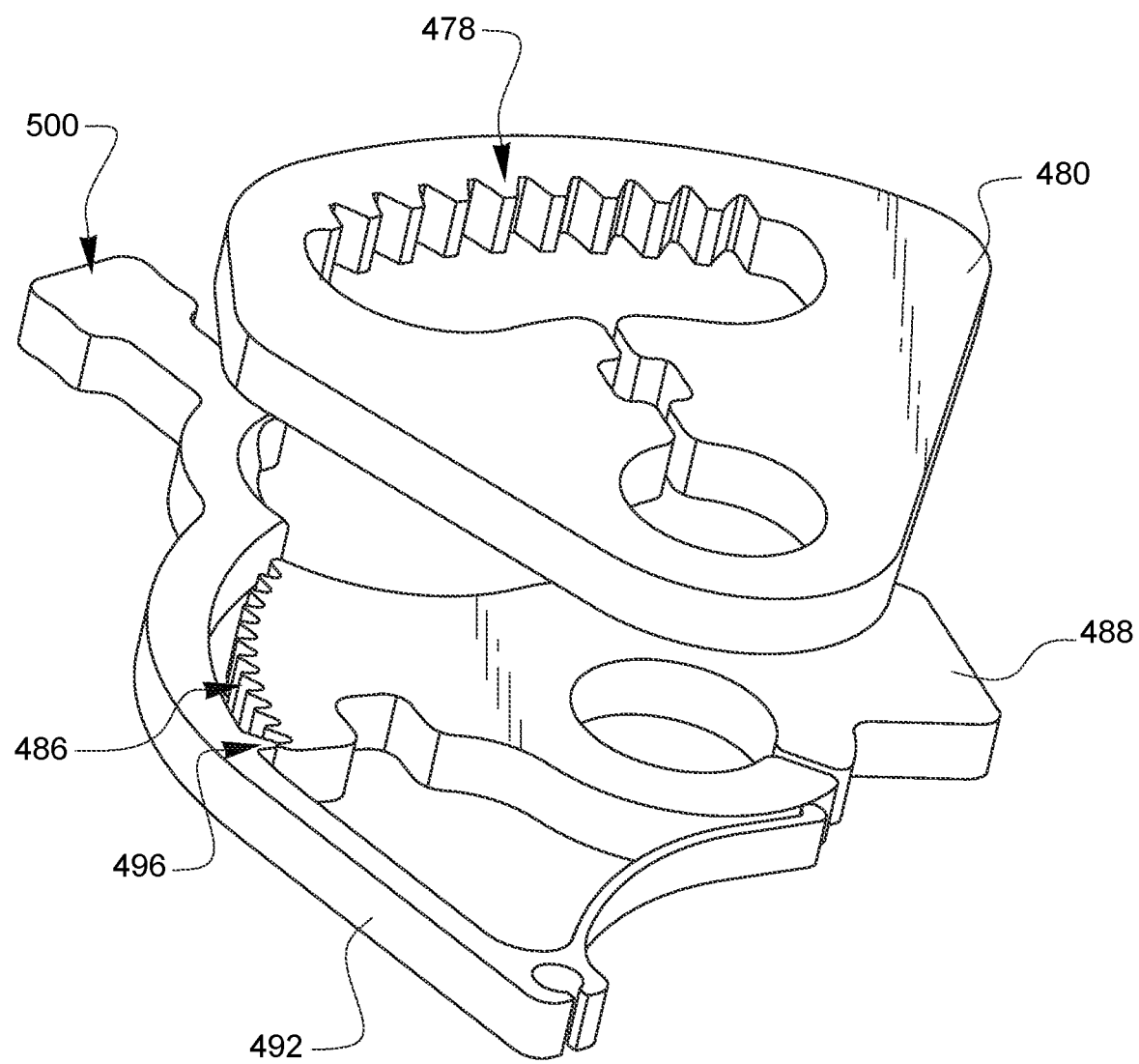
FIG. 14 is a perspective view showing only the drive gear component, the ratchet gear component, and the pawl arm of the surgical rib retractor of FIG. 10.

FIG. 14 is a top view showing only the drive gear component 480, the ratchet gear component 488, and the pawl arm 492. In this embodiment, the drive gear 478 and the ratchet gear 486 each lie in planes which do not intersect, thereby allowing for a more compact design and a simpler manufacturing process and assembly. Furthermore, by having the drive gear component 480 and the ratchet gear component 488 be separate assemblies from the body 466, this enables the gears to be made from a different material from the body. This may have an advantage in that the gears could be made from a stiffer material from the body to add strength where it is needed, while not, perhaps, using more expensive materials on the body.

Figure 15:
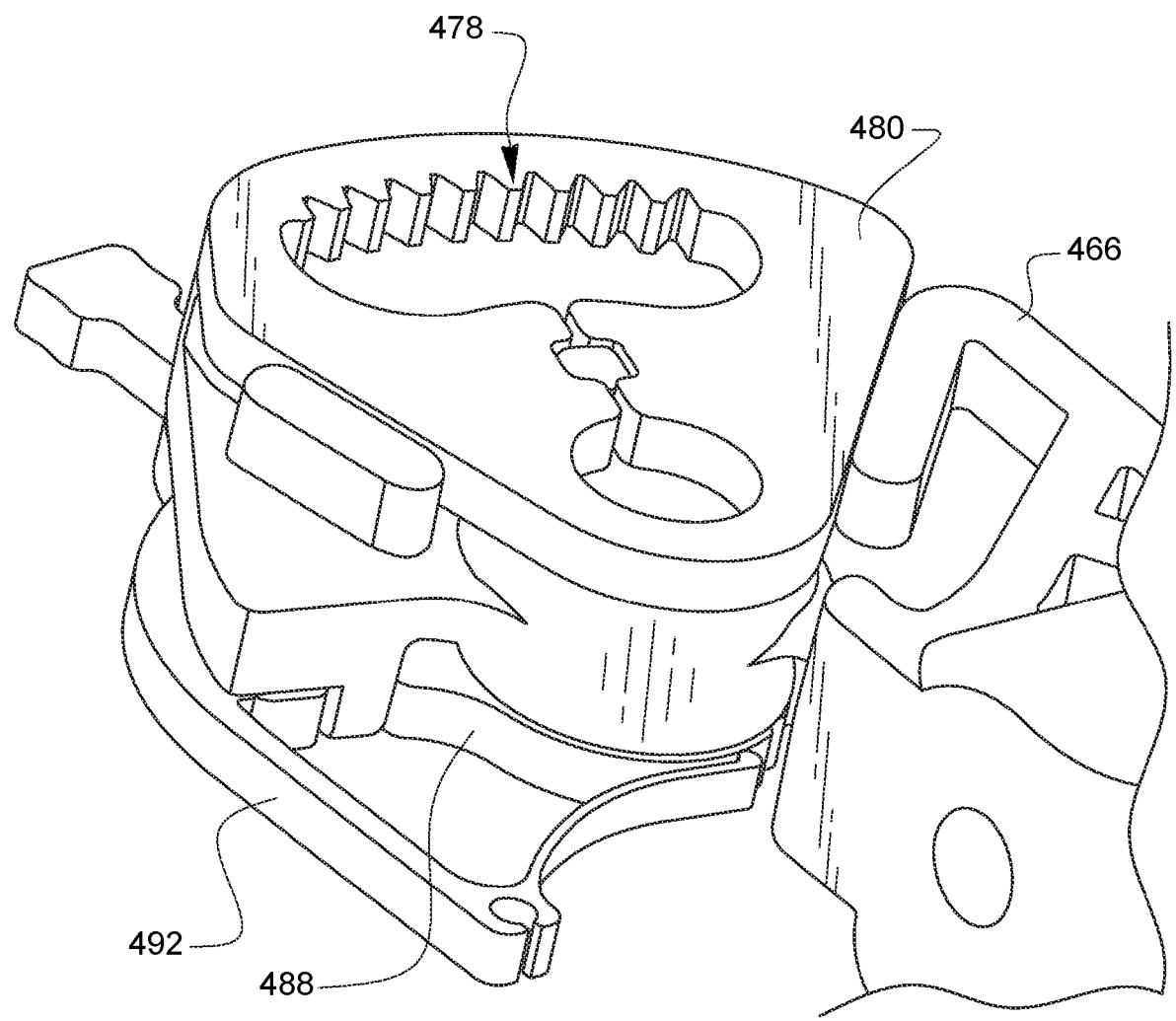
FIG. 15 is a partially exposed top view of a body assembly of the surgical rib retractor of FIG. 10.

FIG. 15 is a top view of a body assembly, comprising the body 466, the drive gear component 480, and the ratchet gear component 488. In the view of FIG. 15, the body assembly is also shown interacting with the pawl arm 492.

Figure 16:
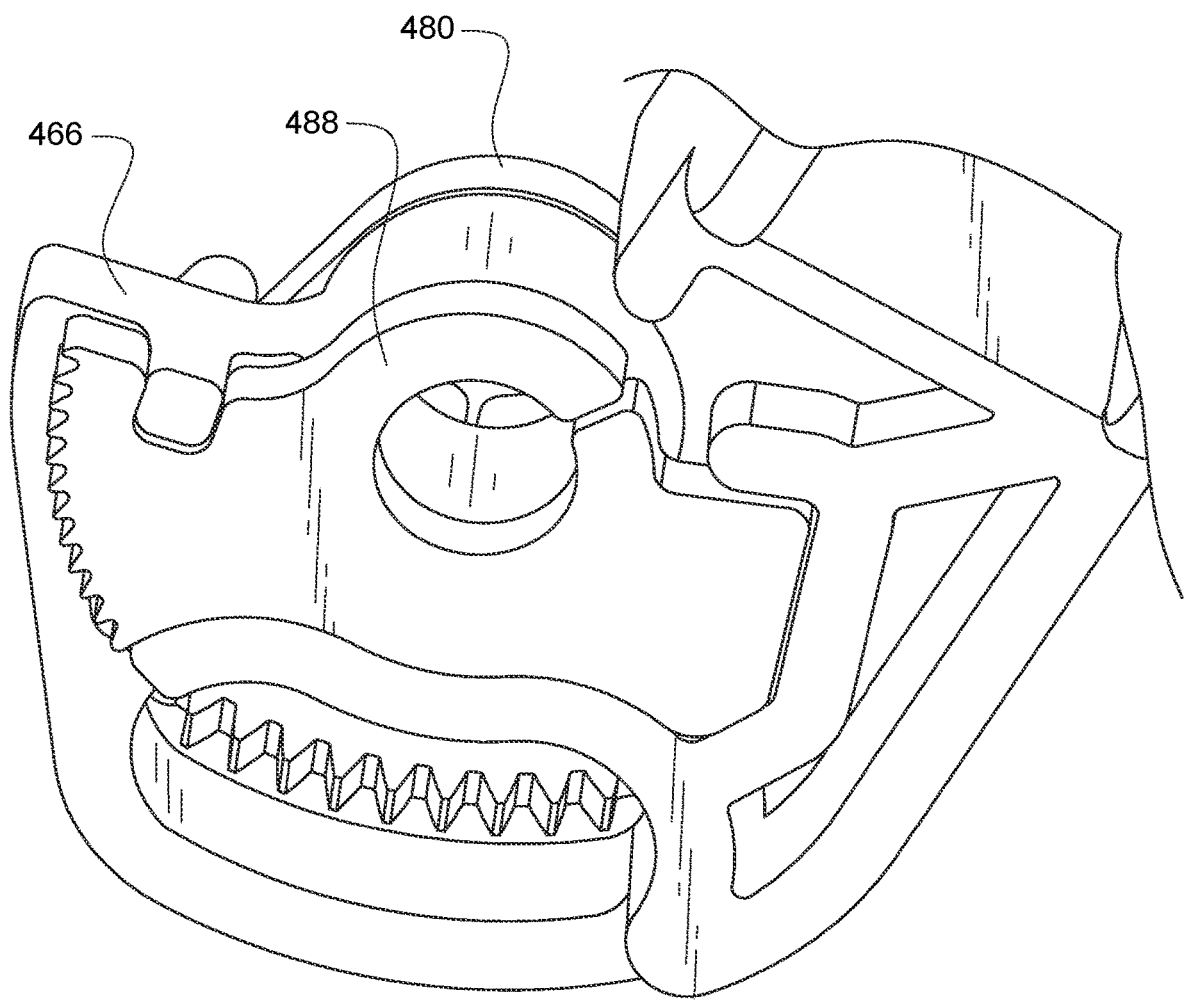
FIG. 16 is an exposed bottom view of the body assembly of FIG. 16.

FIG. 16 is a bottom view of the body assembly on its own. Again, the body assembly comprises the body 466, the drive gear component 480, and the ratchet gear component 488. Depending on the embodiment, the different elements of the body assembly may be held together by constraints and/or they may be coupled by a variety of techniques including, but not limited to welding and gluing. Each of the elements of the body assembly may be made from similar and/or different materials to suit their application. As just one non-limiting example, it may be desirable to have the body made from plastic while the gears could be made from metal so that the gears would be able to handle greater stresses when used to retract ribs.

Figure 17:
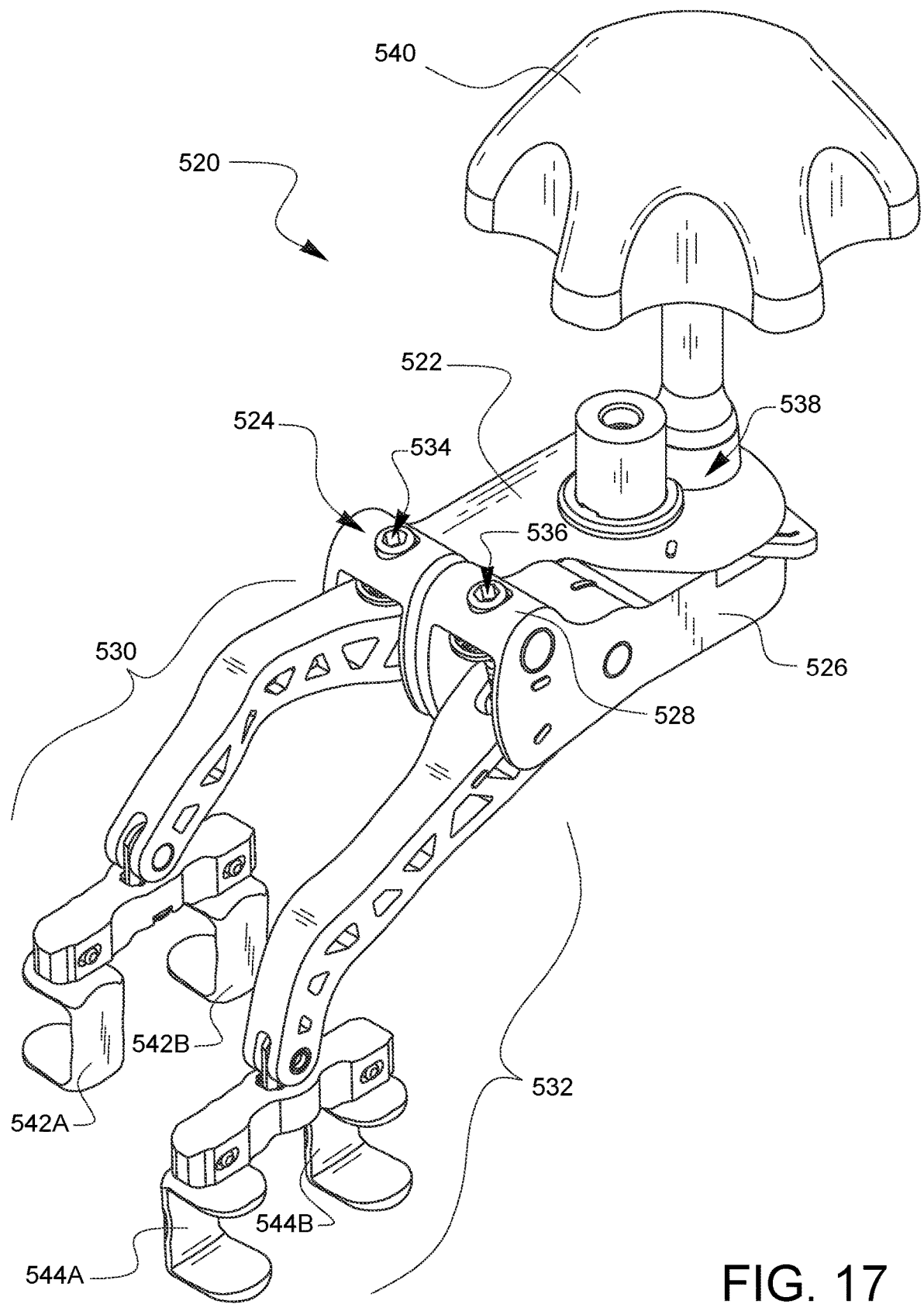
FIG. 17 is a perspective view of another embodiment of a surgical rib retractor.

FIG. 17 is a perspective view of another embodiment of a surgical rib retractor 520. The retractor 520 has a housing 522. The housing 522 has a first shoulder 524. The retractor 520 also has a body 526 pivotably coupled to the housing 522 and having a second shoulder 528. The surgical rib retractor 520 also has a first arm unit 530 pivotably coupled to the first shoulder 524 and configured to receive one rib. The surgical rib retractor 520 also has a second arm unit 532 pivotably coupled to the second shoulder 528 and configured to receive another rib.

The surgical rib retractor 520 has a first arm actuator 534 constrained to be rotatable relative to the first shoulder 524 and coupled to the first arm unit 530 to pivot the first arm unit 530 as the first arm actuator 534 is rotated. Similarly, the retractor 520 also has a second arm actuator 536 constrained to be rotatable relative to the second shoulder 528 and coupled to the second arm unit 532 to pivot the second arm unit 532 as the second arm actuator 536 is rotated.

The surgical rib retractor 520 also has a drive actuator 538. The drive actuator 538 is configured to pivot the body 526 relative to the housing 522. In this embodiment, the drive actuator 538 includes a knob 540 and a gear (not visible in this view). In other embodiments, the drive actuator could comprise a variety of elements, including one or more gears, one or more knobs, one or more levers, one or more pulleys, one or more motors, one or more solenoids, or any combination thereof.

In the embodiment of FIG. 17, the first arm unit 530 has two pairs of rib engaging fingers 542A, 542B. Similarly, the second arm 532 unit has two pairs of rib engaging fingers 544A, 544B. The pairs of rib engaging fingers 542A, 542B from the first arm unit 530 are configured to be placed against a first rib made accessible via a minimally invasive incision in an intercostal space. The pairs of rib engaging fingers 544A, 544B from the second arm unit 532 are configured to be placed against an adjacent rib also made accessible via the minimally invasive incision. The rib engaging fingers press against and push or pull on a given rib to expand the minimally invasive incision to create a minimally invasive access point.

Figure 18:
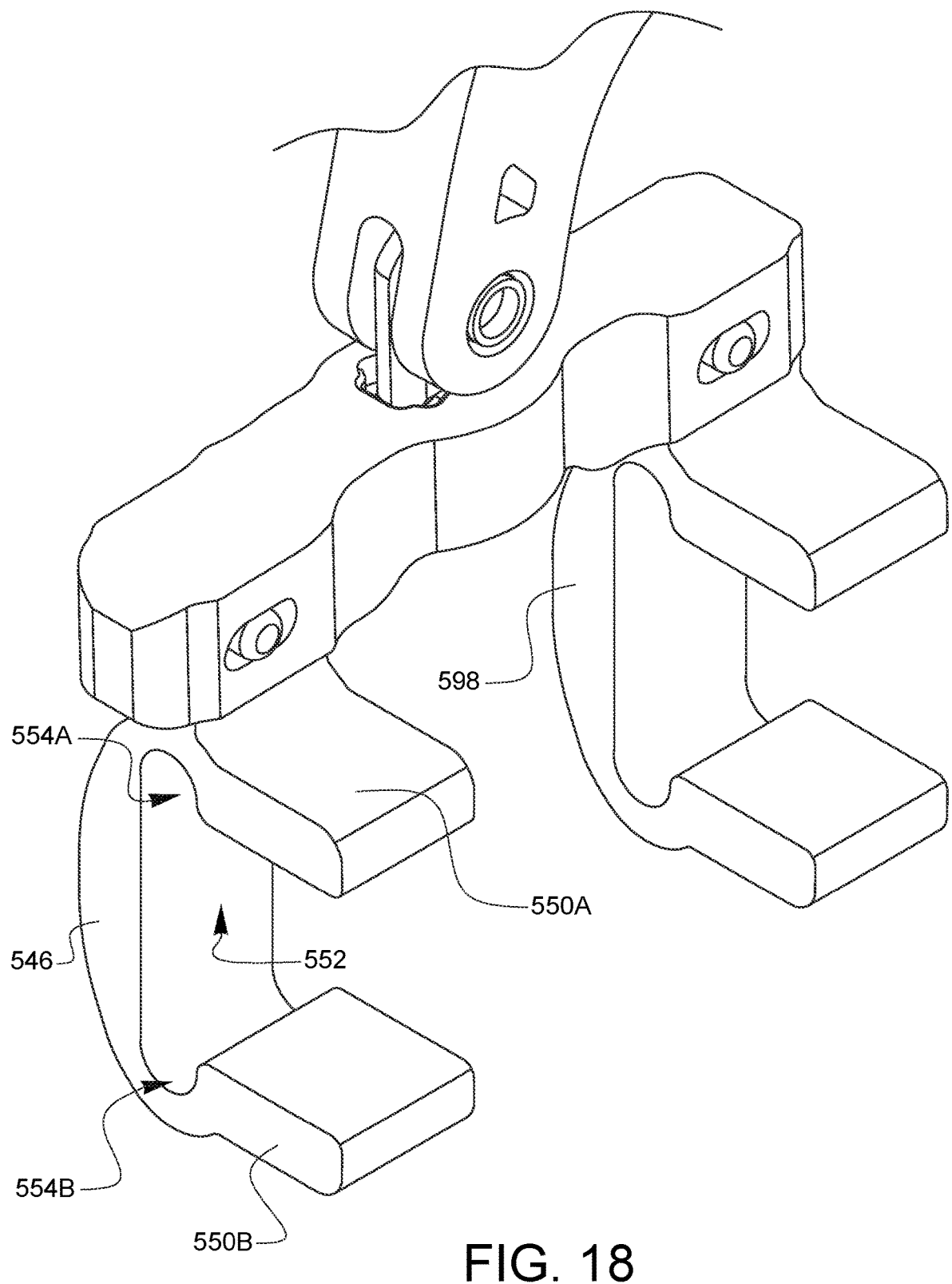
FIG. 18 shows an enlarged view of an embodiment of two pairs of rib engaging fingers.

FIG. 18 shows an enlarged view of two pairs 546, 548 of rib engaging fingers. Each of the pairs 546, 548 are similar, so for simplicity, only pair 546 will be discussed herein. In this embodiment, the pair 546 of rib engaging fingers comprises a first rib engaging finger 550A and a second rib engaging finger 550B. A wall 552 couples the rib engaging fingers 550A, 550B together and is oriented substantially perpendicular to the rib engaging fingers 550A, 550B. In the areas where each rib engaging finger 550A, 550B joins with the wall 552, separate nerve notches 554A, 554B are defined, respectively. The nerve notches 554A, 554B are formed in the space of the rib engaging fingers 550A, 550B and do not intrude on the plane of the wall 552 in this embodiment.

Figure 19:
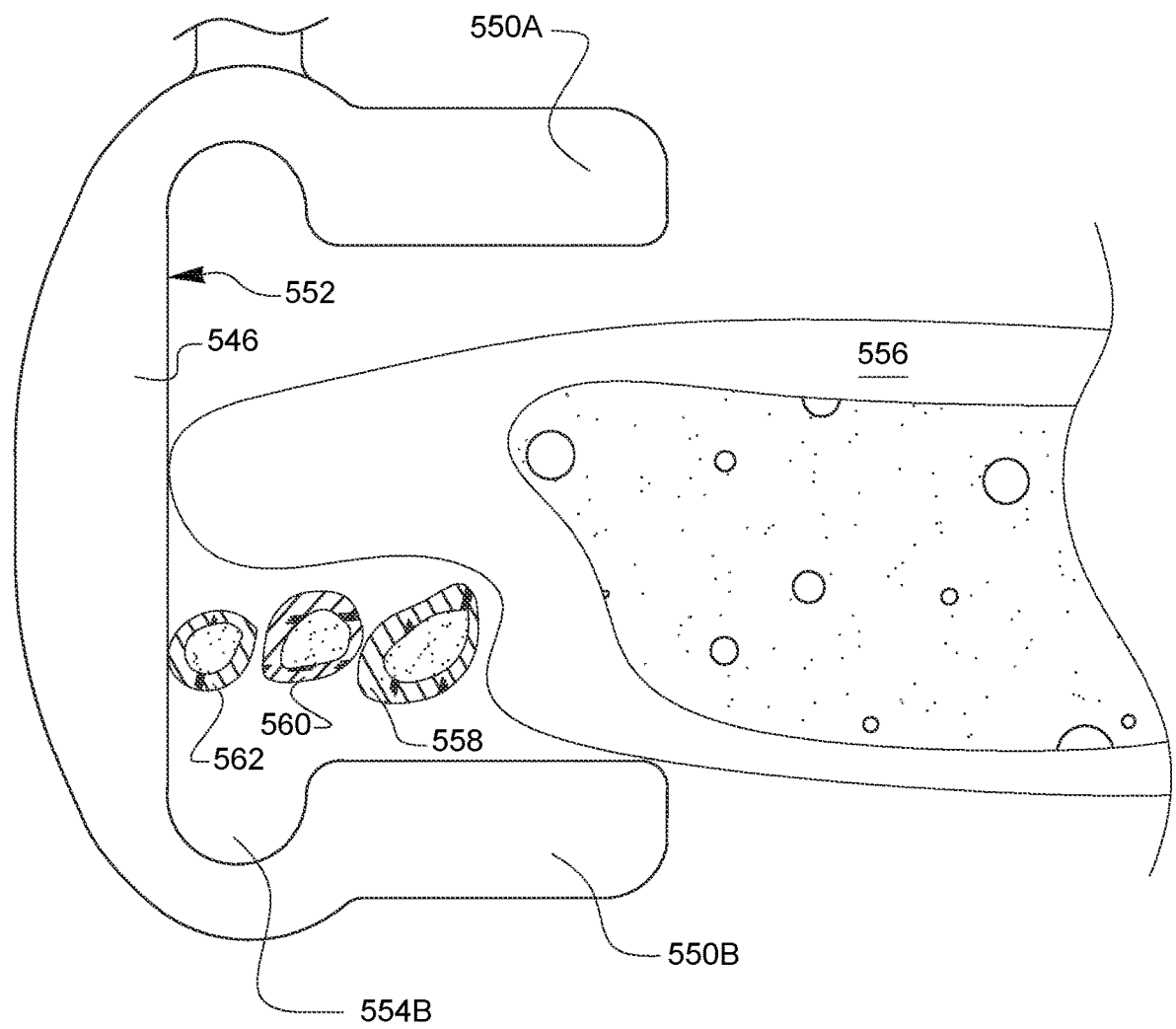
FIG. 19 is a side partial cross-sectional view of the pair of rib engaging fingers from FIG. 18 engaged with a rib.

FIG. 19 is a side partial cross-sectional view of the pair 546 of rib engaging fingers 550A, 550B engaged with a rib 556. The rib 556 is pressed against the wall 552. On the underside of the rib 556, an intercostal artery 558, vein, 560, and nerve 562 are located in such a way that the rib 556 normally protects them from damage. When using a retractor, however, especially one which has rib engaging fingers 550A, 550B, there is concern that one or more of these artery 558, vein 560, or nerve 562 can become pinched in the corner between the wall 552 and the rib engaging finger 550B. The embodiment of FIG. 19 reduces such concern, however, with the inclusion of the nerve notch 554B. The nerve notch 554B provides a space for the artery 558, vein 560, and/or nerve 562 to occupy without being pinched, while still enabling the wall 552 and the rib engaging fingers 550B, 550A to do their job of fully engaging the rib 556. This has the advantage of reducing patient trauma because these sensitive nerves and vessels may not be as likely to be damaged with such a design.

Figure 20B:
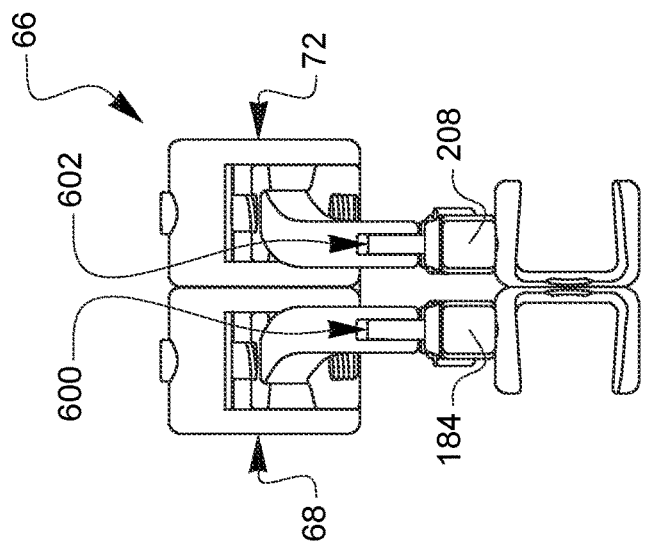
FIGS. 20A and 20B are top and front elevational views, respectively, of the surgical rib retractor from FIG. 1A with the drive actuator removed.
Figure 20A:
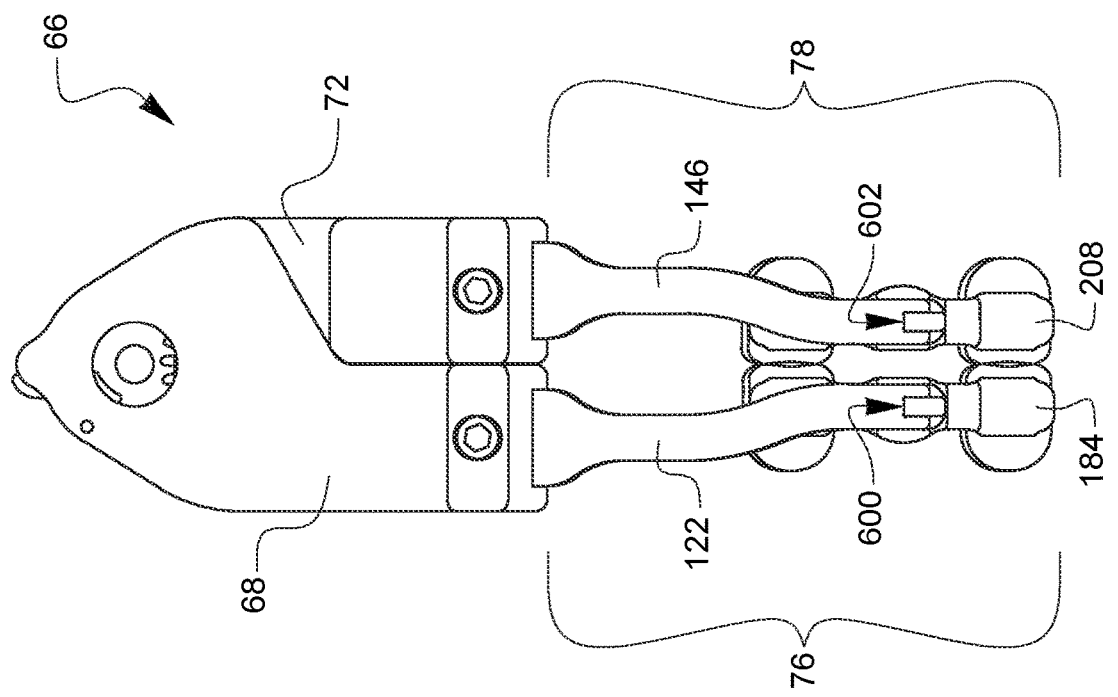

FIGS. 20A and 20B are top and front elevational views, respectively, of the surgical rib retractor 66 from FIG. 1A with the drive actuator removed. As previously disclosed, at least with regard to FIG. 6A, the body 72 is pivotably coupled to the housing 68. In FIGS. 20A and 20B, the body 72 is shown in a closed position relative to the housing 68, but as previously, disclosed, the body 72 can also be pivoted using the drive actuator (not shown in the view of FIG. 20A) into an open position away from the housing 68. The surgical rib retractor 66 also has a first arm unit 76 coupled to the housing 68. The first arm unit 76 includes a first arm 112 and a first strut 184 movable relative to the first arm 112 in a first plane defined by the first arm 112. The first plane is specifically defined in this embodiment by the slot 600 in the first arm 112. Similarly, the surgical rib retractor also has a second arm unit 78 coupled to the body 72. The second arm unit 78 includes a second arm 146 and a second strut 208 moveable relative to the second arm 146 in a second plane defined by the second arm 146. The second plane is specifically defined in this embodiment by the slot 602 in the second arm 146. In this embodiment, the first and second planes are substantially parallel when the body 72 is in the closed position relative to the housing 68 as shown in FIGS. 20A and 20B.

Figure 21B:
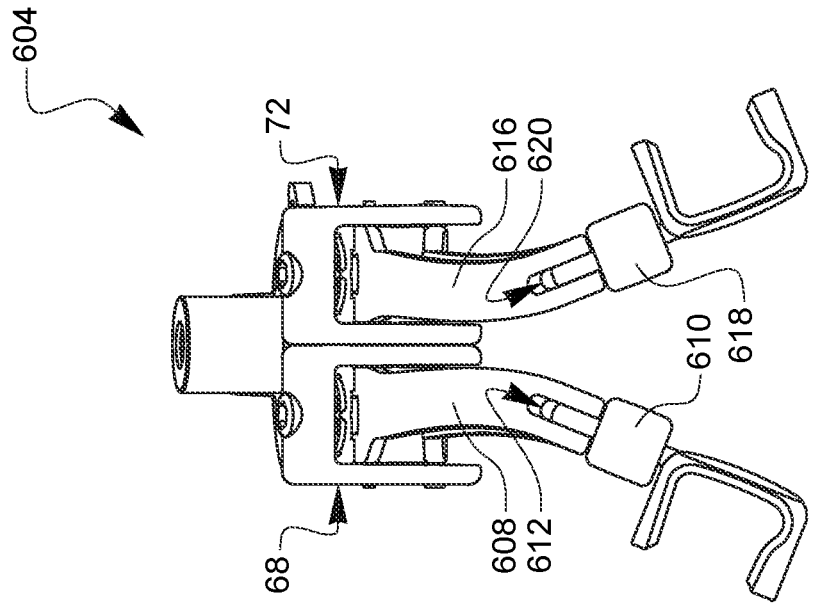
FIGS. 21A and 21B are top and front elevational views, respectively, of another embodiment of a surgical rib retractor.
Figure 21A:
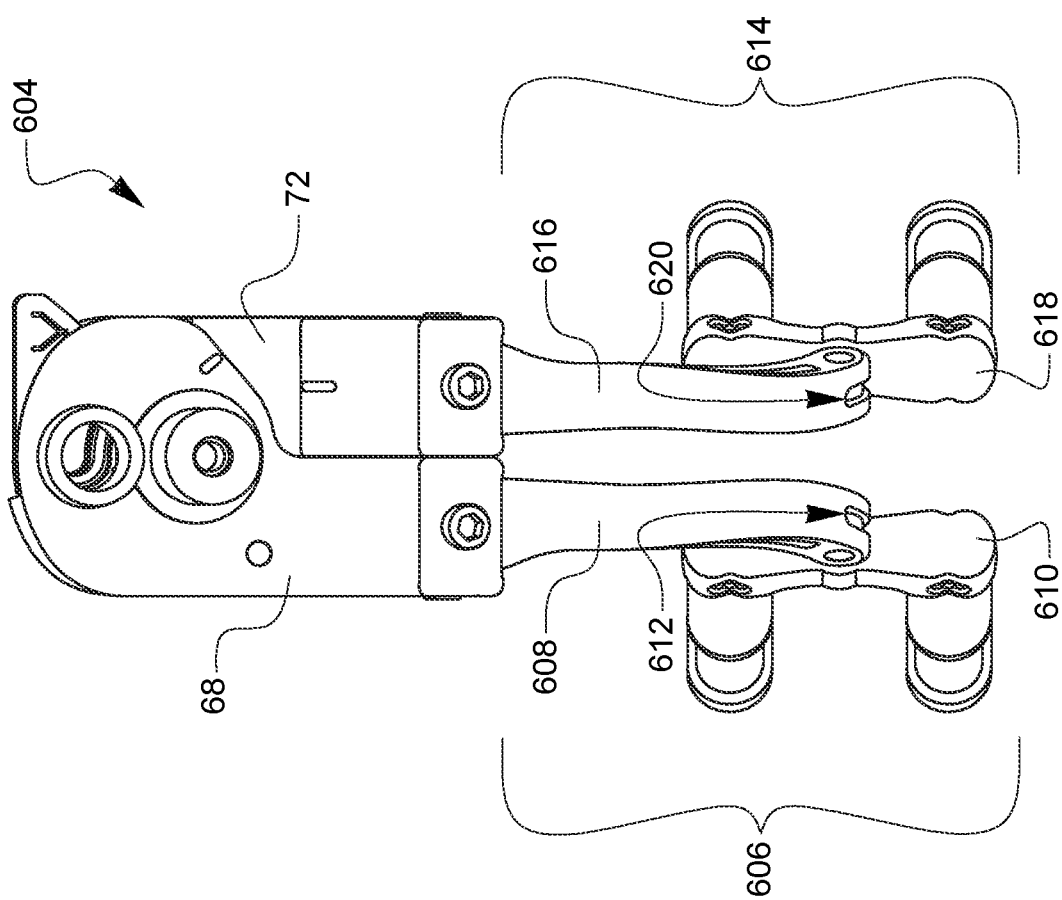

FIGS. 21A and 21B are top and front elevational views, respectively, of another embodiment of a surgical rib retractor 604. This retractor embodiment 604 is similar to previously disclosed retractor embodiments, however, in this embodiment, the first and second planes for strut movement, defined by the first and second arms, are not parallel to each other when the body is in the closed position. As previously disclosed, at least with regard to FIG. 6A, the body 72 is pivotably coupled to the housing 68. In FIGS. 21A and 21B, the body 72 is shown in a closed position relative to the housing 68, but as previously, disclosed, the body 72 can also be pivoted using the drive actuator (not shown in the view of FIG. 21A) into an open position away from the housing 68. The surgical rib retractor 604 also has a first arm unit 606 coupled to the housing 68. The first arm unit 606 includes a first arm 608 and a first strut 610 movable relative to the first arm 606 in a first plane defined by the first arm 608. The first plane is specifically defined in this embodiment by the slot 612 in the first arm 608. Similarly, the surgical rib retractor also has a second arm unit 614 coupled to the body 72. The second arm unit 614 includes a second arm 616 and a second strut 618 moveable relative to the second arm 616 in a second plane defined by the second arm 616. The second plane is specifically defined in this embodiment by the slot 620 in the second arm 616. In this embodiment, the first and second planes are not parallel to each other when the body 72 is in the closed position relative to the housing 68 as shown in FIGS. 21A and 21B. This cambered arrangement of the struts 610, 618 is advantageous because it may facilitate installation of the surgical retractor 604 through the space between ribs when seating the retractor 604. This advantage will be explained with regard to FIGS. 22A, 22B and FIGS. 23A, 23B.

Figure 22B:
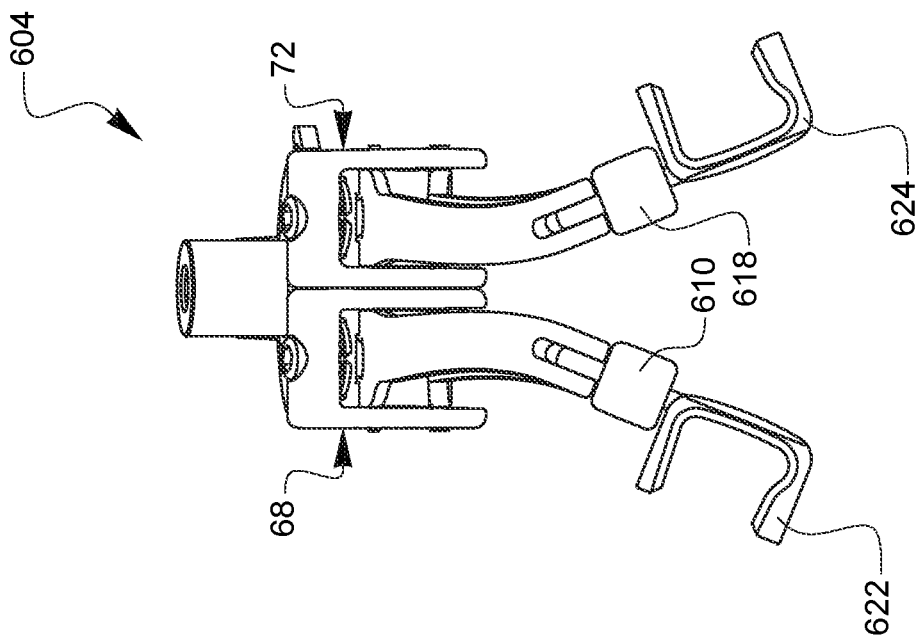
FIGS. 22A and 22B are right side and front elevational views, respectively, of the retractor of FIG. 21A where the housing and body are in a first position relative to the first and second struts.
Figure 22A:
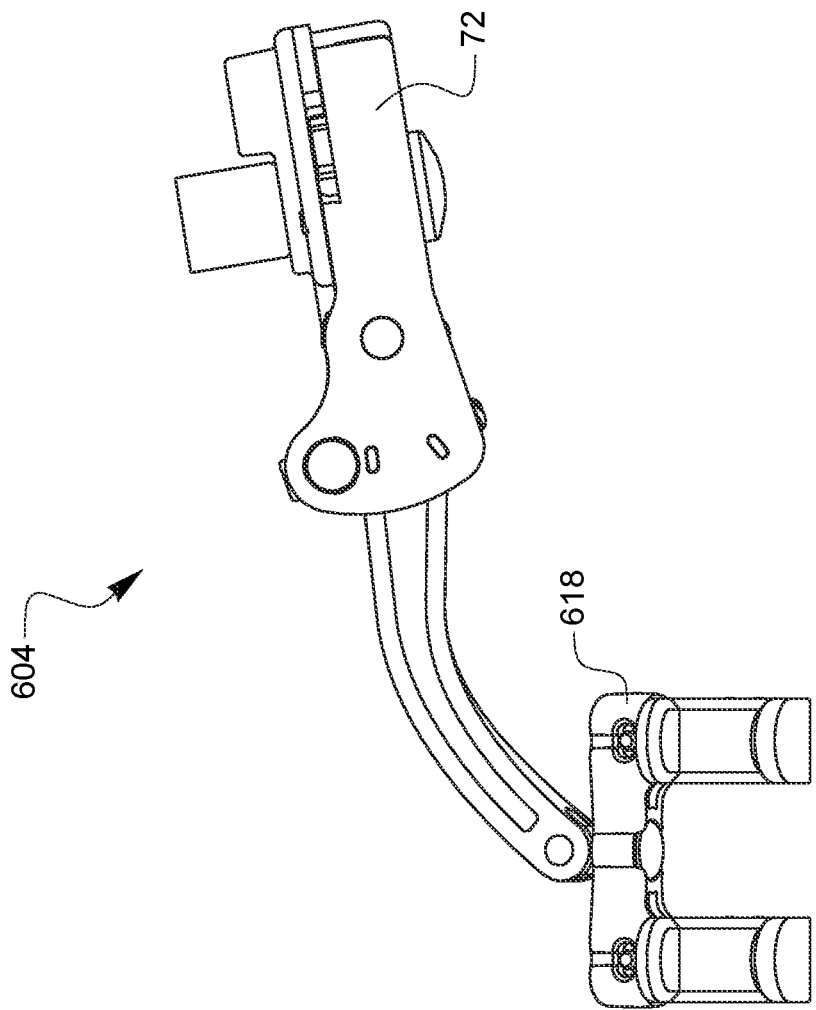

FIGS. 22A and 22B are right side and front elevational views, respectively, of the retractor 604 of FIG. 21A where the housing 68 and body 72 are in a first position relative to the first and second struts 610, 618. In this first position, while the housing 68 and body 72 are still in the closed position previously described, the rib engaging fingers 622 coupled to the first strut 610 are spread apart from the rib engaging fingers 624 coupled to the second strut 618. With the housing 68 and body 72 in this first position relative to the first and second struts 610, 618, the rib engaging fingers 622, 624 may be difficult to fit between a pair of ribs because of the separation between the rib engaging fingers 622, 624.

Figure 23B:
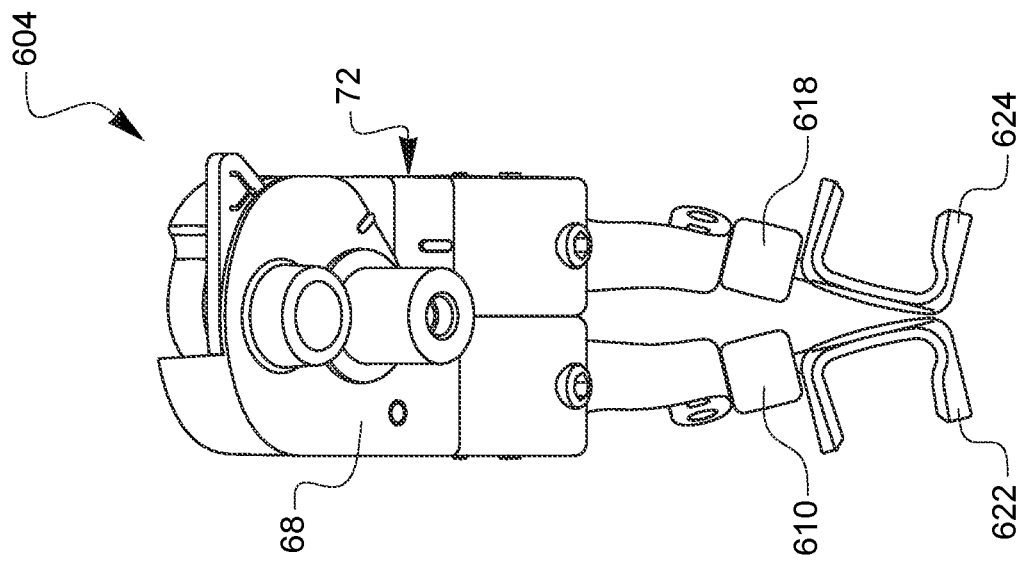
FIGS. 23A and 23B are right side and front elevational views, respectively, of the retractor of FIG. 21A where the housing and body are in a second position relative to the first and second struts.
Figure 23A:
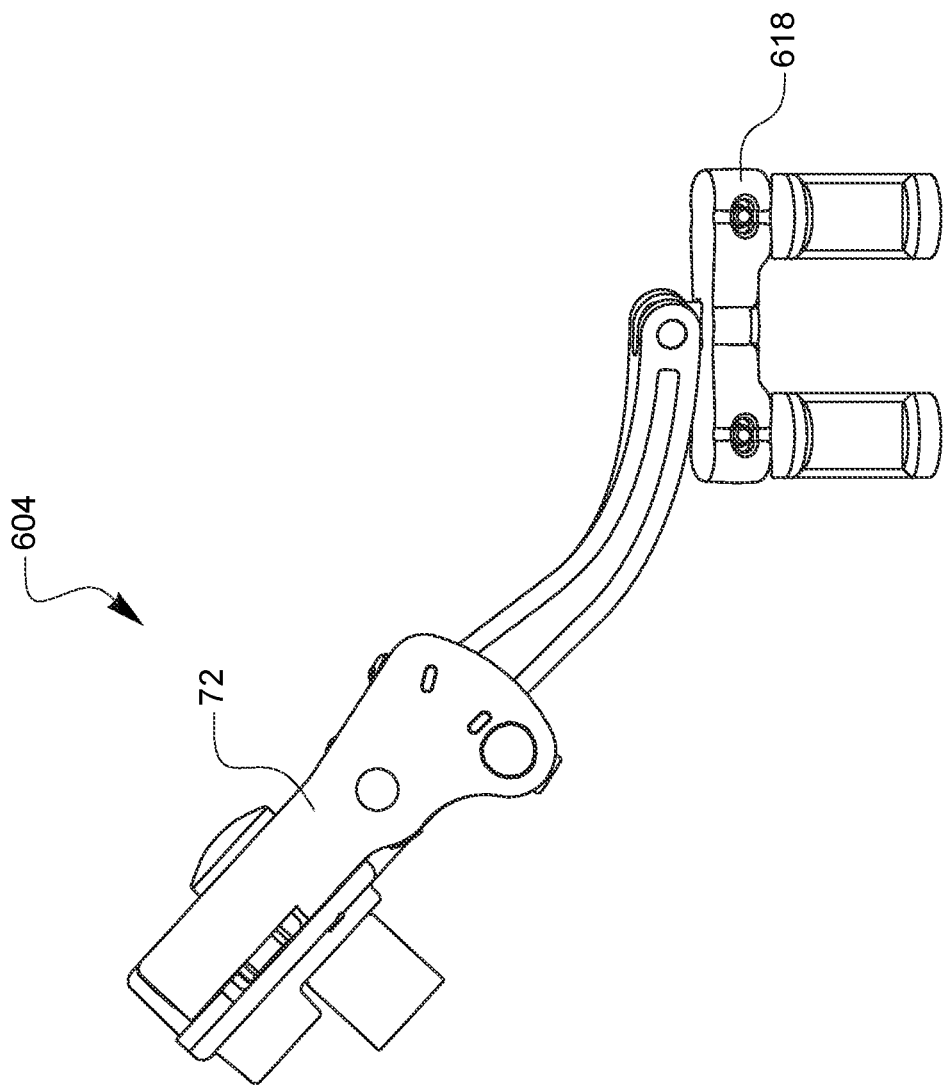

However, contrast the situation of FIGS. 22A and 22B with that shown in FIGS. 23A and 23B. FIGS. 23A and 23B are right side and front elevational views, respectively, of the retractor 604 of FIG. 21A where the housing 68 and body 72 have been rotated into a second position relative to the first and second struts 610, 618. In this second position, while the housing 68 and body 72 are still in the closed position previously described, the rib engaging fingers 622 coupled to the first strut 610 are now touching the rib engaging fingers 624 coupled to the second strut 618. While it is not necessary that the rib engaging fingers 622, 624 touch each other in this second position, they should at least be closer together than they were in the first position. With the housing 68 and body 72 in this second position relative to the first and second struts 610, 618, the rib engaging fingers 622, 624 may be easier to fit between a pair of ribs because the rib engaging fingers 622, 624 are closer together. This would allow a user to place the retractor 604 into the second position shown in FIGS. 23A, 23B for ease of insertion between a pair of ribs, and then rotate the retractor 604 into the first position shown in FIGS. 22A, 22B to help seat the rib engaging fingers 622, 624 onto the adjacent ribs in preparation for retraction. Furthermore, since the rib engaging fingers 622, 624 are starting farther apart compared to previous embodiments when the body 72 is in the closed position relative to the housing 68, when the retractor arms are opened to their widest position, the effective maximum potential opening which could be experienced by the ribs will be larger than similar embodiments could achieve without the cambering arrangement described in the embodiment of FIGS. 21A-23B.

Figure 24A:
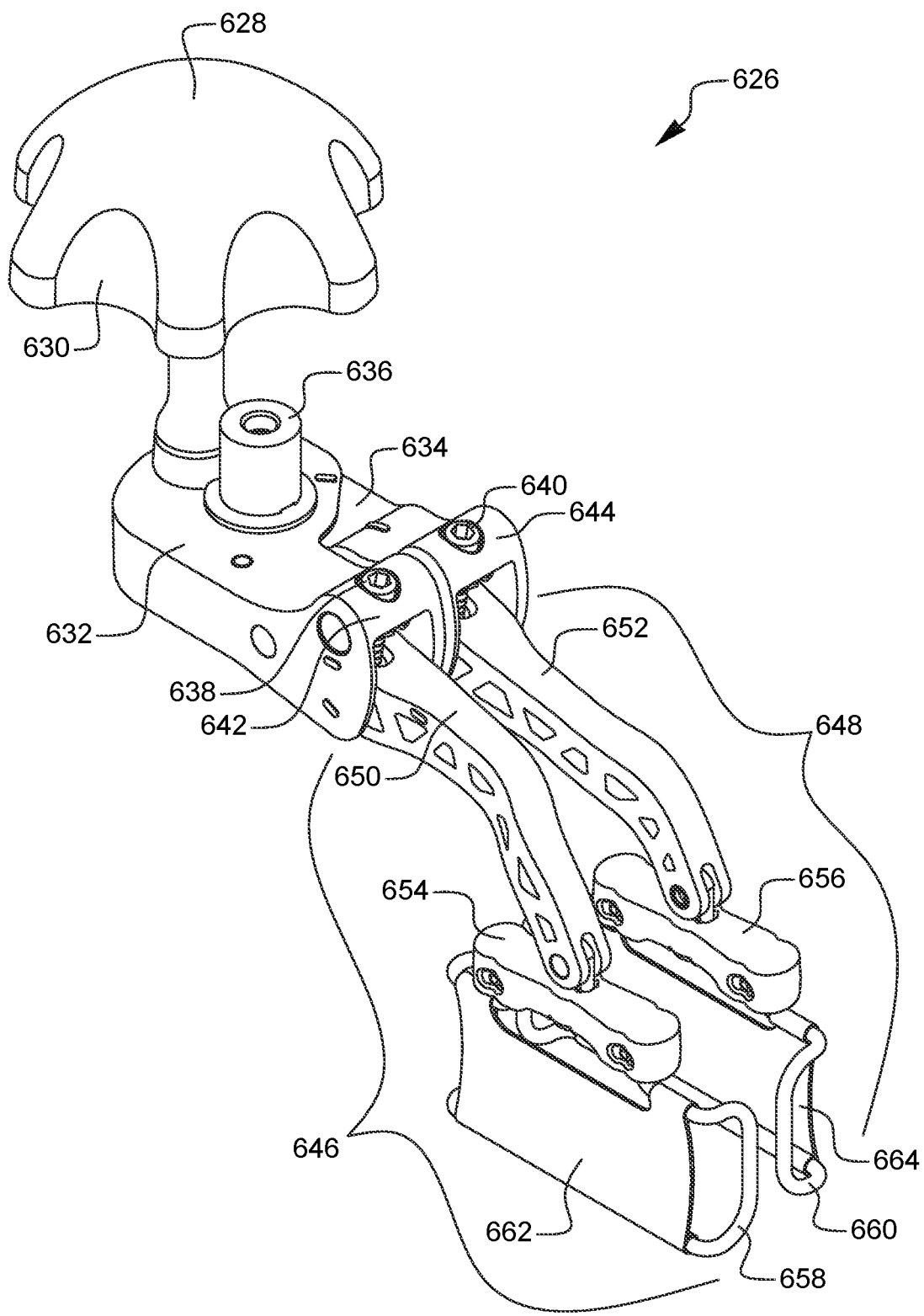
FIG. 24A is a front-top-left perspective view of another embodiment of a surgical rib retractor.

FIG. 24A is a front-top-left perspective view of another embodiment of a surgical rib retractor 626. The retractor 626 has a housing 632. The housing 632 has a first shoulder 642 and an accessory mount 636 for attaching other surgical accessories to the retractor 626 while in use. The retractor 626 also has a body 634 pivotably coupled to the housing 632 and having a second shoulder 644. The surgical rib retractor 626 also has a first arm unit 646 pivotably coupled to the first shoulder 642 and configured to atraumatically receive one rib or receive soft tissue without damaging the tissue or the rib. The surgical rib retractor 626 also has a second arm unit 648 pivotably coupled to the second shoulder 644 and configured to atraumatically receive another rib or receive soft tissue.

The surgical rib retractor 626 has a first arm actuator 638 constrained to be rotatable relative to the first shoulder 642 and coupled to the first arm unit 646 to pivot the first arm unit 646 as the first arm actuator 638 is rotated. Similarly, the retractor 626 also has a second arm actuator 640 constrained to be rotatable relative to the second shoulder 644 and coupled to the second arm unit 648 to pivot the second arm unit 648 as the second arm actuator 640 is rotated.

The surgical rib retractor 626 also has a drive actuator 628. The drive actuator 628 is configured to pivot the body 634 relative to the housing 632. In this embodiment, the drive actuator 628 includes a knob 630 and a gear (not visible in this view). In other embodiments, the drive actuator could comprise a variety of elements, including one or more gears, one or more knobs, one or more levers, one or more pulleys, one or more motors, one or more solenoids, or any combination thereof. While this embodiment of a surgical rib retractor 626 is similar to other embodiments described herein, most notably the embodiment described in regard to FIG. 1A, a significant difference is the attachment at the end of the first arm 650 and the second arm 652. The first arm 650 terminates in a first strut 654 movable relative to the first arm 650 in a first plane defined by the first arm 650. Similarly, the second arm unit 648 includes a second arm 652 and a second strut 656 moveable relative to the second arm 652 in a second plane defined by the second arm 652. A first frame 658 is fixedly attached to the first strut 654. The non-continuous structural first frame 658 initially follows a similar plane as the first strut 654, and then curves in a direction that orients another portion in a direction perpendicular to the first strut 654. This non-continuous structure occurs in two portions of the frame, but in other embodiments may occur in only one or more portions. Attached to the first frame 658 is a first resilient member 662 that is wrapped over the first frame 658. This first resilient member 662 may be made of a variety of materials such as felt, fabric, pledget-like material, and the like. Further, the first resilient member 662 may be constructed of an elastomeric or polymeric based material that provides a surface that contacts a rib or other soft anatomical tissue with a structure that spreads or equilibrates the force of exertion onto the rib or other soft tissue in a manner that spreads the force distribution across the first resilient member 662. This force distribution minimizes the potential damage to a rib or other surrounding tissue during a retraction or other minimally invasive surgical procedure using such a soft tissue retractor as this surgical rib retractor 626. When the force required for surgical separation of the ribs is exerted onto a rib or surrounding soft tissue, a concentration of force on that tissue or structure could damage the rib or surrounding tissue. Spreading out the distribution of the force exerted over the area of a resilient member or resilient sheet can reduce the potential for damage. Likewise, a second frame 660 is fixedly attached to the second strut 656. The non-continuous structural second frame 660 initially follows a similar plane as the second strut 656, and then curves in a direction that orients another portion in a direction perpendicular to the second strut 656. This non-continuous structure occurs in two portions of the frame, but in other embodiments may occur in only one or more portions. Attached to the second frame 660 is a second resilient member 664 that is wrapped over the second frame 660. Alternate embodiments may include frames that are also pivotably attached to the struts, which would provide another point of articulation for a similar rib retractor.

Figure 24B:
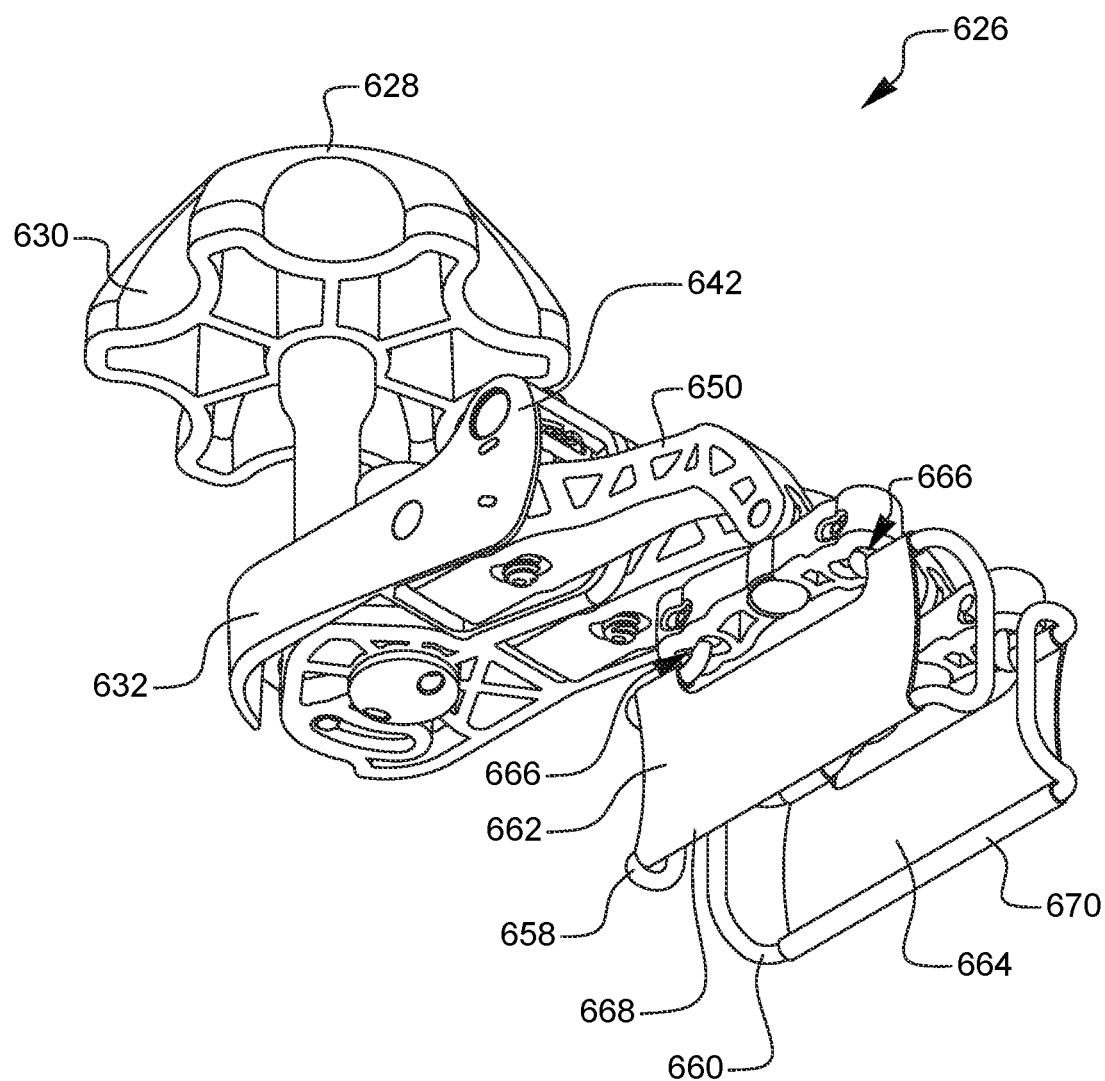
FIG. 24B is a front-bottom-left perspective view of the surgical rib retractor embodiment of FIG. 24A.

FIG. 24B is a front-bottom-left perspective view of the surgical rib retractor embodiment of FIG. 24A. In the view of FIG. 24B, the bottom side of the first and second arm actuators 638, 640 may be seen. The function of these actuators 638, 640 and other elements of this retractor 626 is similar to the function described in regard to other embodiments described herein. Also visible in FIG. 24B are the mounts 666 that attach the first frame 658 to the first strut 654. Similar mounts, not visible here, attach the second frame 660 to the second strut 656. Also in view are the wrap 668 portion of the first resilient member 662 that wraps around the first frame 658 as an attachment point and the wrap 670 portion of the second resilient member 664 that wraps around the second frame 660 as an attachment point. Other embodiments may have similar attachment features that bind or adhere or attach the resilient member to the frames or may be sewn, attached via adhesion, thermal welding or other means known to those skilled in the art.

Figure 25A:
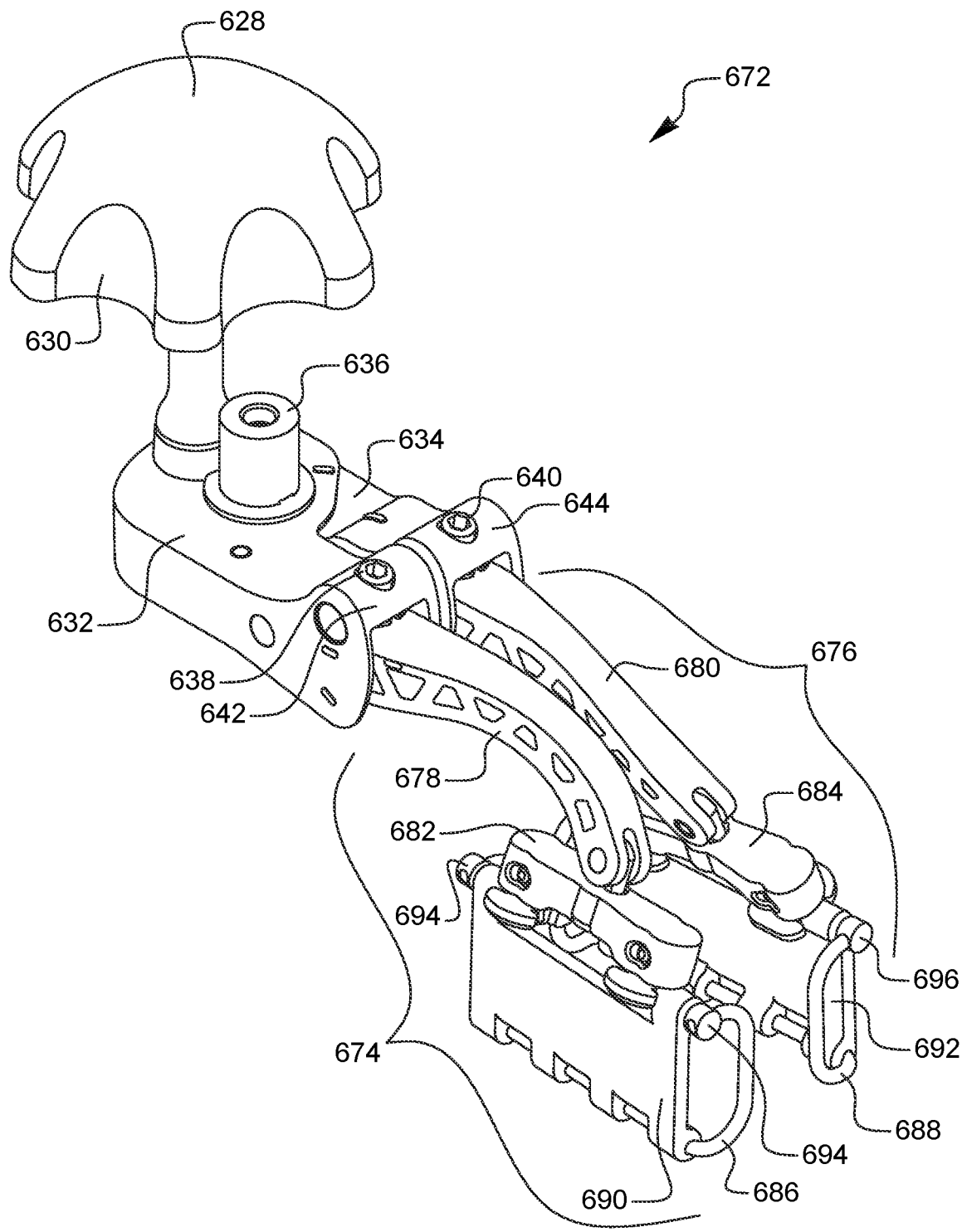
FIG. 25A is a front-top-left perspective view of another embodiment of a surgical rib retractor.

FIG. 25A is a front-top-left perspective view of another embodiment of a surgical rib retractor 672. The retractor 672 has a housing 632. The housing 632 has a first shoulder 642 and an accessory mount 636 for attaching other surgical accessories to the retractor 672 while in use. The retractor 672 also has a body 634 pivotably coupled to the housing 632 and having a second shoulder 644. The surgical rib retractor 672 also has a first arm unit 674 pivotably coupled to the first shoulder 642 and configured to atraumatically receive one rib or receive soft tissue without damaging the tissue or the rib. The surgical rib retractor 672 also has a second arm unit 676 pivotably coupled to the second shoulder 644 and configured to atraumatically receive another rib or receive soft tissue.

The surgical rib retractor 672 has a first arm actuator 638 constrained to be rotatable relative to the first shoulder 642 and coupled to the first arm unit 674 to pivot the first arm unit 674 as the first arm actuator 638 is rotated. Similarly, the retractor 672 also has a second arm actuator 640 constrained to be rotatable relative to the second shoulder 644 and coupled to the second arm unit 676 to pivot the second arm unit 676 as the second arm actuator 640 is rotated.

The surgical rib retractor 672 also has a drive actuator 628. The drive actuator 628 is configured to pivot the body 634 relative to the housing 632. In this embodiment, the drive actuator 628 includes a knob 630 and a gear (not visible in this view). In other embodiments, the drive actuator could comprise a variety of elements, including one or more gears, one or more knobs, one or more levers, one or more pulleys, one or more motors, one or more solenoids, or any combination thereof. This embodiment of a surgical rib retractor 672 is similar to other embodiments described herein, most notably the embodiment described in regard to FIGS. 20A-23B, the embodiment having the cambered arm configuration. The attachment at the end of the first arm 678 and the second arm 680 is different. The first arm 678 terminates in a first strut 682 movable relative to the first arm 678 in a first plane defined by the first arm 678. Similarly, the second arm unit 676 includes a second arm 680 and a second strut 684 moveable relative to the second arm 680 in a second plane defined by the second arm 680. A first frame 686 is fixedly attached to the first strut 682. The non-continuous structural first frame 686 initially follows a plane angled relative to the first strut 682, and then curves in a direction that orients another portion in a direction perpendicular to the first plane as defined by the first frame 686. This non-continuous structure occurs in two portions of the frame, but in other embodiments may occur in only one or more portions. Attached to the first frame 686 is a first resilient member 690 that is wrapped over the first frame 686. This first resilient member 690 may be made of a variety of materials such as felt, fabric, pledget-like material, and the like. The first resilient member 690 may also be molded over the frame 686. Further, the first resilient member 690 may be constructed of an elastomeric or polymeric based material that provides a surface that contacts a rib or other soft anatomical tissue with a structure that spreads or equilibrates the force of exertion onto the rib or other soft tissue in a manner that spreads the force distribution across the first resilient member 690. This force distribution minimizes the potential damage to a rib or other surrounding tissue during a retraction or other minimally invasive surgical procedure using such a soft tissue retractor as this surgical rib retractor 672. When the force required for surgical separation of the ribs is exerted onto a rib or surrounding soft tissue, a concentration of force on that tissue or structure could damage the rib or surrounding tissue. Spreading out the distribution of the force exerted over the area of a resilient member or resilient sheet can reduce the potential for damage. Likewise, a second frame 688 is fixedly attached to the second strut 684. The non-continuous structural second frame 688 initially follows a plane angled relative to the second strut 684, and then curves in a direction that orients another portion in a direction perpendicular to the first plane defined by the second frame 688. This non-continuous structure occurs in two portions of the frame, but in other embodiments may occur in only one or more portions. Attached to the second frame 688 is a second resilient member 692 that is wrapped over the second frame 688. Alternate embodiments may include frames that are also pivotably attached to the struts, which would provide another point of articulation for a similar rib retractor.

Figure 25B:
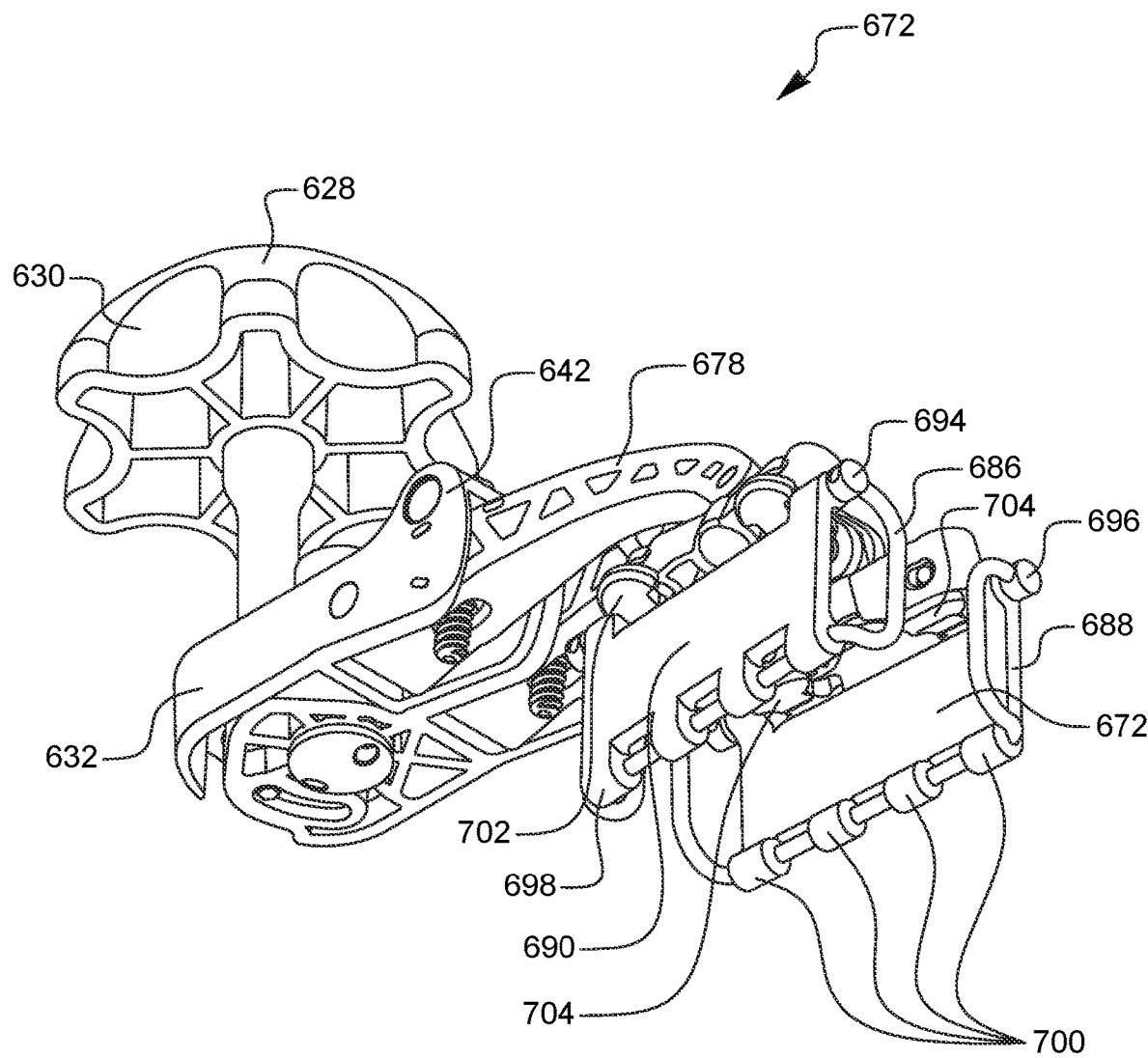
FIG. 25B is a front-bottom-left perspective view of the surgical rib retractor embodiment of FIG. 25A.

FIG. 25B is a front-bottom-left perspective view of the surgical rib retractor embodiment of FIG. 25A. In the view of FIG. 25B, the bottom side of the first and second arm actuators 638, 640 may be seen. The function of these actuators 638, 640 and other elements of this retractor 626 is similar to the function described in regard to other embodiments described herein. Also visible in FIG. 25B are the mounts 702 that attach the first frame 686 to the first strut 682. Similar mounts 704 attach the second frame 688 to the second strut 684. Also in view are the wrap 698 portion of the first resilient member 690 that wraps around the first frame 686 as an attachment point and the wrap 700 portion of the second resilient member 692 that wraps around the second frame 688 as an attachment point. Other embodiments may have similar attachment features that bind or adhere or attach the resilient member to the frames or may be sewn, attached via adhesion, thermal welding or other means known to those skilled in the art. Also shown in this embodiment are frame pin mounts 694 that attach the first frame 686 to the first strut 682, and the frame pin mounts 696 that attach the second frame 688 to the second strut 684.

Figure 26:
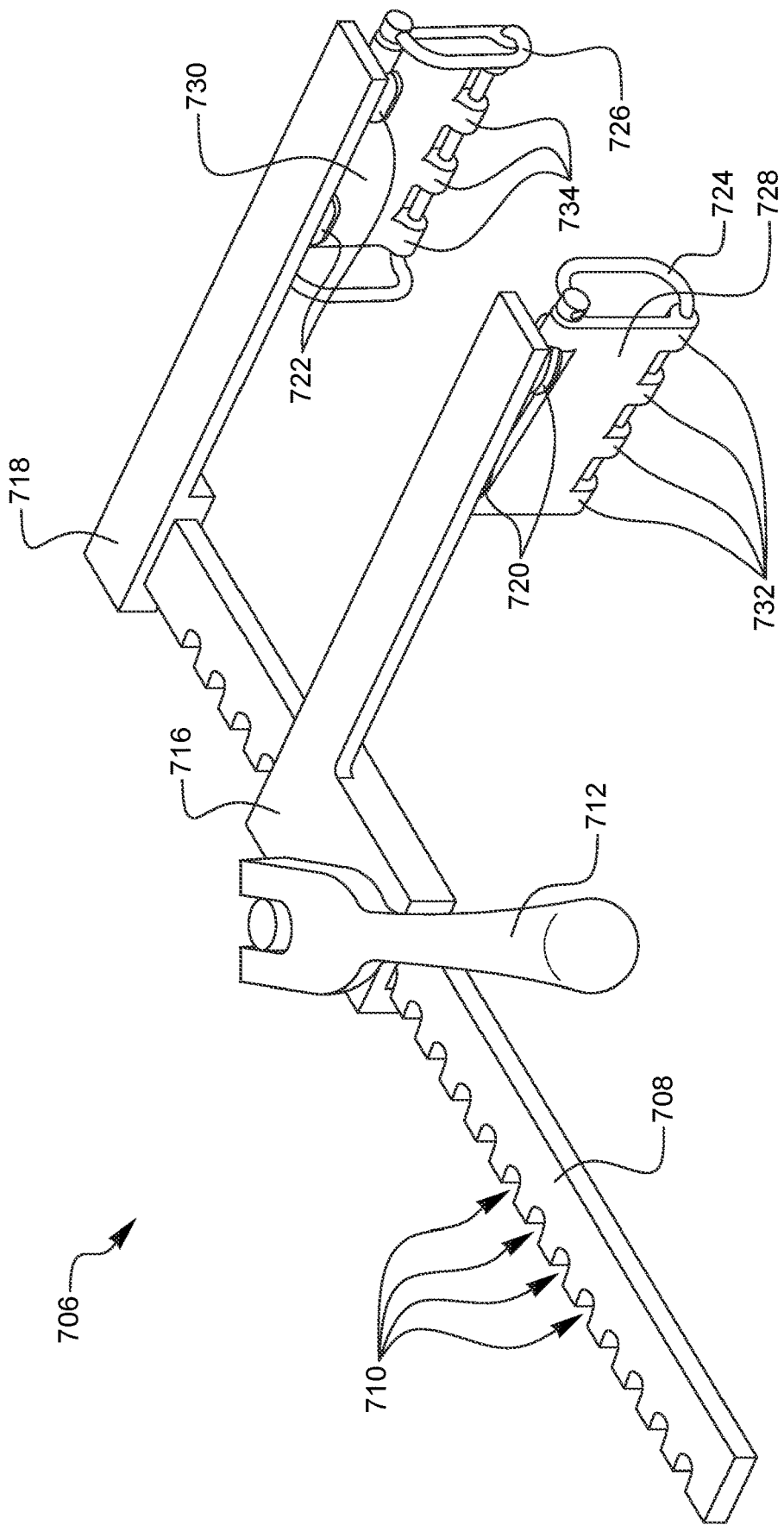
FIG. 26 is a front-top-left perspective view of another embodiment of a surgical rib retractor.

FIG. 26 is a front-top-left perspective view of another embodiment of a surgical rib retractor 706. The rib retractor 706 is constructed of a linear gear 708 having several gears 710 with a first arm 716 movably attached to the linear gear 708, and a second arm 718 fixedly attached to one end of the linear gear 708. The first arm 716 has two first frame mounts 720 upon which a first frame 724 is attached to the first arm 716. The first arm 716 has a first resilient member 728 attached with several points 732 about which the first resilient member 728 is wrapped around the first frame 724. Likewise, attached to the second arm 718 are two second frame mounts 722 upon which a second frame 726 is attached to the second arm 718. A second resilient member 730 is wrapped around the first frame 724 and attached at several points 734 around the first frame 724. Other embodiments may have different arm arrangements or alternate attachment methods for frames and resilient members to arms or other structures useful in retraction operations or procedures similar to those described herein.

Various advantages of a surgical rib retractor have been discussed above. Embodiments discussed herein have been described by way of example in this specification. It will be apparent to those skilled in the art that the foregoing detailed disclosure is intended to be presented by way of example only and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. As one example, although a knob and drive screw were used as examples of actuators herein, it should be apparent to those skilled in the art that other types of actuators may be used to create a similar relative movement between the posterior and anterior arm units. As some non-limiting examples, other actuators may include, but are not limited to, a ratchet mechanism, a geared mechanism, a levered mechanism, a motorized mechanism, or any combination and/or plurality thereof. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:
1. A surgical rib retractor, comprising:
a) a housing;
b) a body pivotably coupled to the housing and moveable between a closed position and an open position;
c) a first arm unit coupled to the housing and configured to atraumatically receive tissue, wherein the first arm unit comprises:
   1) A first arm having a first longitunal axis, and;
   2) A first strut movable relative to the first arm in a first plane defined by the first longitudinal axis; and
   3) A first frame attached to the first strut,
d) a second arm unit coupled to the body and configured to atraumatically receive tissue, wherein the second arm unit comprises:
   1) A second arm having a second longitudinal axis;
   2) A second strut movable relative to the second arm in a second plane defined by the second arm having a second longitudinal axis, wherein the second plane is not parallel to the first plane when the body is in the closed position; and
   3) A second frame attached to the second strut, wherein:
the housing comprises a first shoulder;
the body comprises a second shoulder;
the first arm unit is pivotably coupled to the housing at the first shoulder;
the second arm is unit pivotably coupled to the body by the second shoulder; and
the surgical rib retractor further comprises:
a first arm actuator constrained to be rotatable relative to the first shoulder and coupled to the first arm unit to pivot the first arm unit as the first arm actuator is rotated; and
a second arm actuator constrained to be rotatable relative to the second shoulder and coupled to the second arm unit to pivot the second arm unit as the second arm actuator is rotated.

2. The surgical rib retractor of claim 1, wherein the first frame and the second frame are each non-continuous.

3. The surgical rib retractor of claim 1, wherein the first frame further comprises a resilient member attached to the first frame.

4. The surgical rib retractor of claim 1, wherein the second frame further comprises a resilient member attached to the second frame.

5. A surgical rib retractor, comprising:
a housing having a first shoulder, wherein the housing defines an actuator guide opening;
a body comprising a second shoulder and a drive gear, the body pivotably coupled to the housing;
a first arm unit comprising a first frame, pivotably coupled to the first shoulder and configured to atraumatically receive tissue;
a second arm unit comprising a second frame, pivotably coupled to the second shoulder and configured to atraumatically receive tissue;
a first arm actuator constrained to be rotatable relative to the first shoulder and coupled to the first arm unit to pivot the first arm unit as the first arm actuator is rotated;
a second arm actuator constrained to be rotatable relative to the second shoulder and coupled to the second arm unit to pivot the second arm unit as the second arm actuator is rotated;
a drive actuator configured to pivot the body relative to the housing, comprising:
an actuation gear;
a knob;
a pawl arm deflection portion; and
an actuation key configured to engage at least one of the first and second arm actuators for rotation; and
wherein the actuator guide opening is sized to accept the actuation gear and align it with the drive gear for turning the drive gear.

6. A surgical rib retractor, comprising:
a housing having a first shoulder;
a body pivotably coupled to the housing and having a second shoulder;
a first arm unit comprising a first arm having a first longitudinal axis, and a first frame, pivotably coupled to the first shoulder and configured to atraumatically receive tissue;
a second arm unit comprising a second arm having a second longitudinal axis, and a second frame, pivotably coupled to the second shoulder and configured to atraumatically receive tissue;
a first arm actuator constrained to be rotatable relative to the first shoulder and coupled to the first arm unit to pivot the first arm unit in a first plane defined by the first longitudinal axis as the first arm actuator is rotated;
a second arm actuator constrained to be rotatable relative to the second shoulder and coupled to the second arm unit to pivot the second arm unit in a second plane defined by the second longitudinal axis as the second arm actuator is rotated; and
a drive actuator configured to pivot the body relative to the housing.

7. The surgical rib retractor of claim 6, wherein the housing defines an actuator guide opening.

8. The surgical rib retractor of claim 6, wherein the body further comprises a drive gear.

9. The surgical rib retractor of claim 6, wherein the body further comprises a ratchet gear.

10. The surgical rib retractor of claim 9, further comprising a pawl arm having a pawl which is biased against the ratchet gear.

11. The surgical rib retractor of claim 6, wherein the drive actuator comprises an element selected from the group consisting of a gear, a knob, a lever, a pulley, a motor, and a solenoid.

12. The surgical rib retractor of claim 6, wherein:
the body further comprises a drive gear;
the drive actuator comprises an actuation gear and a knob; and
the housing defines an actuator guide opening sized to accept the actuation gear and align it with the drive gear for turning the drive gear.

13. The surgical rib retractor of claim 6, wherein:
the body further comprises a ratchet gear;
the surgical rib retractor further comprises a pawl arm having a pawl which is biased against the ratchet gear; and
the drive actuator further comprises a pawl arm deflection portion.

14. The surgical rib retractor of claim 6, wherein the drive actuator further comprises an actuation key configured to engage at least one of the first and second arm actuators for rotation.

15. The surgical rib retractor of claim 6, wherein a) relative movement between the housing and body and b) the relative movement between at least one of a) the first arm unit and the first shoulder or b) the second arm unit and the second shoulder comprises at least two directional components.

16. The surgical rib retractor of claim 15, wherein the at least two directional components comprise:
a direction substantially parallel to an anterior-posterior axis; and
a direction substantially parallel to a cephalad-caudal axis.

17. The surgical rib retractor of claim 15, wherein the at least two directional components comprise:
a substantially paratransverse component; and
a substantially paracoronal component.

18. The surgical rib retractor of claim 15, wherein the at least two directional components comprise:
a direction substantially parallel to an anterior-posterior axis; and
a substantially paracoronal component.

19. The surgical rib retractor of claim 15, wherein the at least two directional components comprise:
a linear component; and
an arcuate component.

20. The surgical rib retractor of claim 15, wherein the at least two directional components comprise:
a first component parallel to a first axis; and
a second component in a plane substantially perpendicular to the first axis.

21. The surgical rib retractor of claim 6, wherein the first arm unit comprises:
a first arm; and
a first strut.

22. The surgical rib retractor of claim 21, wherein the first arm and the first strut are continuous.

23. The surgical rib retractor of claim 21, wherein the first strut is flexible.

24. The surgical rib retractor of claim 21, wherein the first frame is coupled to a portion of the first strut.

25. The surgical rib retractor of claim 24, further comprising a first resilient member attached to the first frame.

26. The surgical rib retractor of claim 6, wherein the second arm unit comprises:
a second arm; and
a second strut.

27. The surgical rib retractor of claim 26, wherein the second arm and the second strut are continuous.

28. The surgical rib retractor of claim 26, wherein the second strut is flexible.

29. The surgical rib retractor of claim 26, wherein the second frame is coupled to a portion of the second strut.

30. The surgical rib retractor of claim 29, further comprising a second resilient member attached to the second frame.

31. The surgical rib retractor of claim 6, further comprising an anti-cant feature.

32. The surgical rib retractor of claim 6, further comprising a drive gear component coupled to the body.

33. The surgical rib retractor of claim 6, further comprising a ratchet gear component coupled to the body.

\* \* \* \* \*